United States Patent
Mikamiyama et al.

(10) Patent No.: US 8,895,551 B2
(45) Date of Patent: Nov. 25, 2014

(54) ACRYLAMIDE COMPOUNDS AND THE USE THEREOF

(75) Inventors: Hidenori Mikamiyama, Osaka (JP); Akira Matsumura, Osaka (JP); Moriyasu Masui, Osaka (JP); Kosuke Anan, Osaka (JP); Kayoko Hata, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 313 days.

(21) Appl. No.: 13/260,185

(22) PCT Filed: Apr. 2, 2010

(86) PCT No.: PCT/JP2010/056404
§ 371 (c)(1),
(2), (4) Date: Sep. 23, 2011

(87) PCT Pub. No.: WO2010/114181
PCT Pub. Date: Oct. 7, 2010

(65) Prior Publication Data
US 2012/0022069 A1    Jan. 26, 2012

Related U.S. Application Data

(60) Provisional application No. 61/166,206, filed on Apr. 2, 2009.

(51) Int. Cl.
| | | |
|---|---|---|
| A61K 31/5377 | (2006.01) | |
| C07D 265/30 | (2006.01) | |
| A61K 31/445 | (2006.01) | |
| C07D 211/68 | (2006.01) | |
| C07D 401/00 | (2006.01) | |
| C07D 405/00 | (2006.01) | |
| C07D 211/70 | (2006.01) | |
| C07D 211/96 | (2006.01) | |

(52) U.S. Cl.
CPC ............ *C07D 211/70* (2013.01); *C07D 211/96* (2013.01)
USPC ........ 514/237.8; 514/318; 514/326; 514/331; 544/159; 546/194; 546/207; 546/213; 546/214; 546/230; 546/233; 546/234

(58) Field of Classification Search
USPC ............... 514/237.8, 318, 326, 331; 544/159; 546/194, 207, 213, 214, 230, 233, 234
See application file for complete search history.

(56) References Cited

U.S. PATENT DOCUMENTS

| | | | |
|---|---|---|---|
| 5,360,819 A | 11/1994 | Giese | |
| 6,087,379 A | 7/2000 | Asai et al. | |
| 6,136,839 A | 10/2000 | Isakson et al. | |
| 2004/0171640 A1 | 9/2004 | Sundermann et al. | |
| 2004/0186292 A1 | 9/2004 | Wang et al. | |

FOREIGN PATENT DOCUMENTS

| | | |
|---|---|---|
| CN | 1235596 | 11/1999 |
| EP | 0 330 467 A1 | 8/1989 |
| EP | 0 934 928 A1 | 8/1999 |
| EP | 1 403 255 A1 | 3/2004 |
| JP | 62158291 A | 7/1987 |
| WO | WO 02/100833 A1 | 12/2002 |
| WO | WO 03/004026 A2 | 1/2003 |
| WO | WO 2004-022535 A1 | 3/2004 |
| WO | WO 2004/043337 A2 | 5/2004 |
| WO | WO 2005/097774 A1 | 10/2005 |
| WO | WO 2006/024160 A1 | 3/2006 |
| WO | WO 2006/040181 A2 | 4/2006 |
| WO | WO 2007/002057 A1 | 1/2007 |
| WO | WO 2007/002361 A2 | 1/2007 |
| WO | WO 2007/028638 A1 | 3/2007 |
| WO | WO 2007/071035 A1 | 6/2007 |
| WO | WO 2007/075555 A2 | 7/2007 |
| WO | WO 2007/085357 A1 | 8/2007 |
| WO | WO 2007/110449 A1 | 10/2007 |
| WO | WO 2007-118137 A1 | 10/2007 |
| WO | WO 2007/118853 | 10/2007 |
| WO | WO 2007/118854 | 10/2007 |
| WO | WO 2007/125398 A2 | 11/2007 |
| WO | WO 2008/008398 A2 | 1/2008 |
| WO | WO 2008-092844 A1 | 8/2008 |
| WO | WO 2008/124118 A1 | 10/2008 |
| WO | WO 2008/150447 A1 | 12/2008 |
| WO | WO 2008-150447 A1 | 12/2008 |

(Continued)

OTHER PUBLICATIONS

Notification Concerning Transmittal of International Preliminary Report on Patentability, including Written Opinion of the International Searching Authority, for International Application No. PCT/JP2010/056404, mailed Oct. 13, 2011 (8 pages).

(Continued)

*Primary Examiner* — Samantha Shterengarts
(74) *Attorney, Agent, or Firm* — Finnegan, Henderson, Farabow, Garrett & Dunner, LLP

(57) ABSTRACT

The invention relates to acrylamide compounds of Formula I mentioned below. The invention is also directed to the use compounds of Formula I to treat or prevent a disorder responsive to the blockade of calcium channels, and particularly N-type calcium channels. Compounds of the present invention are especially useful for treating pain.

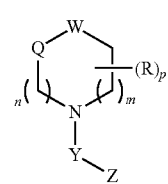

17 Claims, No Drawings

(56) References Cited

FOREIGN PATENT DOCUMENTS

| WO | WO 2008/150470 A1 | 12/2008 |
|---|---|---|
| WO | WO 2009/040659 A2 | 4/2009 |
| WO | WO 2009/151152 A1 | 12/2009 |
| WO | WO 2010/014257 A2 | 2/2010 |

OTHER PUBLICATIONS

Krehan, D. et al., "Potent 4-Arylalkyl-Substituted 3-Isothiazolol GABAa Competitive/Noncompetitive Antagonists: Synthesis and Pharmacology," *Journal of Medicinal Chemistry*, 49(4): 1388-1396 (2006).

Davila, H.M., "Molecular and Functional Diversity of Voltage-Gated Calcium Channels", Annals of the New York Academy of Sciences, pp. 102-117 (1999).

Hu, L-Y., et al., "The Discovery of [1-(4-Dimethylamino-benzyl)-piperidin-4-yl]-[4-(3,3-dimethylbutyl)-phenyl]-(3-methyl-but-2-enyl)-Amine, an N-type $Ca^{+2}$ Channel Blocker with Oral Activity for Analgesia", Bioorganic & Medicinal Chemistry 8, pp. 1203-1212 (2000).

Song, Y., et al., "(S)-4-Methyl-2-(methylamino)pentanoic Acid [4,4-Bis(4-fluorophenyl)(butyl]amide Hydrochloride, a Novel Calcium Channel Antagonist, Is Efficacious in Several Animal Models of Pain", Journal Medicinal Chemistry 43, pp. 3474-3477 (2000).

Wallace, M.S., "Calcium and Sodium Channel Antagonists for the Treatment of Pain", The Clinical Journal of Pain 16, pp. 580-585 (2000).

Vanages, H., et al "Effects of antagonists to High-Threshold Calcium Channels Upon Spinal Mechanisms of Pain. Hyperalgesia and Allodynia,", Pain 85, pp. 9-18 (2000).

Etayo, P., et al., "Base-Controlled Diastereodivergent Synthesis of (R)- and (S)-2-Substituted-4-alkylidenepiperidines by the Wadsworth-Emmons Reaction", Journal of Organic Chemistry 72, pp. 1005-1008 (2007).

Suzuki, K. et al., "A Dual Antagonist for Chemokine CCR3 Receptor and Histamine $H_1$ Receptor", European Journal of Pharmacology 563, pp. 224-232 (2007).

De Lucca, G.V., "Recent Developments in CCR3 Antagonists", Current Opinion in Drug Discovery & Development 9, pp. 516-524 (2006).

Morokata, T., et al., "A Novel, Selective, and Orally Available Antagonist for CC Chemokine Receptor 3", The Journal of Pharmacology and Experimental Therapeutics 317, pp. 244-250 (2006).

Suzuki, K., et al., "In Vitro and in Vivo Characterization of a Novel CCR3 Antagonist, YM-344031", Biochemical and Biophysical Research Communications 339, pp. 1217-1223 (2006).

Krehn, D., et al., "Potent 4-Arylalkyl-Substituted 3-Isothiazolol $GABA_A$ Competitive/Noncompetitive Antagonists: Synthesis and Pharmacology", Journal of Medicinal Chemistry 49, pp. 1388-1396 (2006).

Heitz, J.R. "Inhibition of Yeast Alcohol Dehydrogenase by $N^1$.Benzylpyridinium Chlorides", Molecular Pharmacology 4, pp. 44-52 (1968).

Bundgaard, H., "Design and Application of Prodrugs", Chapter 5 (pp. 113-191) in "A Textbook of Drug Design and Development," P. Krogsgaard-Larsen and H. Bundgaard eds., Harwood Academic Publishers (1991).

Bungaard, H., et al., "(C) Means to Enhance penetration", Advanced Drug Delivery Reviews 8, pp. 1-38 (1992).

Bundgaard, H., et al., "Glycolamide Esters as Biolabile Prodrugs of Carboxylic Acid Agents: Synthesis, Stability, Cioconversion, and Physicochemical Properties", Journal of Pharmaceutical Sciences 77, pp. 285-298 (1988).

Kakekya, N.. et al., "Studies on Prodrugs of Cephalosporins. I, Synthesis and Biological Properties of Glycyloxybenzoyloxymethyl and Glycylaminobenzoyloxymethyl Esters of 7β-[2-Aminothiazol-4-yl)-(Z)-2-methoxyiminoacetamido]-3-metyl-3-cephem-4-carboxylic Acid", Chemical Pharm. Bulletin 32, pp. 692-698 (1984).

Filer, C.N., "The Preparation and Characterization of Tritiated Neurochemicals," Chapter 6 (pp. 156-193) in "Isotopes in the Physical and Biomedical Sciences, vol. 1, Labeled Compounds (Part A)", Buncel, E., et al., eds, published by Elsevier (1987).

Caira, M.R., et al., "Preparation and Crystal Characterization of a Polymorph, a Monohydrate, and an Ethyl Acetate Solvate of the Antifungal Fluconazole", Journal of Pharmaceutical Sciences 93, pp. 601-611 (2004).

van Tonder, E.C., et al., "Preparation and Physicochemical Characterization of 5 Niclosamide Solvates and 1 Hemisolvate", AAPS PharmSciTech 5, pp. 1-10 (2004).

Bingham, A.L., et al.,"Over One Hundred Solvates of Sulfathiazole", Chem. Commun., pp. 603-604 (2001).

Brower, V., "New Paths to Pain Relief", Nature Biotechnology 18, pp. 387-391 (2000).

Levine, J., et al., "Inflammatory Pain", pp. 45-56 in Textbook of Pain, Wall and Melzack eds., 3rd ed. (1994).

Dubel, S.J., et al., "Molecular Cloning of the α-1 Subunit of an W-conotoxin-sensitive Calcium Channel", Proc. Nat., Acad. Sci USA 89, pp. 5058-5062 (1992).

Pragnell, M., et al., "Cloning and Tissue-Specific Expression of the Brain Calcium Channel β-subunit", Federation of European Biochemical Societies 291, pp. 253-258 (1991).

Castellano, A., et al., "Cloning and Expression of a Nueronal Calcium Channel β Subunit",the Journal of Biological Chemistry 268, pp. 12359-12366(1993).

Kim, H.-L., et al., "Rat Brain Expresses an Alternatively Spliced Form of the Dihydropyridine-sensitive L-type Calcium Channel α2 subunit", Proc. Natal. Acad. Sci. USA 89, pp 3251-3255 (1992).

Koch, W.J., et al., "cDNA Cloning of a Dihydropyridine-Sensitive Calcium Channel from Rat Aorta", The Journal of Biological Chemistry 265, pp. 17786-17791 (1990).

Lin, Z. et al., "Identification of Functionally Distinct Isoforms of the N-Type $Ca^{2+}$ Channel in Rat Sympathetic Ganglia and Brain", Neuron 18, pp. 153-166 (1997).

Hamill, O.P., et al., "Improved Patch-Clamp Techniques for High-Resolution Current Recording from Cells and Cell-Free Membrane Patches", Pflugers Arch.,391, pp. 85-100 (1981).

Hunskaar, S. O., et al., "Formalin Test in Mice, a Useful Technique for Evaluating Mild Analgesics", Journal of Neuroscience Methods 14, pp. 69-76 (1985).

Kim, S.H., et al., "An Experimental Model for Peripheral Neuropathy Produced by Segmental Spinal Nerve Ligation in the Rat", Pain 50, pp. 355-363 (1992).

Stein, C., et al., "Unilateral Inflammation of the Hindaw in Rats as a Model of Prolonged Noxious Stimulation: Alterations in Behavior and Nociceptive Thresholds", Pharmacology,Biochemistry & Behavior 31, pp. 445-451 (1988).

Insel. P. A., "Analgesic Antipyretic and Antiinflammatory Agents and Drugs Employed in the Treatment of Gout", Chapter 7 (pp. 617-657) in Goodman & Gilman's "The Pharmacological Basis of Therapeutics", $9^{th}$ ed. (1996).

Hanson, G.R., "Analgesic, Antipyretic and Anti-inflammatory Drugs", pp. 1196-1221 in Remington: The Science and Practice of Pharmacy, vol. II, Gennaro, A.R. ed. 19th ed. (1995).

Sato, I., et al., "Synthesis, Biological Evaluation, and Metabolic Stability of Acrylamide Derivatives as Novel CCR3 Antagonists", Bioorganic & Medicinal Chemistry 17, pp. 5989-6002 (2009).

Chinese Office Action dated Feb. 27, 2013, for Chinese Patent Application No. 201080021407.2 (7 pages).

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
caccatggtc cgcttcgggg ac                                              22

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
ccgttcagtg gcctcctcc                                                  19

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3
```
ctagcaccag tgatcctggt ctg     23

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
agtgcgttgt gagcgcagta     20

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
caccatggtc cagaagagcg g     21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tctcagcgga tgtagacgcc t     21

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
caccatgtat gacgactcct ac     22

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
ggtggtcagt agctgtcctt agg     23

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
caccatggct gctggctgcc t     21

<210> SEQ ID NO 10
<211> LENGTH: 25
<212> TYPE: DNA
<213> ORGANISM: Artificial Sequence

```
<220> FEATURE:
<223> OTHER INFORMATION: primer

<400> SEQUENCE: 10
agagggtcac catagatagt gtctg                                    25

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
caccatgatt cgggccttcg ct                                       22

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
agcctgcgga ctacaggttg ctgac                                    25
```

ACRYLAMIDE COMPOUNDS AND THE USE THEREOF

CROSS REFERENCE TO RELATED APPLICATIONS

This application is a national phase application under 35 U.S.C. 371 based on International Application No. PCT/JP2010/056404, filed Apr. 2, 2010, which claims the benefit of U.S. Provisional Application No. 61/166,206, filed Apr. 2, 2009, the entire content of both of which is hereby incorporated by reference.

TECHNICAL FIELD

This invention is in the field of medicinal chemistry. The invention relates to acrylamide compounds and the use of these compounds as blockers of calcium ($Ca^{2+}$) channels.

BACKGROUND ART

Calcium ions play fundamental roles in the regulation of many cellular processes. It is therefore essential that their intracellular levels be maintained under strict, yet dynamic control (NPL1). Voltage-gated calcium channels (VGCC) serve as one of the important mechanisms for fast calcium influx into the cell. Calcium channels are hetero-oligomeric proteins consisting of a pore-forming subunit (α1), which is able to form functional channels on its own in heterologous expression systems, and a set of auxiliary or regulatory subunits. Calcium channels have been classified based on their pharmacological and/or electrophysiological properties. The classification of voltage-gated calcium channels divides them into three groups: (i) high voltage-activated (HVA) channels, which include L-, N-, P-, and Q-types; (ii) intermediate (IVA) voltage-activated R-type channels; and (iii) low voltage-activated (LVA) T-type channels (NPL1). Voltage-gated calcium channels (VGCC) are also known as voltage-dependent calcium channels (VDCC) or voltage-sensitive calcium channels (VSCC). Voltage-sensitive calcium channels (VSCC) regulate intracellular calcium concentration, which affects various important neuronal functions such as cellular excitability, neurotransmitter release, hormone secretion, intracellular metabolism, neurosecretory activity and gene expression (NPL2). N-type channels are found mainly in central and peripheral neurons, being primarily located on presynaptic nerve terminals. These channels regulate the calcium flux required for depolarization-evoked release of a transmitter from synaptic endings. The transmission of pain signals from the periphery to the central nervous system (CNS) is mediated by N-type calcium channels located in the spinal cord (NPL3).

The six types of calcium channels (i.e., L, N, P, Q, R, and T) are expressed throughout the nervous system (NPL4). Voltage-sensitive calcium channels of the N-type exist in the superficial laminae of the dorsal horn and are thought to modulate nociceptive processing by a central mechanism. Blockade of the N-type calcium channel in the superficial dorsal horn modulates membrane excitability and inhibits neurotransmitter release, resulting in pain relief. Wallace (NPL4) suggests that based on animal models, N-type calcium channel antagonists have a greater analgesic potency than sodium channel antagonists.

N-type calcium channel blockers have usefulness for neuroprotection and analgesia. Ziconotide, which is a selective N-type calcium channel blocker, has been found to have analgesic activity in animal models and neuroprotective activity in focal and global ischemia models (NPL3). Examples of known calcium channel blockers include flunarizine, fluspirilene, cilnipide, PD 157767, SB-201823, SB-206284, NNC09-0026, and PD 151307 (NPL2).

Blockade of N-type channels can prevent and/or attenuate subjective pain as well as primary and/or secondary hyperalgesia and allodynia in a variety of experimental and clinical conditions (NPL5). N-type voltage-gated calcium channels (VGCC) play a major role in the release of synaptic mediators such as glutamate, acetylcholine, dopamine, norepinephrine, gamma-aminobutyric acid (GABA) and calcitonin gene-related peptide (CGRP).

Inhibition of voltage-gated L-type calcium channels has been shown to be beneficial for neuroprotection (NPL3). However, inhibition of cardiac L-type calcium channels can lead to hypotension. It is believed that a rapid and profound lowering of arterial pressure tends to counteract the neuroprotective effects of L-type calcium channel blockers. A need exists for antagonists that are selective for N-type calcium channels over L-type calcium channels to avoid potential hypotensive effects.

Similar compounds to those of the present invention are described in the following documents but the structures of these compounds are different from those of the present invention:
PTL1, PTL2, PTL3, PTL4, PTL5, PTL6, PTL7, PTL8, PTL9, PTL10, NPL6, NPL7, NPL8, NPL9, NPL10, PTL11, NPL11, NPL12, PTL12, PTL13, PTL14, PTL15, PTL16, PTL17, PTL18, PTL19, PTL20, PTL21, PTL22 and PTL23.

CITATION LIST

Patent Literature

{PTL 1} WO 2007/071035 A1
{PTL 2} WO 2006/024160 A1
{PTL 3} WO 2007/125398 A2
{PTL 4} WO 2007/002361 A2
{PTL 5} WO 2002/100833 A1
{PTL 18} WO 2007/110449 A1
{PTL 19} WO 2007/118854 A1
{PTL 20} WO 2008/008398 A2
{PTL 21} WO 2008/150447 A1
{PTL 22} WO 2008/150470 A1
{PTL 23} WO 2009/151152 A1
{PTL 24} U.S. Pat. No. 6,136,839 A

Non Patent Literature

{NPL 1} Davila, H. M., Annals of the New York Academy of Sciences, pp. 102-117 (1999)
{NPL 2} Hu et al., Bioorganic & Medicinal Chemistry 8:1203-1212 (200)
{NPL 3} Song et al., J. Med. Chem. 43:3474-3477 (2000)
{NPL 4} Wallace, M. S., The Clinical Journal of Pain 16:580-585 (2000)
{NPL 5} Vanegas, H. et al., Pain 85:9-18 (2000)
{NPL 6} Journal of Organic Chemistry 72(3): 1005-1008 (2007),
{NPL 7} European Journal of Pharmacology 563(1-3): 224-232 (2007),
{NPL 8} Current Opinion in Drug Discovery & Development 9(4): 516-524 (2006),
{NPL 9} Journal of Pharmacology and Experimental Therapeutics 317(1): 244-250 (2006), {NPL 10} Biochemical and Biophysical Research Communications 339(4): 1217-1223 (2006)
{NPL 11} Journal of Medicinal Chemistry 49(4): 1388-1396 (2006),
{NPL 12} Molecular Pharmacology 4(1): 44-52 (1968)
{NPL 13} Design of Prodrugs, H. Bundgaard ed., Elsevier (1985)
{NPL 14} "Drug and Enzyme Targeting, Part A," K. Widder et al. eds., Vol. 112 in Methods in Enzymology, Academic Press (1985)
{NPL 15} Bundgaard, "Design and Application of Prodrugs," Chapter 5 (pp. 113-191) in A Textbook of Drug Design and Development, P. Krogsgaard-Larsen and H. Bundgaard eds., Harwood Academic Publishers (1991)
{NPL 16} Bundgaard et al., Adv. Drug Delivery Revs. 8:1-38 (1992)
{NPL 17} Bundgaard et al., J. Pharmaceut. Sci. 77:285 (1988)
{NPL 18} Kakeya et al., Chem. Pharm. Bull. 32:692 (1984)
{NPL 19} Filer, Isotopes in the Physical and Biomedical Sciences, Vol. 1, Labeled Compounds (Part A), Chapter 6 (1987)
{NPL 20} M. Caira et al., J. Pharmaceut. Sci., 93(3):601-611 (2004)
{NPL 21} E. C. van Tonder et al., AAPS Pharm. Sci. Tech., 5(1):Article 12 (2004)
{NPL 22} A. L. Bingham et al., Chem. Commun.: 603-604 (2001)
{NPL 23} Brower, Nature Biotechnology 2000; 18: 387-391
{NPL 24} Levine, Inflammatory Pain, In: Textbook of Pain, Wall and Melzack eds., $3^{rd}$ ed., 1994
{NPL 25} Proc. Natl. Acad. Sci. U.S.A 89: 5058-5062 (1992)
{NPL 26} FEBS Lett. 291: 253-258 (1991)
{NPL 27} J. Biol. Chem. 268: 12359-12366 (1993)
{NPL 28} Proc. Natl. Acad. Sci. U.S.A. 89: 3251-3255 (1992)
{NPL 29} J. Biol. Chem. 265: 17786-17791 (1990)
{NPL 30} Neuron 18: 153-166 (1997)
{NPL 31} Hamill et al., Pfluegers Arch. 391: 85-100 (1981)
{NPL 32} Hunskaar, S., O. B. Fasmer, and K. Hole, J. Neurosci. Methods 14: 69-76 (1985)
{NPL 33} Kim and Chung, Pain 50: 355-363 (1992)
{NPL 34} Biochemistry & Behavior 31: 451-455 (1988)
{NPL 35} Paul A. Insel, Analgesic Antipyretic and Anti-inflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996)
{NPL 36} Glen R. Hanson, Analgesic, Antipyretic and Anti Inflammatory Drugs in Remington: The Science and Practice of Pharmacy Vol II 1196-1221 (A. R. Gennaro ed. 19th ed. 1995)

SUMMARY OF INVENTION

The present invention is related to acrylamide compounds represented by Formula I below, and the pharmaceutically acceptable salts and solvates thereof, and the use of these compounds as blockers of calcium ($Ca^{2+}$) channels. Certain compounds of Formula I show selectivity as N-type calcium channel blockers.

The invention is also related to treating or preventing a disorder responsive to the blockade of calcium channels in a mammal suffering from excess activity of said channels by administering an effective amount of a compound of Formula I, or a pharmaceutically acceptable salt or a solvate thereof, as described herein. Specifically, the invention is related to treating or preventing a disorder responsive to the blockade of N-type calcium channels in a mammal suffering from excess activity of said channels by administering an effective amount of a compound of Formula I, or a pharmaceutically acceptable salt or a solvate thereof, as described herein.

One aspect of the present invention is directed to novel compounds of Formula I and their pharmaceutically acceptable salts and solvates.

Another aspect of the present invention is directed to the use of the novel compounds of Formula I, and their pharmaceutically acceptable salts and solvates as blockers of N-type calcium channels.

A further aspect of the present invention is to provide a pharmaceutical composition useful for treating or preventing a disorder responsive to the blockade of calcium ion channels, especially N-type calcium ion channels, said pharmaceutical composition containing an effective amount of at least one compound of Formula I, or a pharmaceutically acceptable salt or a solvate thereof, in a mixture with one or more pharmaceutically acceptable carriers.

Also, an aspect of the invention is to provide a method for treating or preventing a disorder responsive to the blockade of calcium ion channels, especially N-type calcium ion channels, in a mammal, wherein said method comprises administering to the mammal an effective amount of at least one compound of Formula I, or a pharmaceutically acceptable salt or a solvate thereof.

Also, an aspect of the invention is to provide use of a compound of Formula I, or a pharmaceutically acceptable salt, or a solvate thereof in the manufacture of a medicament for treating or preventing a disorder responsive to the blockade of calcium ion channels, especially N-type calcium channels, in a mammal.

Also, an aspect of the invention is to provide a compound of Formula I, or a pharmaceutically acceptable salt or a solvate thereof, for use in a method for treating or preventing a disorder responsive to the blockade of calcium ion channels, especially N-type calcium channels, in a mammal, wherein said method comprises administering to the mammal an effective amount of at least one compound of Formula I, or a pharmaceutically acceptable salt or a solvate thereof.

A further aspect of the invention is to provide a pharmaceutical composition useful for modulating calcium channels, especially N-type calcium channels, said pharmaceutical composition containing an effective amount of at least one compound of Formula I, or a pharmaceutically acceptable salt or a solvate thereof, in a mixture with one or more pharmaceutically acceptable carriers.

Also, an aspect of the invention is to provide a method of modulating calcium channels, especially N-type calcium channels, in a mammal, wherein said method comprises administering to the mammal an effective amount of at least one compound of Formula I, or a pharmaceutically acceptable salt or a solvate thereof.

Also, an aspect of the invention is to provide use of a compound of Formula I, or a pharmaceutically acceptable salt or a solvate thereof in the manufacture of a medicament for modulating calcium channels, especially N-type calcium channels, in a mammal.

Also, an aspect of the invention is to provide a compound of Formula I, or a pharmaceutically acceptable salt or a solvate thereof, for use in a method of modulating calcium channels, especially N-type calcium channels, in a mammal, wherein said method comprises administering to the mammal an effective amount of at least one compound of Formula I, or a pharmaceutically acceptable salt or a solvate thereof.

A further aspect of the present invention is to provide a pharmaceutical composition useful for treating or preventing stroke, neuronal damage resulting from head trauma, epilepsy, pain (e.g., acute pain, chronic pain, which includes but is not limited to, neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, said pharmaceutical composition containing an effective amount of at least one compound of Formula I, or a pharmaceutically acceptable salt or a solvate thereof, in a mixture with one or more pharmaceutically acceptable carriers.

Also, an aspect of the invention is to provide a method for treating or preventing stroke, neuronal damage resulting from head trauma, epilepsy, pain (e.g., acute pain, chronic pain, which includes but is not limited to, neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, wherein said method comprises administering to the mammal an effective amount of at least one compound of Formula I, or a pharmaceutically acceptable salt or a solvate thereof.

Also, an aspect of the invention is to provide use of a compound of Formula I, or a pharmaceutically acceptable salt or a solvate thereof in the manufacture of a medicament for treating or preventing stroke, neuronal damage resulting from head trauma, epilepsy, pain (e.g., acute pain, chronic pain, which includes but is not limited to, neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia in a mammal.

A further aspect of the invention is to provide a compound of Formula I, or a pharmaceutically acceptable salt or a solvate thereof, for use in a method for treating or preventing stroke, neuronal damage resulting from head trauma, epilepsy, pain (e.g., acute pain, chronic pain, which includes but is not limited to, neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, wrein said method comprises administering to the mammal an effective amount of at least one compound of Formula I, or a pharmaceutically acceptable salt or a solvate thereof.

A further aspect of the present invention is to provide radiolabeled compounds of Formula I and the use of such compounds, or their pharmaceutically acceptable salts or solvates, as radioligands for their binding site on the calcium channel.

A further aspect of the invention is to provide a method for screening a candidate compound for the ability to bind to a binding site on a protein using a $^3$H, $^{11}$C or $^{14}$C radiolabeled compound of Formula I, or a pharmaceutically acceptable salt or a solvate thereof. This method comprises a) introducing a fixed concentration of the radiolabeled compound to a soluble or membrane-associated protein or fragment thereof to form a mixture; b) titrating the mixture with a candidate compound; and c) determining the binding of the candidate compound to said binding site.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention, as claimed.

DESCRIPTION OF EMBODIMENTS

One aspect of the present invention is based on the use of compounds of Formula I, and the pharmaceutically acceptable salts and solvates thereof, as blockers of $Ca^{2+}$ channels. In view of this property, compounds of Formula I, the pharmaceutically acceptable salts and solvates thereof, are useful for treating or preventing disorders responsive to the blockade of calcium ion channels. In one aspect, compounds of Formula I, the pharmaceutically acceptable salts and solvates thereof, selectively block N-type calcium ion channels and, thus, are useful for treating or preventing disorders responsive to the selective blockade of N-type calcium ion channels.

The present invention provides 1) a compound having Formula I:

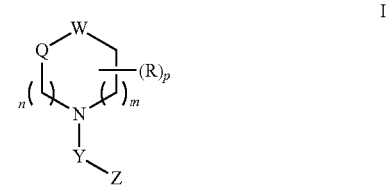

a pharmaceutically acceptable salt or a solvate thereof, wherein:

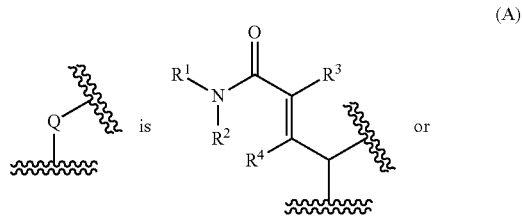

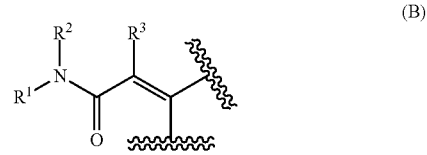

$R^1$ and $R^2$ are each independently hydrogen, cyano, optionally substituted alkyl, optionally substituted alkenyl, optionally substituted alkynyl, optionally substituted alkoxy, optionally substituted alkenyloxy, optionally substituted alkoxycarbonyl, optionally substituted acyl, optionally substituted cycloalkyl, optionally substituted cycloalkenyl, optionally substituted aryl, optionally substituted heterocyclyl, optionally substituted cycloalkyloxy, optionally substituted cycloalkenyloxy, optionally substituted aryloxy, or optionally substituted heterocyclyloxy, or $R^1$ and $R^2$ together with the adjacent nitrogen atom form an optionally substituted ring;

$R^3$ and $R^4$ are each independently hydrogen, halogen, optionally substituted alkyl or optionally substituted alkoxy;

W is —C($R^5$)($R^6$)— or —O—;

$R^5$ and $R^6$ are each independently hydrogen, alkyl, hydroxyalkyl, alkoxyalkyl, carboxy, alkoxycarbonyl, carbamoyl or alkylcarbamoyl;

Y is —S(O)$_2$— or —C($R^7$)($R^8$)—;

$R^7$ and $R^8$ are each independently hydrogen, cyano, optionally substituted alkyl, optionally substituted alkenyl, optionally substituted alkynyl, optionally substituted cycloalkyl, optionally substituted cycloalkenyl, optionally substituted aryl, or optionally substituted heterocyclyl, or $R^7$ and $R^8$ together with the adjacent carbon atom form an optionally substituted ring;

Z is optionally substituted cycloalkyl, optionally substituted cycloalkenyl, optionally substituted aryl or optionally substituted heterocyclyl;

R is alkyl, hydroxyalkyl, alkoxyalkyl, carboxy, alkoxycarbonyl, carbamoyl or alkylcarbamoyl;

m is 0 or 1;

n is 1 or 2; and p is 0 to 2, excluding i) compounds wherein Y is —CH$_2$— or —CH(CH$_3$)— and Z is unsubstituted phenyl, and ii) compounds wherein Q is (B) and $R^2$ is N-containing heterocyclyl substituted by fluoronaphtylmethyl;

2) the compound of the above 1), a pharmaceutically acceptable salt or a solvate thereof, wherein Q is (A), W is —C($R^5$)($R^6$)—, n is 2 and m is 0;

3) the compound of the above 1), a pharmaceutically acceptable salt or a solvate thereof, wherein Q is (A), W is —O—, n and m are simultaneously 1;

4) the compound of the above 2) or 3), a pharmaceutically acceptable salt or a solvate thereof, wherein Y is —S(O)$_2$—;

5) the compound of the above 1), a pharmaceutically acceptable salt or a solvate thereof, wherein Q is (B), n is 2, m is 0, and W is —C($R^5$)($R^6$)—;

6) the compound of the above 5), a pharmaceutically acceptable salt or a solvate thereof, wherein Y is —S(O)$_2$—;

7) the compound of any one of the above 1) to 6), a pharmaceutically acceptable salt or a solvate thereof, wherein Z is optionally substituted aryl;

8) the compound of the above 7), a pharmaceutically acceptable salt or a solvate thereof, wherein Z is optionally substituted phenyl;

9) the compound of any one of the above 1) to 8), a pharmaceutically acceptable salt or a solvate thereof, wherein $R^1$ is hydrogen or optionally substituted alkyl, and $R^2$ is optionally substituted alkyl, optionally substituted aryl or optionally substituted cycloalkyl;

10) the compound of any one of the above 1) to 9), a pharmaceutically acceptable salt or solvate thereof, wherein $R^3$ is hydrogen or optionally substituted alkoxy;

11) a pharmaceutical composition comprising a compound of any one of the above 1) to 10), a pharmaceutically acceptable salt or a solvate thereof and a pharmaceutically acceptable carrier;

12) the pharmaceutical composition of the above 11), which is used for treating or preventing a disorder responsive to the blockade of calcium channels;

13) the pharmaceutical composition of the above 11), which is used for treating or preventing stroke, neuronal damage resulting from head trauma, epilepsy, pain, migraine, a mood disorder, schizophrenia, a neurodegenerative disorder, depression, anxiety, a psychosis, hypertension or cardiac arrhythmia;

14) the pharmaceutical composition of the above 11), which is used for treating or preventing pain selected from chronic pain, acute pain, and surgical pain;

15) the pharmaceutical composition of the above 11), which is used for modulating calcium channels in a mammal;

16) a method of treating or preventing a disorder responsive to the blockade of calcium channels in a mammal suffering from said disorder, comprising administering to a mammal in need of such treatment or prevention an effective amount of a compound of any one of the above 1) to 10), a pharmaceutically acceptable salt or a solvate thereof;

17) the method of the above 16), wherein a disorder responsive to the blockade of N-type calcium channels is treated or prevented;

18) a method for treating or preventing stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal, comprising administering an effective amount of a compound of any one of the above 1) to 10), a pharmaceutically acceptable salt or a solvate thereof;

19) the method of the above 18), wherein the method is for treating or preventing pain selected from chronic pain, acute pain, and surgical pain;

20) a method of modulating calcium channels in a mammal, comprising administering to the mammal at least one compound of any one of the above 1) to 10), a pharmaceutically acceptable salt or a solvate thereof;

21) the method of the above 20), wherein the N-type calcium channel is modulated;

22) a compound of any one of the above 1) to 10), a pharmaceutically acceptable salt or a solvate thereof, for use in a method for treating or preventing a disorder responsive to the blockade of calcium ion channels in a mammal;

23) a compound of any one of the above 1) to 10), a pharmaceutically acceptable salt or a solvate thereof, for use in a method for treating or preventing stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal;

24) a compound of any one of the above 1) to 10), a pharmaceutically acceptable salt or a solvate thereof, for use in a method for treating or preventing pain selected from chronic pain, acute pain, and surgical pain;

25) a compound of any one of the above 1) to 10), a pharmaceutically acceptable salt or a solvate thereof, for use in a method of modulating calcium channels, in a mammal;

26) use of a compound of any one of the above 1) to 10), a pharmaceutically acceptable salt or a solvate thereof, for manufacturing a medicament for treating or preventing a disorder responsive to the blockade of calcium ion channels in a mammal;

27) use of a compound of any one of the above 1) to 10), a pharmaceutically acceptable salt or a solvate thereof, for manufacturing a medicament for treating or preventing stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal;

28) use of a compound of any one of the above 1) to 10), a pharmaceutically acceptable salt or a solvate thereof, for manufacturing a medicament for treating or preventing pain selected from chronic pain, acute pain, and surgical pain; and.

29) use of a compound of any one of the above 1) to 10), a pharmaceutically acceptable salt or a solvate thereof, for manufacturing a medicament for modulating calcium channels, in a mammal.

In the present specification, the term "halogen" includes fluorine, chlorine, bromine and iodine. Fluorine or chlorine is preferable. The halogen parts of "haloalkyl", "haloalkoxy" and "haloacyl" are the same as the above "halogen".

The term "alkyl" includes straight or branched chain alkyl having 1 to 10 carbon atoms, for example, 1 to 6 carbon atoms, or 1 to 3 carbon atoms. For example, included are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

"Optionally substituted alkyl" is optionally substituted with one or more substituents which can be the same or different, each substituent being independently selected from the followings:

1) halogen,
2) hydroxy,
3) carboxy,
4) mercapto,
5) cyano,
6) alkoxy optionally substituted with one or more substituents which can be the same or different, each substituent being independently selected from Group A and Group C,
7) acyl optionally substituted with one or more substituents which can be the same or different, each substituent being independently selected from Group A, Group B and Group C,
8) acyloxy optionally substituted with one or more substituents which can be the same or different, each substituent being independently selected from Group A, Group B and Group C,
9) alkoxycarbonyl optionally substituted with one or more substituents which can be the same or different, each substituent being independently selected from Group A and Group C,
10) aryloxycarbonyl optionally substituted with one or more substituents which can be the same or different, each substituent being independently selected from Group A, Group B and Group C,
11) alkylthio optionally substituted with one or more substituents which can be the same or different, each substituent being independently selected from Group A and Group C,
12) alkylsulfonyl optionally substituted with one or more substituents which can be the same or different, each substituent being independently selected from the Group A and Group C,
13) amino optionally substituted with one or more substituents which can be the same or different, each substituent being independently selected from Group A, Group B and Group C,
14) imino optionally substituted with one or more substituents which can be the same or different, each substituent being independently selected from Group A, Group B and Group C,
15) carbamoyl optionally substituted with one or more substituents which can be the same or different, each substituent being independently selected from Group B and Group C,
16) carbamoyloxy optionally substituted with one or more substituents which can be the same or different, each substituent being independently selected from Group B and Group C,
17) thiocarbamoyl optionally substituted with one or more substituents which can be the same or different, each substituent being independently selected from Group B and Group C,
18) cycloalkyl optionally substituted with one or more substituents which can be the same or different, each substituent being independently selected from Group A, Group B and Group C,
19) cycloalkenyl optionally substituted with one or more substituents which can be the same or different, each substituent being independently selected from Group A, Group B and Group C,
20) aryl optionally substituted with one or more substituents which can be the same or different, each substituent being independently selected from Group A, Group B and Group C,
21) heterocyclyl optionally substituted with one or more substituents which can be the same or different, each substituent being independently selected from Group A, Group B, Group C and oxo,
22) aryloxy optionally substituted with one or more substituents which can be the same or different, each substituent being independently selected from Group A, Group B and Group C,
23) arylthio optionally substituted with one or more substituents which can be the same or different, each substituent being independently selected from Group A, Group B and Group C,
24) cycloalkylsulfonyl optionally substituted with one or more substituents which can be the same or different, each substituent being independently selected from Group A, Group B and Group C,
25) arylsulfonyl optionally substituted with one or more substituents which can be the same or different, each substituent being independently selected from Group A, Group B and Group C, and
26) heterocyclylsulfonyl optionally substituted with one or more substituents which can be the same or different, each substituent being independently selected from Group A, Group B, Group C, and oxo.

Group A includes hydroxy, halogen, cyano, alkoxy, haloalkoxy, hydroxyalkoxy, arylalkoxy, acyl, haloacyl, aminoacyl, acyloxy, carboxy, alkoxycarbonyl, carbamoyl, alkylcarbamoyl, and optionally substituted amino, wherein the optional substituents are selected from alkyl, hydroxyalkyl, alkoxyalkyl, acyl, cycloalkyl, aryl and heterocyclyl. Group B includes alkyl, haloalkyl, hydroxyalkyl, alkoxyalkyl, aminoalkyl, alkylamino, alkylaminoalkyl, arylalkyl and heterocyclylalkyl.

Group C includes optionally substituted cycloalkyl, optionally substituted cycloalkenyl, optionally substituted aryl, optionally substituted aryloxy and optionally substituted heterocyclyl, wherein the optional substituents are selected from Group A, Group B and oxo.

The alkyl parts of "alkoxy", "alkoxycarbonyl", "alkylsulfonyl", "alkylthio", "haloalkyl", "hydroxyalkyl", "aminoalkyl", "alkylamino", "alkylaminoalkyl", "arylalkyl", "haloalkoxy", "hydroxyalkoxy", "alkoxyalkyl", "aryalkoxy", "alkylcarbamoyl", "heterocyclylalkyl", and "alkylenedioxy" are as defined for "alkyl". The optional substituents in "optionally substituted alkoxy" and "optionally substituted alkoxycarbonyl" include those defined for "optionally substituted alkyl". The term "alkenyl" refers to straight or branched chain alkenyl of 2 to 10 carbon atoms, for example, 2 to 8 carbon atoms or 3 to 6 carbon atoms, having at least one double bond at any possible positions. Examples of alkenyl groups are vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like. The alkenyl parts of "alkenyloxy" is as defined for "alkenyl"

The optional substituents in "optionally substituted alkenyl" and "optionally substituted alkenyloxy" are those defined for "optionally substituted alkyl".

The term "alkynyl" refers to straight or branched chain alkynyl of 2 to 10 carbon atoms, for example, 2 to 8 carbon atoms or 3 to 6 carbon atoms having at least one triple bond at any possible positions. Furthermore, "alkynyl" can have at least one double bond at any possible positions. Examples for alkynyl groups are ethynyl, propynyl, butynyl, pentynyl, hexynyl, heptynyl, octynyl, nonynyl, decynyl and the like. Substituents for "optionally substituted alkynyl" are those defined for "optionally substituted alkyl".

The term "acyl" refers to (i) straight or branched chain aliphatic acyl having 1 to 10 carbon atoms, for example, 1 to 6 carbon atoms or 1 to 4 carbon atoms, (ii) cyclic aliphatic acyl having 4 to 9 carbon atoms, for example, 4 to 7 carbon atoms, (iii) aroyl and (iv) heterocyclylcarbonyl. Examples for acyl groups are formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl, pyridinecarbonyl, pyrimidinecarbonyl, piperidincarbonyl, piperazinocarbonyl, morpholinocarbonyl and the like.

The acyl part in "acyloxy", "haloacyl" and "aminoacyl" is that defined for "acyl". The optional substituents in "optionally substituted acyl" include those defined for "optionally substituted alkyl", and (ii) cyclic aliphatic acyl, (iii) aroyl and (iv) heterocyclylcarbonyl can be substituted with alkyl optionally substituted with one or more substituents selected from Group A and Group C.

The term "cycloalkyl" refers to a carbocycle having 3 to 8 carbon atoms, and includes cyclopropyl, cyclobutyl, cyclopentyl, cyclohexyl, cycloheptyl, cyclooctyl and the like. "Optionally substituted cycloalkyl" is optionally substituted with one or more substituents which can be the same or different, each substituent being independently selected from
1) alkyl optionally substituted with one or more substituents selected from Group A and Group C, and
2) the same as those defined for "optionally substituted alkyl".

The cycloalkyl part of "cycloalkyloxy" and "cycloalkylsulfonyl" is as defined for "cycloalkyl".

The term "cycloalkenyl" refers to a group having at least one double bond at any possible positions in the above defined "cycloalkyl". Examples are cyclopropenyl, cyclobutenyl, cyclopentenyl, cyclohexenyl and cyclohexadienyl.

The cycloalkenyl part in "cycloalkenyloxy" is as defined for "cycloalkenyl".

The optional substituents in "optionally substituted cycloalkyloxy", "optionally substituted cycloalkenyl", and "optionally substituted cycloalkenyloxy" are those defined for "optionally substituted cycloalkyl."

The term "alkylamino" includes mono-alkylamino and di-alkylamino. "Optionally substituted amino" is optionally substituted with one or more substituents which can be the same or different, each substituent being independently selected from
1) alkyl optionally substituted with one or more substituents selected from Group A and Group C, and
2) those defined for "optionally substituted alkyl".

The optional substituents in "Optionally substituted carbamoyl" are those defined for "optionally substituted amino."

The term "aryl" includes phenyl, naphthyl, anthryl, phenanthryl, indenyl and the like.

The aryl parts in "aryloxy", "aryloxycarbonyl", "arylthio", "arylsulfonyl", "arylalkyl", and "arylalkoxy" are those defined above for "aryl".

The terms "heterocyclyl" or "heterocycle" refer to a heterocyclic group containing at least one heteroatom arbitrarily selected from O, S and N. Examples for heterocyclyl are 5- or 6-membered heteroaryl groups, such as pyrrolyl, imidazolyl, pyrazolyl, pyridyl, pyridazinyl, pyrimidinyl, pyrazinyl, isoxazolyl, oxazolyl, oxadiazolyl, isothiazolyl, thiazolyl, thiadiazolyl, furyl and thienyl; fused heterocyclyl groups having two rings, such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, quinazolinyl, quinolyl, isoquinolyl, naphthyridinyl, dihydropyridyl, tetrahydroquinolyl and tetrahydrobenzothienyl; fused heterocyclyl groups having three rings such as carbazolyl, acridinyl, xanthenyl, phenothiazinyl, phenoxathiinyl, phenoxazinyl and dibenzofuryl; and non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

The heterocyclyl parts of "heterocyclylalkyl" and "heterocyclylsulfonyl" are those defined above for "heterocyclyl".

Examples of the optional substituents in "optionally substituted aryl", "optionally substituted phenyl", "optionally substituted heterocyclyl", "optionally substituted aryloxy" and "optionally substituted heterocyclyloxy" are selected from
1) the optional substituents defined above for "optionally substituted alkyl",
2) alkyl optionally substituted with one or more substituents selected from the Group A and Group C,
3) oxo, and
4) alkylenedioxy.

These substituents can be attached to one or more of any possible positions.

"N-containing non-aromatic heterocyclyl" in the phrase "N-containing non-aromatic heterocyclyl substituted by fluoronaphtylmethyl" includes

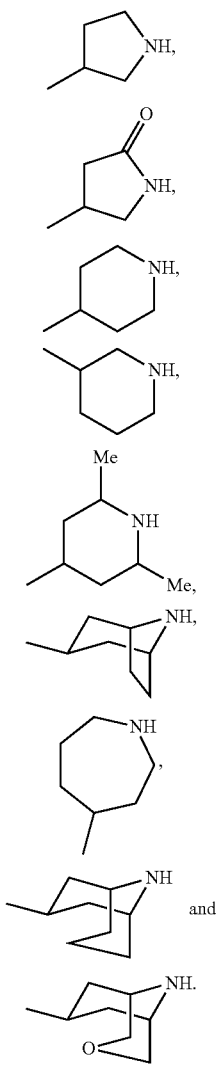

The ring in the phrase "R¹ and R² together with the adjacent nitrogen atom form an optionally substituted ring" includes a 3-8 membered saturated heterocycle which is optionally substituted and optionally contains additional one or more O, S and/or N. For example,

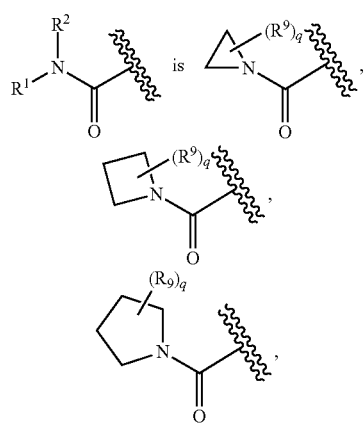

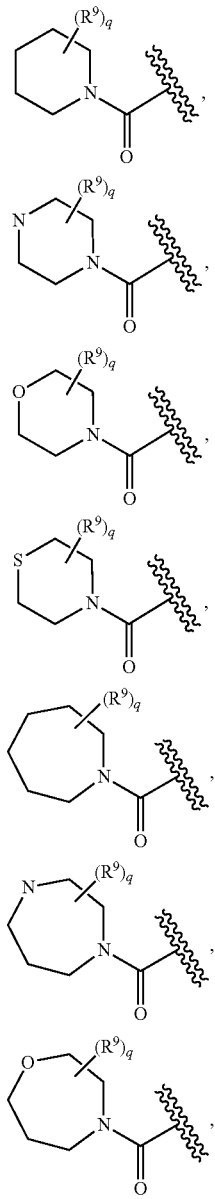

wherein $R^9$ is halogen, hydroxy, cyano, optionally substituted alkyl, optionally substituted alkoxy, optionally substituted alkenyl, optionally substituted alkynyl, carboxy, optionally substituted alkoxycarbonyl, optionally substituted acyl or optionally substituted amino, and q is 0, 1 or 2, and the like.

The ring in the phrase "$R^7$ and $R^8$ together with the adjacent carbon atom form an optionally substituted ring" includes a 3-8 membered saturated heterocycle, preferably a 3-6 membered saturated heterocycle which is optionally substituted and optionally contains additional one or more O, S and/or N. For example, —Y—Z is

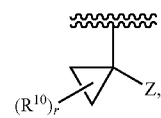

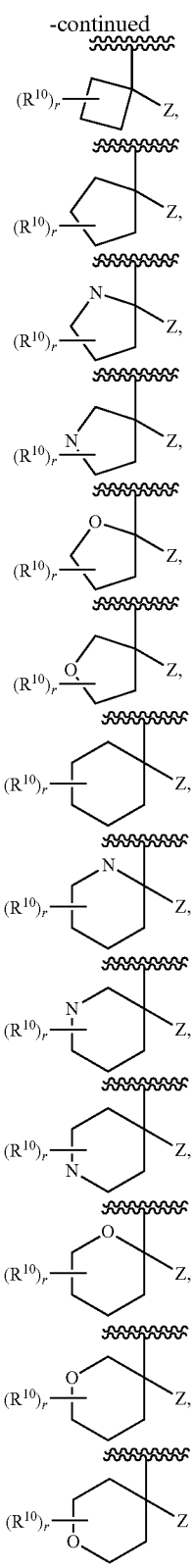

wherein $R^{10}$ is the same as $R^9$, r is 0, 1, or 2, and the like.

When p is 2, each R can be the same or different.

The compounds of the present invention encompass at least one double bond and can have an E or Z-stereochemistry at said double bond.

In one embodiment, preferable Acrylamide Compounds are the compounds of the following Formula IB:

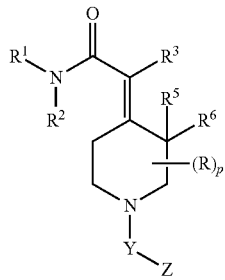

(IB)

wherein

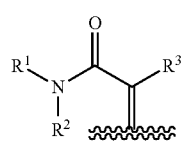

(herein after referred to as R1-3) is selected from the following:

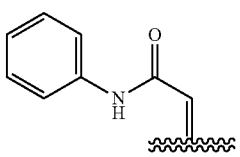

(R1-3a)

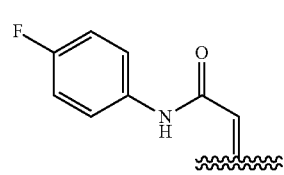

(R1-3b)

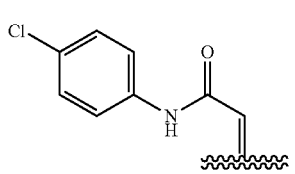

(R1-3c)

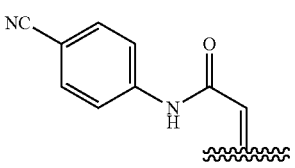

(R1-3d)

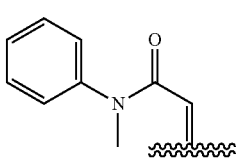

(R1-3e)

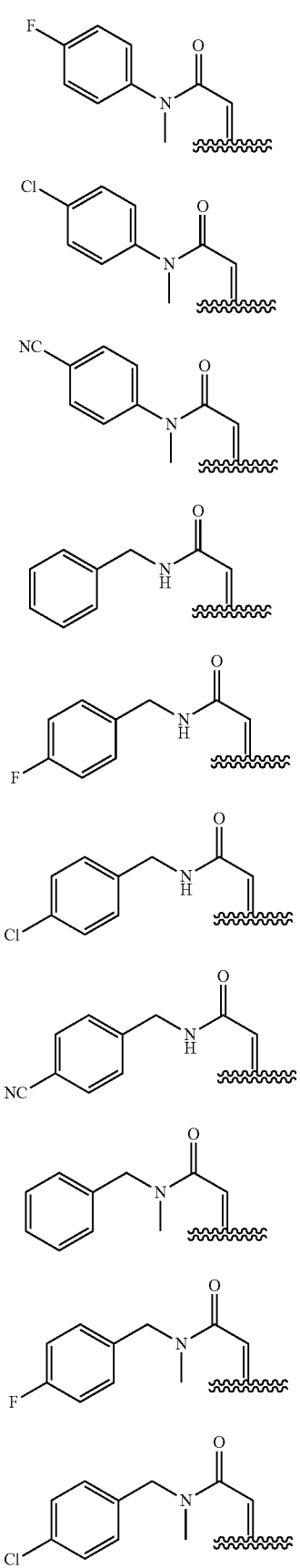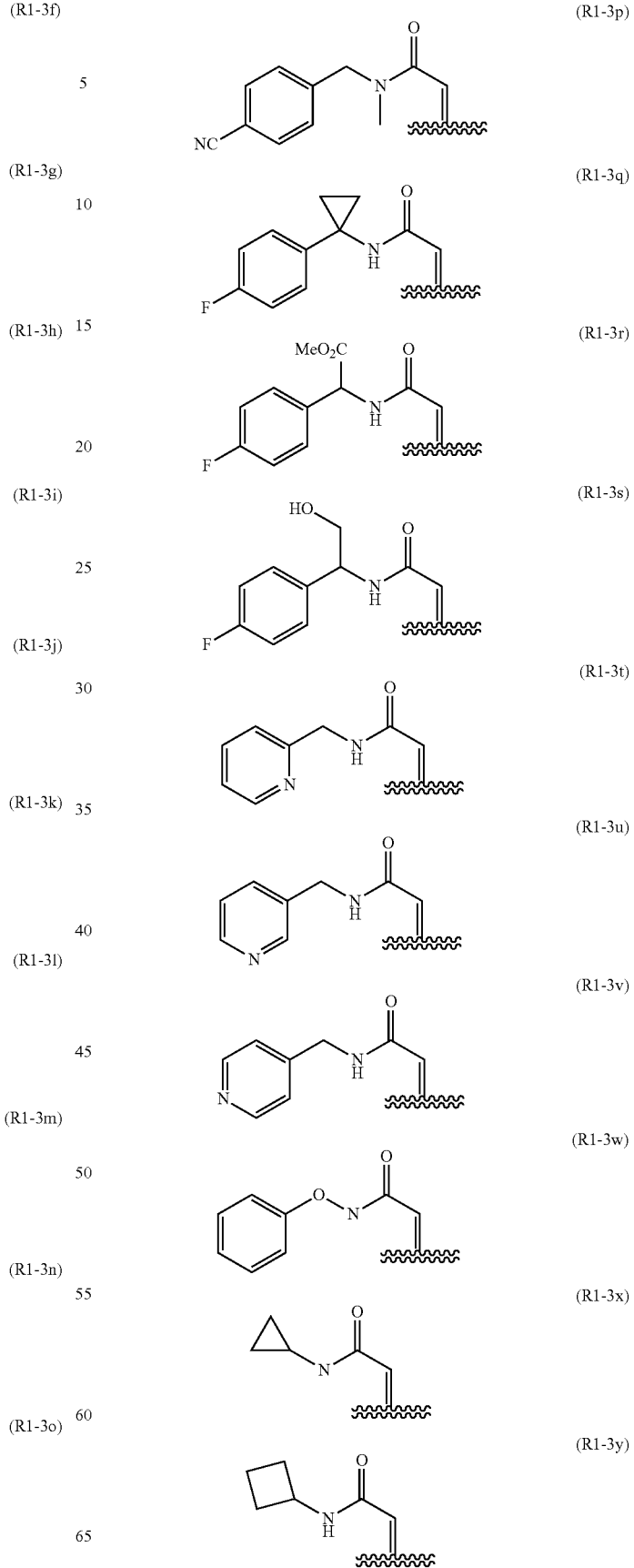

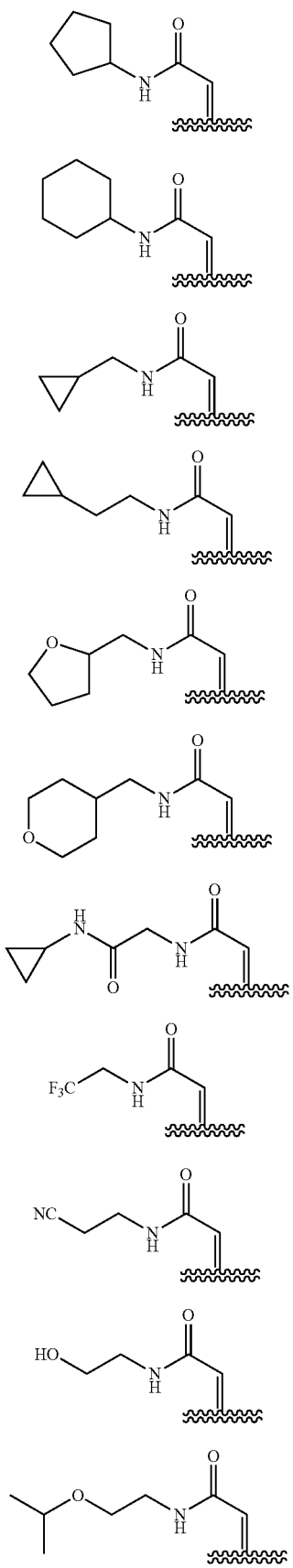
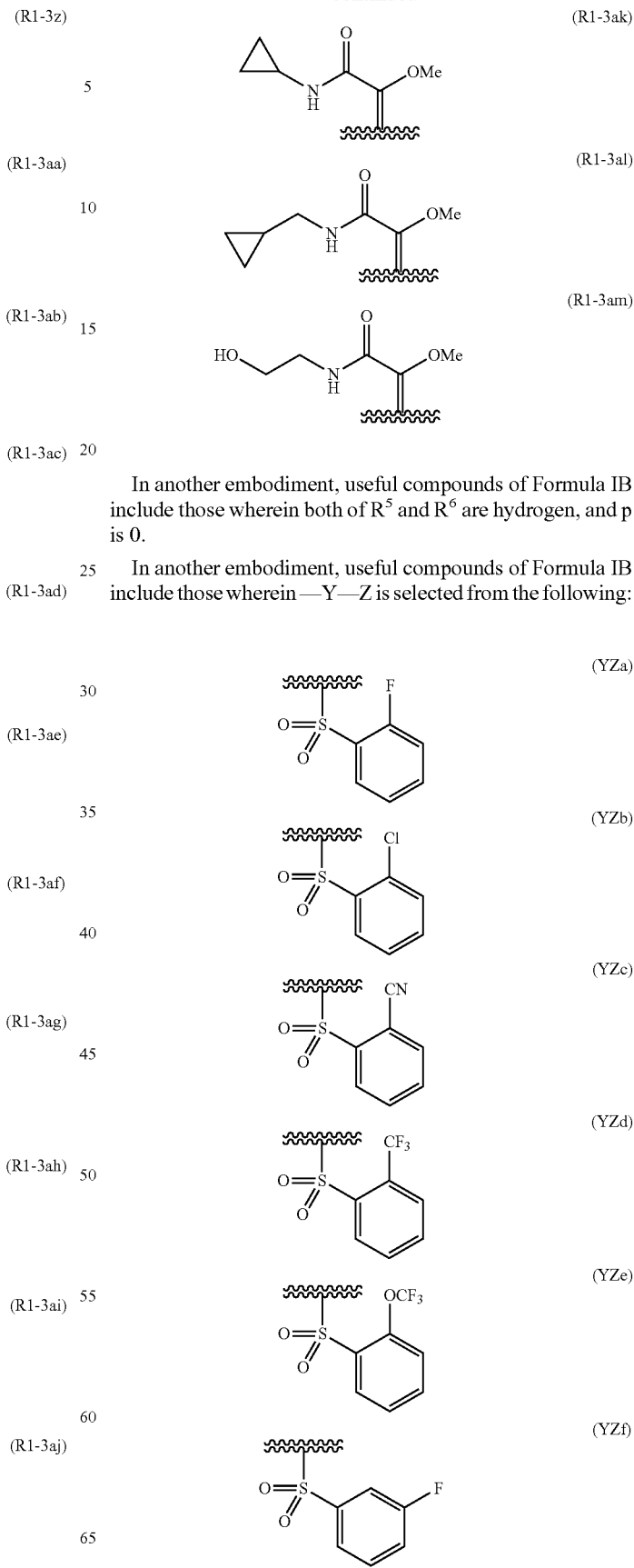
In another embodiment, useful compounds of Formula IB include those wherein both of $R^5$ and $R^6$ are hydrogen, and p is 0.
In another embodiment, useful compounds of Formula IB include those wherein —Y—Z is selected from the following:

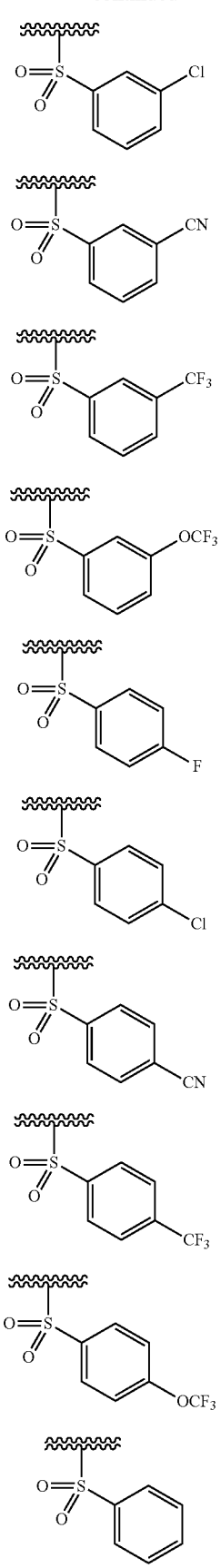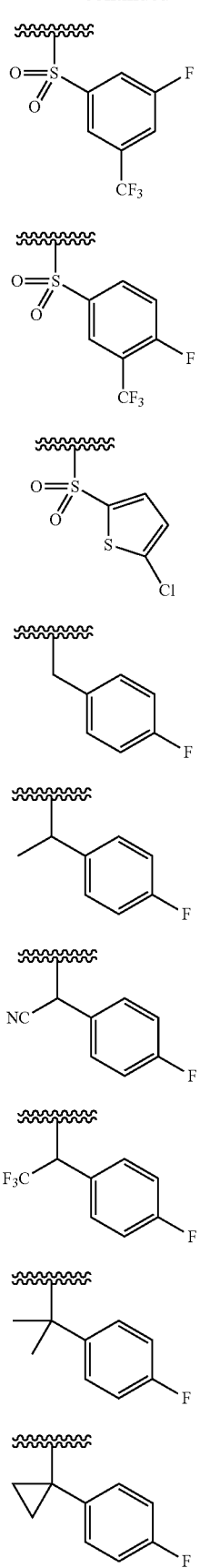

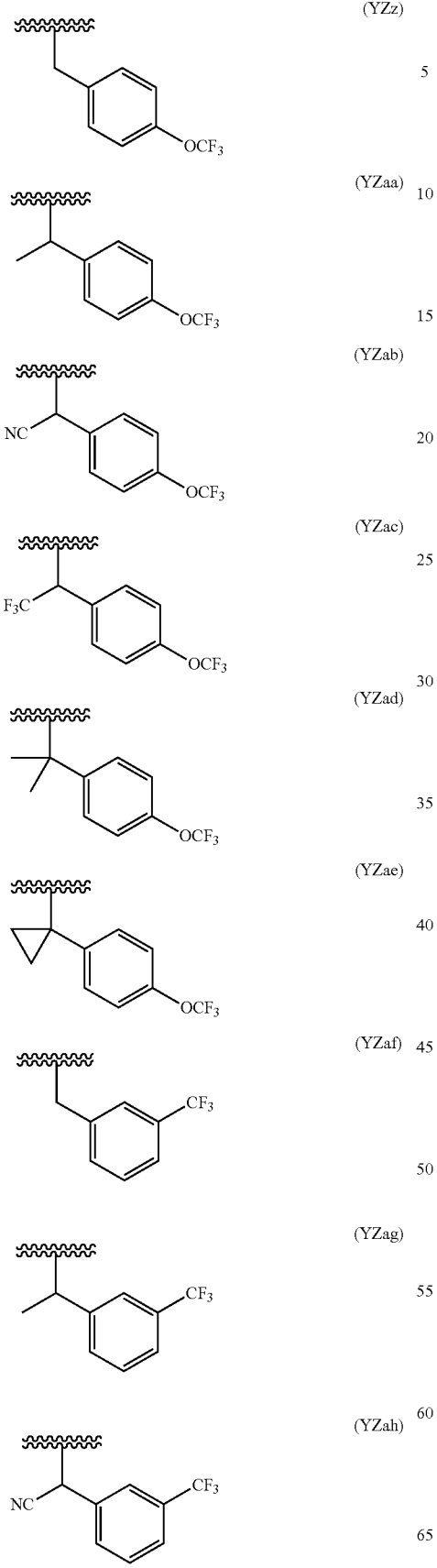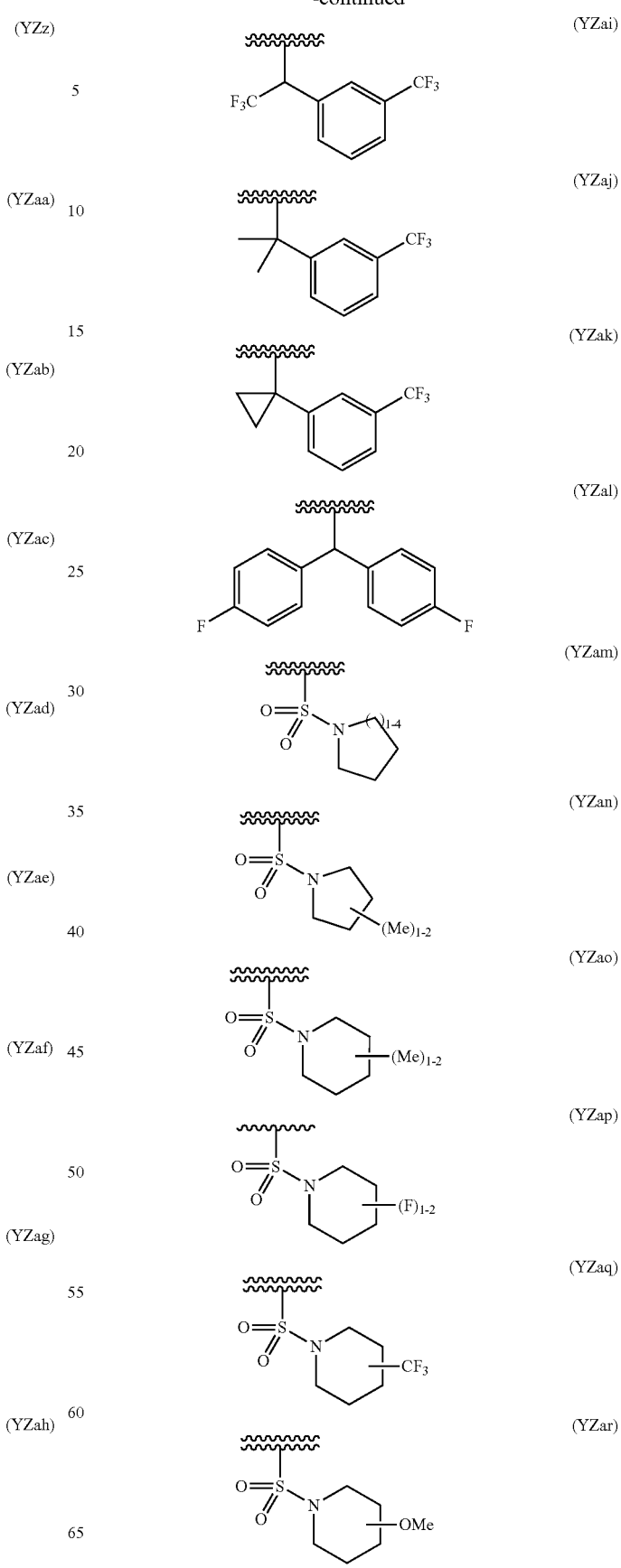

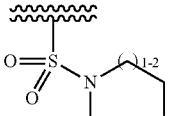
(YZas)

(YZat)

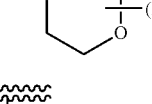
(YZau)

In another embodiment, useful compounds of Formula IB include those wherein both of $R^5$ and $R^6$ are hydrogen, p is 0 and the combination of R1-3 and Y—Z(=R1-3, —Y—Z) is as follows:
(Compound No. R1-3, —Y—Z)=(R1-3a,YZa), (R1-3a,YZb), (R1-3a,YZc), (R1-3a,YZd), (R1-3a,YZe), (R1-3a,YZf), (R1-3a,YZg), (R1-3a,YZh), (R1-3a,YZi), (R1-3a,YZj), (R1-3a,YZk), (R1-3a,YZl), (R1-3a,YZm), (R1-3a,YZn), (R1-3a,YZo), (R1-3a,YZp), (R1-3a,YZq), (R1-3a,YZr), (R1-3a,YZs), (R1-3a,YZt), (R1-3a,YZu), (R1-3a,YZv), (R1-3a,YZw), (R1-3a,YZx), (R1-3a,YZy), (R1-3a,YZz), (R1-3a,YZaa), (R1-3a,YZab), (R1-3a,YZac), (R1-3a,YZad), (R1-3a,YZae), (R1-3a,YZaf), (R1-3a,YZag), (R1-3a,YZah), (R1-3a,YZai), (R1-3a,YZaj), (R1-3a,YZak), (R1-3a,YZal), (R1-3a,YZam), (R1-3a,YZan), (R1-3a,YZao), (R1-3a,YZap), (R1-3a,YZaq), (R1-3a,YZar), (R1-3a,YZas), (R1-3a,YZat), (R1-3a,YZau), (R1-3b,YZa), (R1-3b,YZb), (R1-3b,YZc), (R1-3b,YZd), (R1-3b,YZe), (R1-3b,YZf), (R1-3b,YZg), (R1-3b,YZh), (R1-3b,YZi), (R1-3b,YZj), (R1-3b,YZk), (R1-3b,YZl), (R1-3b,YZm), (R1-3b,YZn), (R1-3b,YZo), (R1-3b,YZp), (R1-3b,YZq), (R1-3b,YZr), (R1-3b,YZs), (R1-3b,YZt), (R1-3b,YZu), (R1-3b,YZv), (R1-3b,YZw), (R1-3b,YZx), (R1-3b,YZy), (R1-3b,YZz), (R1-3b,YZaa), (R1-3b,YZab), (R1-3b,YZac), (R1-3b,YZad), (R1-3b,YZae), (R1-3b,YZaf), (R1-3b,YZag), (R1-3b,YZah), (R1-3b,YZai), (R1-3b,YZaj), (R1-3b,YZak), (R1-3b,YZal), (R1-3b,YZam), (R1-3b,YZan), (R1-3b,YZao), (R1-3b,YZap), (R1-3b,YZaq), (R1-3b,YZar), (R1-3b,YZas), (R1-3b,YZat), (R1-3b,YZau), (R1-3c,YZa), (R1-3c,YZb), (R1-3c,YZc), (R1-3c,YZd), (R1-3c,YZe), (R1-3c,YZf), (R1-3c,YZg), (R1-3c,YZh), (R1-3c,YZi), (R1-3c,YZj), (R1-3c,YZk), (R1-3c,YZl), (R1-3c,YZm), (R1-3c,YZn), (R1-3c,YZo), (R1-3c,YZp), (R1-3c,YZq), (R1-3c,YZr), (R1-3c,YZs), (R1-3c,YZt), (R1-3c,YZu), (R1-3c,YZv), (R1-3c,YZw), (R1-3c,YZx), (R1-3c,YZy), (R1-3c,YZz), (R1-3c,YZaa), (R1-3c,YZab), (R1-3c,YZac), (R1-3c,YZad), (R1-3c,YZae), (R1-3c,YZaf), (R1-3c,YZag), (R1-3c,YZah), (R1-3c,YZai), (R1-3c,YZaj), (R1-3c,YZak), (R1-3c,YZal), (R1-3c,YZam), (R1-3c,YZan), (R1-3c,YZao), (R1-3c,YZap), (R1-3c,YZaq), (R1-3c,YZar), (R1-3c,YZas), (R1-3c,YZat), (R1-3c,YZau), (R1-3d,YZa), (R1-3d,YZb), (R1-3d,YZc), (R1-3d,YZd), (R1-3d,YZe), (R1-3d,YZf), (R1-3d,YZg), (R1-3d,YZh), (R1-3d,YZi), (R1-3d,YZj), (R1-3d,YZk), (R1-3d,YZl), (R1-3d,YZm), (R1-3d,YZn), (R1-3d,YZo), (R1-3d,YZp), (R1-3d,YZq), (R1-3d,YZr), (R1-3d,YZs), (R1-3d,YZt), (R1-3d,YZu), (R1-3d,YZv), (R1-3d,YZw), (R1-3d,YZx), (R1-3d,YZy), (R1-3d,YZz), (R1-3d,YZaa), (R1-3d,YZab), (R1-3d,YZac), (R1-3d,YZad), (R1-3d,YZae), (R1-3d,YZaf), (R1-3d,YZag), (R1-3d,YZah), (R1-3d,YZai), (R1-3d,YZaj), (R1-3d,YZak), (R1-3d,YZal), (R1-3d,YZam), (R1-3d,YZan), (R1-3d,YZao), (R1-3d,YZap), (R1-3d,YZaq), (R1-3d,YZar), (R1-3d,YZas), (R1-3d,YZat), (R1-3d,YZau), (R1-3e,YZa), (R1-3e,YZb), (R1-3e,YZc), (R1-3e,YZd), (R1-3e,YZe), (R1-3e,YZf), (R1-3e,YZg), (R1-3e,YZh), (R1-3e,YZi), (R1-3e,YZj), (R1-3e,YZk), (R1-3e,YZl), (R1-3e,YZm), (R1-3e,YZn), (R1-3e,YZo), (R1-3e,YZp), (R1-3e,YZq), (R1-3e,YZr), (R1-3e,YZs), (R1-3e,YZt), (R1-3e,YZu), (R1-3e,YZv), (R1-3e,YZw), (R1-3e,YZx), (R1-3e,YZy), (R1-3e,YZz), (R1-3e,YZaa), (R1-3e,YZab), (R1-3e,YZac), (R1-3e,YZad), (R1-3e,YZae), (R1-3e,YZaf), (R1-3e,YZag), (R1-3e,YZah), (R1-3e,YZai), (R1-3e,YZaj), (R1-3e,YZak), (R1-3e,YZal), (R1-3e,YZam), (R1-3e,YZan), (R1-3e,YZao), (R1-3e,YZap), (R1-3e,YZaq), (R1-3e,YZar), (R1-3e,YZas), (R1-3e,YZat), (R1-3e,YZau), (R1-3f,YZa), (R1-3f,YZb), (R1-3f,YZc), (R1-3f,YZd), (R1-3f,YZe), (R1-3f,YZf), (R1-3f,YZg), (R1-3f,YZh), (R1-3f,YZi), (R1-3f,YZj), (R1-3f,YZk), (R1-3f,YZl), (R1-3f,YZm), (R1-3f,YZn), (R1-3f,YZo), (R1-3f,YZp), (R1-3f,YZq), (R1-3f,YZr), (R1-3f,YZs), (R1-3f,YZt), (R1-3f,YZu), (R1-3f,YZv), (R1-3f,YZw), (R1-3f,Ya), (R1-3f,YZy), (R1-3f,YZz), (R1-3f,YZaa), (R1-3f,YZab), (R1-3f,YZac), (R1-3f,YZad), (R1-3f,YZae), (R1-3f,YZaf), (R1-3f,YZag), (R1-3f,YZah), (R1-3f,YZai), (R1-3f,YZaj), (R1-3f,YZak), (R1-3f,YZal), (R1-3f,YZam), (R1-3f,YZan), (R1-3f,YZao), (R1-3f,YZap), (R1-3f,YZaq), (R1-3f,YZar), (R1-3f,YZas), (R1-3f,YZat), (R1-3f,YZau), (R1-3g,YZa), (R1-3g,YZb), (R1-3g,YZc), (R1-3g,YZd), (R1-3g,YZe), (R1-3g,YZf), (R1-3g,YZg), (R1-3g,YZh), (R1-3g,YZi), (R1-3g,YZj), (R1-3g,Ya), (R1-3g,YZl), (R1-3g,YZm), (R1-3g,YZn), (R1-3g,YZo), (R1-3g,YZp), (R1-3g,YZq), (R1-3g,YZr), (R1-3g,YZs), (R1-3g,YZt), (R1-3g,YZu), (R1-3g,YZv), (R1-3g,YZw), (R1-3g,YZx), (R1-3g,YZy), (R1-3g,YZz), (R1-3g,YZaa), (R1-3g,YZab), (R1-3g,YZac), (R1-3g,YZad), (R1-3g,YZae), (R1-3g,YZaf), (R1-3g,YZag), (R1-3g,YZah), (R1-3g,YZai), (R1-3g,YZaj), (R1-3g,YZak), (R1-3g,YZal), (R1-3g,YZam), (R1-3g,YZan), (R1-3g,YZao), (R1-3g,YZap), (R1-3g,YZaq), (R1-3g,YZar), (R1-3g,YZas), (R1-3g,YZat), (R1-3g,YZau), (R1-3h,YZa), (R1-3h,YZb), (R1-3h,YZc), (R1-3h,YZd), (R1-3h,YZe), (R1-3h,YZf), (R1-3h,YZg), (R1-3h,YZh), (R1-3h,YZi), (R1-3h,YZj), (R1-3h,YZk), (R1-3h,YZl), (R1-3h,YZm), (R1-3h,YZn), (R1-3h,YZo), (R1-3h,YZp), (R1-3h,YZq), (R1-3h,YZr), (R1-3h,YZs), (R1-3h,YZt), (R1-3h,YZu), (R1-3h,YZv), (R1-3h,YZw), (R1-3h,YZx), (R1-3h,YZy), (R1-3h,YZz), (R1-3h,YZaa), (R1-3h,YZab), (R1-3h,YZac), (R1-3h,YZad), (R1-3h,YZae), (R1-3h,YZaf), (R1-3h,YZag), (R1-3h,YZah), (R1-3h,YZai), (R1-3h,YZaj), (R1-3h,YZak), (R1-3h,YZal), (R1-3h,YZam), (R1-3h,YZan), (R1-3h,YZao), (R1-3h,YZap), (R1-3h,YZaq), (R1-3h,YZar), (R1-3h,YZas), (R1-3h,YZat), (R1-3h,YZau), (R1-3i,YZa), (R1-3i,YZb), (R1-3i,YZc), (R1-3i,YZd), (R1-3i,YZe), (R1-3i,YZf), (R1-3i,YZg), (R1-3i,YZh), (R1-3i,YZi), (R1-3i,YZj), (R1-3i,Ya), (R1-3i,YZl), (R1-3i,YZm), (R1-3i,YZn), (R1-3i,YZo), (R1-3i,YZp), (R1-3i,YZq), (R1-3i,YZr), (R1-3i,YZs), (R1-3i,YZt), (R1-3i,YZu), (R1-3i,YZv), (R1-3i,YZw), (R1-3i,YZx), (R1-3i,YZy), (R1-3i,YZz), (R1-3l,YZaa), (R1-3i,YZab), (R1-3i,YZac), (R1-3i,YZad), (R1-3i,YZae), (R1-3i,YZaf), (R1-3i,YZag), (R1-3i,YZah), (R1-3i,YZai), (R1-3i,YZaj), (R1-3i,YZak), (R1-3i,YZal), (R1-3i,YZam), (R1-3i,YZan), (R1-3i,YZao), (R1-3i,YZap), (R1-3i,YZaq), (R1-3i,YZar), (R1-3i,YZas), (R1-3i,YZat), (R1-3i,YZau), (R1-3j,YZa), (R1-3j,YZb), (R1-3j,YZc), (R1-3j,YZd), (R1-3j,YZe), (R1-3j,YZf), (R1-3j,YZg), (R1-3j,YZh), (R1-3j,YZi), (R1-3j,YZj), (R1-3j,YZk), (R1-3j,YZl), (R1-3j,YZm), (R1-3j,YZn), (R1-3j,YZo), (R1-3j,YZp), (R1-3j,YZq), (R1-3j,YZr), (R1-3j,YZs), (R1-3j,YZt), (R1-3j,YZu), (R1-3j,YZv), (R1-3j,YZw), (R1-3j,YZx), (R1-3j,YZy), (R1-3j,YZz), (R1-3j,YZaa), (R1-3j,YZab), (R1-3j,YZac), (R1-3j,YZad), (R1-3j,YZae), (R1-3j,YZaf), (R1-3j,YZag), (R1-3j,YZah), (R1-3j,YZai), (R1-3j,YZaj), (R1-3j,YZak), (R1-3j,YZal), (R1-3j,YZam), (R1-3j,YZan), (R1-3j,YZao), (R1-3j,YZap), (R1-3j,YZaq), (R1-3j,YZar), (R1-3j,YZas), (R1-3j,YZat), (R1-3j,YZau), (R1-3k,YZa), (R1-3k,YZb), (R1-3k,YZc), (R1-3k,YZd), (R1-3k,YZe), (R1-3k,YZf), (R1-3k,YZg), (R1-3k,YZh), (R1-3k,YZi), (R1-3k,YZj), (R1-3k,YZk), (R1-3k,YZl), (R1-3k,YZm), (R1-3k,YZn), (R1-3k,YZo), (R1-3k,YZp), (R1-3k,YZq), (R1-3k,YZr), (R1-3k,YZs), (R1-3k,YZt), (R1-3k,YZu), (R1-3k,YZv), (R1-3k,YZw), (R1-3k,YZx), (R1-3k,YZy), (R1-3k,YZz), (R1-3k,YZaa), (R1-3k,YZab), (R1-3k,YZac), (R1-3k,YZad), (R1-3k,YZae), (R1-3k,YZaf), (R1-3k,YZag), (R1-3k,YZah), (R1-3k,YZai), (R1-3k,YZaj), (R1-3k,YZak), (R1-3k,YZal), (R1-3k,YZam), (R1-3k,YZan), (R1-3k,YZao), (R1-3k,YZap), (R1-3k,YZaq), (R1-3k,YZar), (R1-3k,YZas), (R1-3k,YZat), (R1-3k,YZau), (R1-3l,YZa), (R1-3l,YZb), (R1-3l,YZc), (R1-3l,YZd), (R1-3l,YZe), (R1-3l,YZf, (R1-3l,YZg), (R1-3l,YZh), (R1-3l,YZi), (R1-3l,YZj), (R1-3l,YZk), (R1-3l,YZl), (R1-3l,YZm), (R1-3l,YZn), (R1-3l,YZo), (R1-3l,YZp), (R1-3l,YZq), (R1-3l,YZr), (R1-3l,YZs), (R1-3l,YZt), (R1-3l,YZu), (R1-3l,YZv), (R1-3l,YZw), (R1-3l,YZx), (R1-3l,YZy), (R1-3l,YZz), (R1-3l,YZaa), (R1-3l,YZab), (R1-3l,YZac), (R1-3l,YZad), (R1-3l,YZae), (R1-3l,YZaf), (R1-3l,YZag), (R1-3l,YZah), (R1-3l,YZai), (R1-3l,YZaj), (R1-3l,YZak), (R1-3l,YZal), (R1-3l,YZam), (R1-3l,YZan), (R1-3l,YZao), (R1-3l,YZap), (R1-3l,YZaq), (R1-3l,YZar), (R1-3l,YZas), (R1-3l,YZat), (R1-3l,YZau), (R1-3m,YZa), (R1-3m,YZb), (R1-3m,YZc), (R1-3m,YZd), (R1-3m,YZe), (R1-3m,YZf), (R1-3m,YZg), (R1-3m,YZh), (R1-3m,YZi), (R1-3m,YZj), (R1-3m,YZk), (R1-3m,YZl), (R1-3m,YZm), (R1-3m,YZn), (R1-3m,YZo), (R1-3m,YZp), (R1-3m,YZq), (R1-3m,YZr), (R1-3m,YZs), (R1-3m,YZt), (R1-3m,YZu), (R1-3 m,YZv), (R1-3m,YZw), (R1-3m,YZx), (R1-3m,YZy), (R1-3m,YZz), (R1-3m,YZaa), (R1-3m,YZab), (R1-3m,YZac), (R1-3m,YZad), (R1-3m,YZae), (R1-3m,YZat), (R1-3m,YZag), (R1-3m,YZah), (R1-3m,YZai), (R1-3m,YZaj), (R1-3m,YZak), (R1-3m,YZal), (R1-3m,YZam), (R1-3m,YZan), (R1-3m,YZao), (R1-3m,YZap), (R1-3m,YZaq), (R1-3m,YZar), (R1-3m,YZas), (R1-3m,YZat), (R1-3m,YZau), (R1-3n,YZa), (R1-3n,YZb), (R1-3n,YZc), (R1-3n,YZd), (R1-3n,YZe), (R1-3n,YZf), (R1-3n,YZg), (R1-3n,YZh), (R1-3n,YZi), (R1-3n,YZj), (R1-3n,YZk), (R1-3n,YZl), (R1-3n,YZm), (R1-3n,YZn), (R1-3n,YZo), (R1-3n,YZp), (R1-3n,YZq), (R1-3n,YZr), (R1-3n,YZs), (R1-3n,YZt), (R1-3n,YZu), (R1-3n,YZv), (R1-3n,YZw), (R1-3n,YZx), (R1-3n,YZy), (R1-3n,YZz), (R1-3n,YZaa), (R1-3n,YZab), (R1-3n,YZac), (R1-3n,YZad), (R1-3n,YZae), (R1-3n,YZaf), (R1-3n,YZag), (R1-3n,YZah), (R1-3n,YZai), (R1-3n,YZaj), (R1-3n,YZak), (R1-3n,YZal), (R1-3n,YZam), (R1-3n,YZan), (R1-3n,YZao), (R1-3n,YZap), (R1-3n,YZaq), (R1-3n,YZar), (R1-3n,YZas), (R1-3n,YZat), (R1-3n,YZau), (R1-3o,YZa), (R1-3o,YZb), (R1-3o,YZc), (R1-3o,YZd), (R1-3o,YZe), (R1-3o,YZf), (R1-3o,YZg), (R1-3o,YZh), (R1-3o,YZi), (R1-3o,YZj), (R1-3o,YZk), (R1-3o,YZl), (R1-3o,YZm), (R1-3o,YZn), (R1-3o,YZo), (R1-3o,YZp), (R1-3o,YZq), (R1-3o,YZr), (R1-3o,YZs), (R1-3o,YZt), (R1-3o,YZu), (R1-3o,YZv), (R1-3o,YZw), (R1-3o,YZx), (R1-3o,YZy), (R1-3o,YZz), (R1-3o,YZaa), (R1-3o,YZab), (R1-3o,YZac), (R1-3o,YZad), (R1-3o,YZae), (R1-3o,YZaf), (R1-3o,YZag), (R1-3o,YZah), (R1-3o,YZai), (R1-3o,YZaj), (R1-3o,YZak), (R1-3o,YZal), (R1-3o,YZam), (R1-3o,YZan), (R1-3o,YZao), (R1-3o,YZap), (R1-3o,YZaq), (R1-3o,YZar), (R1-3o,YZas), (R1-3o,YZat), (R1-3o,YZau), (R1-3p,YZa), (R1-3p,YZb), (R1-3p,YZc), (R1-3p,YZd), (R1-3p,YZe), (R1-3p,YZf), (R1-3p,YZg), (R1-3p,YZh), (R1-3p,YZi), (R1-3p,YZj), (R1-3p,YZk), (R1-3p,YZl), (R1-3p,YZm), (R1-3p,YZn), (R1-3p,YZo), (R1-3p,YZp), (R1-3p,YZq), (R1-3p,YZr), (R1-3p,YZs), (R1-3p,YZt), (R1-3p,YZu), (R1-3p,YZv), (R1-3p,YZw), (R1-3p,YZx), (R1-3p,YZy), (R1-3p,YZz), (R1-3p,YZaa), (R1-3p,YZab), (R1-3p,YZac), (R1-3p,YZad), (R1-3p,YZae), (R1-3p,YZaf), (R1-3p,YZag), (R1-3p,YZah), (R1-3p,YZai), (R1-3p,YZaj), (R1-3p,YZak), (R1-3p,YZal), (R1-3p,YZam), (R1-3p,YZan), (R1-3p,YZao), (R1-3p,YZap), (R1-3p,YZaq), (R1-3p,YZar), (R1-3p,YZas), (R1-3p,YZat), (R1-3p,YZau), (R1-3q,YZa), (R1-3q,YZb), (R1-3q,YZc), (R1-3q,YZd), (R1-3q,YZe), (R1-3q,YZf), (R1-3q,YZg), (R1-3q,YZh), (R1-3q,YZi), (R1-3q,YZj), (R1-3q,YZk), (R1-3q,YZl), (R1-3q,YZm), (R1-3q,YZn), (R1-3q,YZo), (R1-3q,YZp), (R1-3q,YZq), (R1-3q,YZr), (R1-3q,YZs), (R1-3q,YZt), (R1-3q,YZu), (R1-3q,YZv), (R1-3q,YZw), (R1-3q,YZx), (R1-3q,YZy), (R1-3q,YZz), (R1-3q,YZaa), (R1-3q,YZab), (R1-3q,YZac), (R1-3q,YZad), (R1-3q,YZae), (R1-3q,YZaf), (R1-3q,YZag), (R1-3q,YZah), (R1-3q,YZai), (R1-3q,YZaj), (R1-3q,YZak), (R1-3q,YZal), (R1-3q,YZam), (R1-3q,YZan), (R1-3q,YZao), (R1-3q,YZap), (R1-3q,YZaq), (R1-3q,YZar), (R1-3q,YZas), (R1-3q,YZat), (R1-3q,YZau), (R1-3r,YZa), (R1-3r,YZb), (R1-3r,YZc), (R1-3r,YZd), (R1-3r,YZe), (R1-3r,YZf), (R1-3r,YZg), (R1-3r,YZh), (R1-3r,YZi), (R1-3r,YZj), (R1-3r,YZk), (R1-3r,YZl), (R1-3r,YZm), (R1-3r,YZn), (R1-3r,YZo), (R1-3r,YZp), (R1-3r,YZq), (R1-3r,YZr), (R1-3r,YZs), (R1-3r,YZt), (R1-3r,YZu), (R1-3r,YZv), (R1-3r,YZw), (R1-3r,YZx), (R1-3r,YZy), (R1-3r,YZz), (R1-3r,YZaa), (R1-3r,YZab), (R1-3r,YZac), (R1-3r,YZad), (R1-3r,YZae), (R1-3r,YZaf), (R1-3r,YZag), (R1-3r,YZah), (R1-3r,YZai), (R1-3r,YZaj), (R1-3r,YZak), (R1-3r,YZal), (R1-3r,YZam), (R1-3r,YZan), (R1-3r,YZao), (R1-3r,YZap), (R1-3r,YZaq), (R1-3r,YZar), ($R^1$-3r,YZas), (R1-3r,YZat), (R1-3r,YZau), (R1-3s,YZa), (R1-3s,YZb), (R1-3s,YZc), (R1-3s,YZd), (R1-3s,YZe), (R1-3s,YZf), (R1-3s,YZg), (R1-3s,YZh), (R1-3s,YZi), (R1-3s,YZj), (R1-3s,YZk), (R1-3s,YZl), (R1-3s,YZm), (R1-3s,YZn), (R1-3s,YZo), (R1-3s,YZp), (R1-3s,YZq), (R1-3s,YZr), (R1-3s,YZs), (R1-3s,YZt), (R1-3s,YZu), (R1-3s,YZv), (R1-3s,YZw), (R1-3s,YZx), (R1-3s,YZy), (R1-3s,YZz), (R1-3s,YZaa), (R1-3s,YZab), (R1-3s,YZac), (R1-3s,YZad), (R1-3s,YZae), (R1-3s,YZaf), (R1-3s,YZag), (R1-3s,YZah), (R1-3s,YZai), (R1-3s,YZaj), (R1-3s,YZak), (R1-3s,YZal), (R1-3s,YZam), (R1-3s,YZan), (R1-3s,YZao), (R1-3s,YZap), (R1-3s,YZaq), (R1-3s,YZar), (R1-3s,YZas), (R1-3s,YZat), (R1-3s,YZau), (R1-3t,YZa), (R1-3t,YZb), (R1-3t,YZc), (R1-3t,YZd), (R1-3t,YZe), (R1-3t,YZf), (R1-3t,YZg), (R1-3t,YZh), (R1-3t,YZi), (R1-3t,YZj), (R1-3t,YZk), (R1-3t,YZl), (R1-3t,YZm), (R1-3t,YZn), (R1-3t,YZo), (R1-3t,YZp), (R1-3t,YZq), (R1-3t,YZr), (R1-3t,YZs), (R1-3t,YZt), (R1-3t,YZu), (R1-3t,YZv), (R1-3t,YZw), (R1-3t,YZx), (R1-3t,YZy), (R1-3t,YZz), (R1-3t,YZaa), (R1-3t,YZab), (R1-3t,YZac), (R1-3t,YZad), (R1-3t,YZae), (R1-3t,YZaf), (R1-3t,YZag), (R1-3t,YZah), (R1-3t,YZai), (R1-3t,YZaj), (R1-3t,YZak), (R1-3t,YZal), (R1-3t,YZam), (R1-3t,YZan), (R1-3t,YZao), (R1-3t,YZap), (R1-3t,YZaq), (R1-3t,YZar), (R1-3t,YZas), (R1-3t,YZat), (R1-3t,YZau), (R1-3u,YZa), (R1-3u,YZb), (R1-3u,YZc), (R1-3u,YZd), (R1-3u,YZe), (R1-3u,YZf), (R1-3u,YZg), (R1-3u,YZh), (R1-3u,YZi), (R1-3u,YZj), (R1-3u,YZk), (R1-3u,YZl), (R1-3u,YZm), (R1-3u,YZn), (R1-3u,YZo), (R1-3u,YZp), (R1-3u,YZq), (R1-3u,YZr), (R1-3u,YZs), (R1-3u,YZt), (R1-3u,YZu), (R1-3u,YZv), (R1-3u,YZw), (R1-3u,YZx), (R1-3u,YZy), (R1-3u,YZz), (R1-3u, YZaa), (R1-3u,YZab), (R1-3u,YZac), (R1-3u,YZad), (R1-3u,YZae), (R1-3u,YZaf), (R1-3u,YZag), (R1-3u,YZah), (R1-3u,YZai), (R1-3u,YZaj), (R1-3u,YZak), (R1-3u,YZal), (R1-3u,YZam), (R1-3u,YZan), (R1-3u,YZao), (R1-3u,YZap), (R1-3u,YZaq), (R1-3u,YZar), (R1-3u,YZas), (R1-3u,YZat), (R1-3u,YZau), (R1-3v,YZa), (R1-3v,YZb), (R1-3v,YZc), (R1-3v,YZd), (R1-3v,YZe), (R1-3v,YZf), (R1-3v,YZg), (R1-3v,YZh), (R1-3v,YZi), (R1-3v,YZj), (R1-3v,YZk), (R1-3v,YZl), (R1-3v,YZm), (R1-3v,YZn), (R1-3v,YZo), (R1-3v,YZp), (R1-3v,YZq), (R1-3v,YZr), (R1-3v,YZs), (R1-3v,YZt), (R1-3v,YZu), (R1-3v,YZv), (R1-3v,YZw), (R1-3v,YZx), (R1-3v,YZy), (R1-3v,YZz), (R1-3v,YZaa), (R1-3v,YZab), (R1-3v,YZac), (R1-3v,YZad), (R1-3v,YZae), (R1-3v,YZaf), (R1-3v,YZag), (R1-3v,YZah), (R1-3v,YZai), (R1-3v,YZaj), (R1-3v,YZak), (R1-3v,YZal), (R1-3v,YZam), (R1-3v,YZan), (R1-3v,YZao), (R1-3v,YZap), (R1-3v,YZaq), (R1-3v,YZar), (R1-3v,YZas), (R1-3v,YZat), (R1-3v,YZau), (R1-3w,YZa), (R1-3w,YZb), (R1-3w,YZc), (R1-3w,YZd), (R1-3w,YZe), (R1-3w,YZf), (R1-3w,YZg), (R1-3w,YZh), (R1-3w,YZi), (R1-3w,YZj), (R1-3w,YZk), (R1-3w,YZl), (R1-3w,YZm), (R1-3w,YZn), (R1-3w,YZo), (R1-3w,YZp), (R1-3w,YZq), (R1-3w,YZr), (R1-3w,YZs), (R1-3w,YZt), (R1-3w,YZu), (R1-3w,YZv), (R1-3w,YZw), (R1-3w,YZx), (R1-3w,YZy), (R1-3w,YZz), (R1-3w,YZaa), (R1-3w,YZab), (R1-3w,YZac), (R1-3w,YZad), (R1-3w,YZae), (R1-3w,YZaf), (R1-3w,YZag), (R1-3w,YZah), (R1-3w,YZai), (R1-3w,YZaj), (R1-3w,YZak), (R1-3w,YZal), (R1-3w,YZam), (R1-3w,YZan), (R1-3w,YZao), (R1-3w,YZap), (R1-3w,YZaq), (R1-3w,YZar), (R1-3w,YZas), (R1-3w,YZat), (R1-3w,YZau), (R1-3x,YZa), (R1-3x,YZb), (R1-3x,YZc), (R1-3x,YZd), (R1-3x,YZe), (R1-3x,YZf), (R1-3x,YZg), (R1-3x,Ya), (R1-3x,YZi), (R1-3x,YZj), (R1-3x,YZk), (R1-3x,YZl), (R1-3x,YZm), (R1-3x,YZn), (R1-3x,YZo), (R1-3x,YZp), (R1-3x,YZq), (R1-3x,YZr), (R1-3x,YZs), (R1-3x,YZt), (R1-3x,YZu), (R1-3x,YZv), (R1-3x,YZw), (R1-3x,YZx), (R1-3x,YZy), (R1-3x,YZz), (R1-3x,YZaa), (R1-3x,YZab), (R1-3x,YZac), (R1-3x,YZad), (R1-3x,YZae), (R1-3x,YZaf), (R1-3x,YZag), (R1-3x,YZah), (R1-3x,YZai), (R1-3x,YZaj), (R1-3x,YZak), (R1-3x,YZal), (R1-3x,YZam), (R1-3x,YZan), (R1-3x,YZao), (R1-3x,YZap), (R1-3x,YZaq), (R1-3x,YZar), (R1-3x,YZas), (R1-3x,YZat), (R1-3x,YZau), (R1-3y,YZa), (R1-3y,YZb), (R1-3y,YZc), (R1-3y,YZd), (R1-3y,YZe), (R1-3y,YZf), (R1-3y,YZg), (R1-3y,YZh), (R1-3y,YZi), (R1-3y,YZj), (R1-3y,YZk), (R1-3y,YZl), (R1-3y,YZm), (R1-3y,YZn), (R1-3y,YZo), (R1-3y,YZp), (R1-3y,YZq), (R1-3y,YZr), (R1-3y,YZs), (R1-3y,YZt), (R1-3y,YZu), (R1-3y,YZv), (R1-3y,YZw), (R1-3y,YZx), (R1-3y,YZy), (R1-3y,YZz), (R1-3y,YZaa), (R1-3y,YZab), (R1-3y,YZac), (R1-3y,YZad), (R1-3y,YZae), (R1-3y,YZaf), (R1-3y,YZag), (R1-3y,YZah), (R1-3y,YZai), (R1-3y,YZaj), (R1-3y,YZak), (R1-3y,YZal), (R1-3y,YZam), (R1-3y,YZan), (R1-3y,YZao), (R1-3y,YZap), (R1-3y,YZaq), (R1-3y,YZar), (R1-3y,YZas), (R1-3y,YZat), (R1-3y,YZau), (R1-3z,YZa), (R1-3z,YZb), (R1-3z,YZc), (R1-3z,YZd), (R1-3z,YZe), (R1-3z,YZf), (R1-3z,YZg), (R1-3z,YZh), (R1-3z,YZi), (R1-3z,YZj), (R1-3z,YZk), (R1-3z,YZl), (R1-3z,YZm), (R1-3z,YZn), (R1-3z,YZo), (R1-3z,YZp), (R1-3z,YZq), (R1-3z,YZr), (R1-3z,YZs), (R1-3z,YZt), (R1-3z,YZu), (R1-3z,YZv), (R1-3z,YZw), (R1-3z,YZx), (R1-3z,YZy), (R1-3z,YZz), (R1-3z,YZaa), (R1-3z,YZab), (R1-3z,YZac), (R1-3z,YZad), (R1-3z,YZae), (R1-3z,YZaf), (R1-3z,YZag), (R1-3z,YZah), (R1-3z,YZai), (R1-3z,YZaj), (R1-3z,YZak), (R1-3z,YZal), (R1-3z,YZam), (R1-3z,YZan), (R1-3z,YZao), (R1-3z,YZap), (R1-3z,YZaq), (R1-3z,YZar), (R1-3z,YZas), (R1-3z,YZat), (R1-3z,YZau), (R1-3aa,YZa), (R1-3aa,YZb), (R1-3aa,YZc), (R1-3aa,YZd), (R1-3aa,YZe), (R1-3aa,YZf), (R1-3aa,YZg), (R1-3aa,YZh), (R1-3aa,YZi), (R1-3aa,YZj), (R1-3aa,YZk), (R1-3aa,YZl), (R1-3aa,YZm), (R1-3aa,YZn), (R1-3aa,YZo), (R1-3aa,YZp), (R1-3aa,YZq), (R1-3aa,YZr), (R1-3aa,YZs), (R1-3aa,YZt), (R1-3aa,YZu), (R1-3aa,YZv), (R1-3aa,YZw), (R1-3aa,YZx), (R1-3aa,YZy), (R1-3aa,YZz), (R1-3aa,YZaa), (R1-3aa,YZab), (R1-3aa,YZac), (R1-3aa,YZad), (R1-3aa,YZae), (R1-3aa,YZaf), (R1-3aa,YZag), (R1-3aa,YZah), (R1-3aa,YZai), (R1-3aa,YZaj), (R1-3aa,YZak), (R1-3aa,YZal), (R1-3aa,YZam), (R1-3aa,YZan), (R1-3aa,YZao), (R1-3aa,YZap), (R1-3aa,YZaq), (R1-3aa,YZar), (R1-3aa,YZas), (R1-3aa,YZat), (R1-3aa,YZau), (R1-3ab,YZa), (R1-3ab,YZb), (R1-3ab,YZc), (R1-3ab,YZd), (R1-3ab,YZe), (R1-3ab,YZf), (R1-3ab,YZg), (R1-3ab,YZh), (R1-3ab,YZi), (R1-3ab,YZj), (R1-3ab,YZk), (R1-3ab,YZl), (R1-3ab,YZm), (R1-3ab,YZn), (R1-3ab,YZo), (R1-3ab,YZp), (R1-3ab,YZq), (R1-3ab,YZr), (R1-3ab,YZs), (R1-3ab,YZt), (R1-3ab,YZu), (R1-3ab,YZv), (R1-3ab,YZw), (R1-3ab,YZx), (R1-3ab,YZy), (R1-3ab,YZz), (R1-3ab,YZaa), (R1-3ab,YZab), (R1-3ab,YZac), (R1-3ab,YZad), (R1-3ab,YZae), (R1-3ab,YZaf), (R1-3ab,YZag), (R1-3ab,YZah), (R1-3ab,YZai), (R1-3ab,YZaj), (R1-3ab,YZak), (R1-3ab,YZal), (R1-3ab,YZam), (R1-3ab,YZan), (R1-3ab,YZao), (R1-3ab,YZap), (R1-3ab,YZaq), (R1-3ab,YZar), (R1-3ab,YZas), (R1-3ab,YZat), (R1-3ab,YZau), (R1-3ac,YZa), (R1-3ac,YZb), (R1-3ac,YZc), (R1-3ac,YZd), (R1-3ac,YZe), (R1-3ac,YZf), (R1-3ac,YZg), (R1-3ac,YZh), (R1-3ac,YZi), (R1-3ac,YZj), (R1-3ac,YZk), (R1-3ac,YZl), (R1-3ac,YZm), (R1-3ac,YZn), (R1-3ac,YZo), (R1-3ac,YZp), (R1-3ac,YZq), (R1-3ac,YZr), (R1-3ac,YZs), (R1-3ac,YZt), (R1-3ac,YZu), (R1-3ac,YZv), (R1-3ac,YZw), (R1-3ac,YZx), (R1-3ac,YZy), (R1-3ac,YZz), (R1-3ac,YZaa), (R1-3ac,YZab), (R1-3ac,YZac), (R1-3ac,YZad), (R1-3ac,YZae), (R1-3ac,YZaf), (R1-3ac,YZag), (R1-3ac,YZah), (R1-3ac,YZai), (R1-3ac,YZaj), (R1-3ac,YZak), (R1-3ac,YZal), (R1-3ac,YZam), (R1-3ac,YZan), (R1-3ac,YZao), (R1-3ac,YZap), (R1-3ac,YZaq), (R1-3ac,YZar), (R1-3ac,YZas), (R1-3ac,YZat), (R1-3ac,YZau), (R1-3ad,YZa), (R1-3ad,YZb), (R1-3ad,YZc), (R1-3ad,YZd), (R1-3ad,YZe), (R1-3ad,YZf), (R1-3ad,YZg), (R1-3ad,Ya), (R1-3ad,YZi), (R1-3ad,YZj), (R1-3ad,YZk), (R1-3ad,YZl), (R1-3ad,YZm), (R1-3ad,YZn), (R1-3ad,YZo), (R1-3ad,YZp), (R1-3ad,YZq), (R1-3ad,YZr), (R1-3ad,YZs), (R1-3ad,YZt), (R1-3ad,YZu), (R1-3ad,YZv), (R1-3ad,YZw), (R1-3ad,Ya), (R1-3ad,YZy), (R1-3ad,YZz), (R1-3ad,YZaa), (R1-3ad,YZab), (R1-3ad,YZac), (R1-3ad,YZad), (R1-3ad,YZae), (R1-3ad,YZaf), (R1-3ad,YZag), (R1-3ad,YZah), (R1-3ad,YZai), (R1-3ad,YZaj), (R1-3ad,YZak), (R1-3ad,YZal), (R1-3ad,YZam), (R1-3ad,YZan), (R1-3ad,YZao), (R1-3ad,YZap), (R1-3ad,YZaq), (R1-3ad,YZar), (R1-3ad,YZas), (R1-3ad,YZat), (R1-3ad,YZau), (R1-3ae,YZa), (R1-3ae,YZb), (R1-3ae,YZc), (R1-3ae,YZd), (R1-3ae,YZe), (R1-3ae,YZf), (R1-3ae,YZg), (R1-3ae,YZh), (R1-3ae,YZi), (R1-3ae,YZj), (R1-3ae,YZk), (R1-3ae,YZl), (R1-3ae,YZm), (R1-3ae,YZn), (R1-3ae,YZo), (R1-3ae,YZp), (R1-3ae,YZq), (R1-3ae,YZr), (R1-3ae,YZs), (R1-3ae,YZt), (R1-3ae,YZu), (R1-3ae,YZv), (R1-3ae,YZw), (R1-3ae,Ya), (R1-3ae,YZy), (R1-3ae,YZz), (R1-3ae,YZaa), (R1-3ae,YZab), (R1-3ae,YZac), (R1-3ae,YZad), (R1-3ae,YZae), (R1-3ae,YZaf), (R1-3ae,YZag), (R1-3ae,YZah), (R1-3ae,YZai), (R1-3ae,YZaj), (R1-3ae,YZak), (R1-3ae,YZal), (R1-3ae,YZam), (R1-3ae,YZan), (R1-3ae,YZao), (R1-3ae,YZap), (R1-3ae,YZaq), (R1-3ae,YZar), (R1-3ae,YZas), (R1-3ae,YZat), (R1-3ae,YZau), (R1-3af,YZa), (R1-3af,YZb), (R1-3af,YZc), (R1-3af,YZd), (R1-3af,YZe), (R1-3af,YZf), (R1-3af,YZg), (R1-3af,YZh), (R1-3af,YZi), (R1-3af,YZj), (R1-3af,YZk), (R1-3af,YZl), (R1-3af,YZm), (R1-3af,YZn), (R1-3af,YZo), (R1-3af,YZp), (R1-3af,YZq), (R1-3af,YZr), (R1-3af,YZs), (R1-3af,YZt), (R1-3af,YZu), (R1-3af,YZv), (R1-3af,YZw), (R1-3af,YZx), (R1-

3af,YZy), (R1-3af,YZz), (R1-3af,YZaa), (R1-3af,YZab), (R1-3af,YZac), (R1-3af,YZad), (R1-3af,YZae), (R1-3af,YZaf), (R1-3af,YZag), (R1-3af,YZah), (R1-3af,YZai), (R1-3af,YZaj), (R1-3af,YZak), (R1-3af,YZal), (R1-3af,YZam), (R1-3af,YZan), (R1-3af,YZao), (R1-3af,YZap), (R1-3af,YZaq), (R1-3af,YZar), (R1-3af,YZas), (R1-3af,YZat), (R1-3af,YZau), (R1-3ag,YZa), (R1-3ag,YZb), (R1-3ag,YZc), (R1-3ag,YZd), (R1-3ag,YZe), (R1-3ag,YZf), (R1-3ag,YZg), (R1-3ag,YZh), (R1-3ag,YZi), (R1-3ag,YZj), (R1-3ag,YZk), (R1-3ag,YZl), (R1-3ag,YZm), (R1-3ag,YZn), (R1-3ag,YZo), (R1-3ag,YZp), (R1-3ag,YZq), (R1-3ag,YZr), (R1-3ag,YZs), (R1-3ag,YZt), (R1-3ag,YZu), (R1-3ag,YZv), (R1-3ag,YZw), (R1-3ag,Ya), (R1-3ag,YZy), (R1-3ag,YZz), (R1-3ag,YZaa), (R1-3ag,YZab), (R1-3ag,YZac), (R1-3ag,YZad), (R1-3ag,YZae), (R1-3ag,YZaf), (R1-3ag,YZag), (R1-3ag,YZah), (R1-3ag,YZai), (R1-3ag,YZaj), (R1-3ag,YZak), (R1-3ag,YZal), (R1-3ag,YZam), (R1-3ag,YZan), (R1-3ag,YZao), (R1-3ag,YZap), (R1-3ag,YZaq), (R1-3ag,YZar), (R1-3ag,YZas), (R1-3ag,YZat), (R1-3ag,YZau), (R1-3ah,YZa), (R1-3ah,YZb), (R1-3ah,YZc), (R1-3ah,YZd), (R1-3ah,YZe), (R1-3ah,YZf), (R1-3ah,YZg), (R1-3ah,YZh), (R1-3ah,YZi), (R1-3ah,YZj), (R1-3ah,YZk), (R1-3ah,YZl), (R1-3ah,YZm), (R1-3ah,YZn), (R1-3ah,YZo), (R1-3ah,YZp), (R1-3ah,YZq), (R1-3ah,YZr), (R1-3ah,YZs), (R1-3ah,YZt), (R1-3ah,YZu), (R1-3ah,YZv), (R1-3ah,YZw), (R1-3ah,YZx), (R1-3ah,YZy), (R1-3ah,YZz), (R1-3ah,YZaa), (R1-3ah,YZab), (R1-3ah,YZac), (R1-3ah,YZad), (R1-3ah,YZae), (R1-3ah,YZaf), (R1-3ah,YZag), (R1-3ah,YZah), (R1-3ah,YZai), (R1-3ah,YZaj), (R1-3ah,YZak), (R1-3ah,YZal), (R1-3ah,YZam), (R1-3ah,YZan), (R1-3ah,YZao), (R1-3ah,YZap), (R1-3ah,YZaq), (R1-3ah,YZar), (R1-3ah,YZas), (R1-3ah,YZat), (R1-3ah,YZau), (R1-3ai,YZa), (R1-3ai,YZb), (R1-3ai,YZc), (R1-3ai,YZd), (R1-3ai,YZe), (R1-3ai,YZf), (R1-3ai,YZg), (R1-3ai,YZh), (R1-3ai,YZi), (R1-3ai,YZj), (R1-3ai,YZk), (R1-3ai,YZl), (R1-3ai,YZm), (R1-3ai,YZn), (R1-3ai,YZo), (R1-3ai,YZp), (R1-3ai,YZq), (R1-3ai,YZr), (R1-3ai,YZs), (R1-3ai,YZt), (R1-3ai,YZu), (R1-3ai,YZv), (R1-3ai,YZw), (R1-3ai,YZx), (R1-3ai,YZy), (R1-3ai,YZz), (R1-3ai,YZaa), (R1-3ai,YZab), (R1-3ai,YZac), (R1-3ai,YZad), (R1-3ai,YZae), (R1-3ai,YZaf), (R1-3ai,YZag), (R1-3ai,YZah), (R1-3ai,YZai), (R1-3ai,YZaj), (R1-3ai,YZak), (R1-3ai,YZal), (R1-3ai,YZam), (R1-3ai,YZan), (R1-3ai,YZao), (R1-3ai,YZap), (R1-3ai,YZaq), (R1-3ai,YZar), (R1-3ai,YZas), (R1-3ai,YZat), (R1-3ai,YZau), (R1-3aj,YZa), (R1-3aj,YZb), (R1-3aj,YZc), (R1-3aj,YZd), (R1-3aj,YZe), (R1-3aj,YZf), (R1-3aj,YZg), (R1-3aj,YZh), (R1-3aj,YZi), (R1-3aj,YZj), (R1-3aj,YZk), (R1-3aj,YZl), (R1-3aj,YZm), (R1-3aj,YZn), (R1-3aj,YZo), (R1-3aj,YZp), (R1-3aj,YZq), (R1-3aj,YZr), (R1-3aj,YZs), (R1-3aj,YZt), (R1-3aj,YZu), (R1-3aj,YZv), (R1-3aj,YZw), (R1-3aj,YZx), (R1-3aj,YZy), (R1-3aj,YZz), (R1-3aj,YZaa), (R1-3aj,YZab), (R1-3aj,YZac), (R1-3aj,YZad), (R1-3aj,YZae), (R1-3aj,YZaf), (R1-3aj,YZag), (R1-3aj,YZah), (R1-3aj,YZai), (R1-3aj,YZaj), (R1-3aj,YZak), (R1-3aj,YZal), (R1-3aj,YZam), (R1-3aj,YZan), (R1-3aj,YZao), (R1-3aj,YZap), (R1-3aj,YZaq), (R1-3aj,YZar), (R1-3aj,YZas), (R1-3aj,YZat), (R1-3aj,YZau), (R1-3ak,YZa), (R1-3ak,YZb), (R1-3ak,YZc), (R1-3ak,YZd), (R1-3ak,YZe), (R1-3ak,YZf), (R1-3ak,YZg), (R1-3ak,YZh), (R1-3ak,YZi), (R1-3ak,YZj), (R1-3ak,YZk), (R1-3ak,YZl), (R1-3ak,YZm), (R1-3ak,YZn), (R1-3ak,YZo), (R1-3ak,YZp), (R1-3ak,YZq), (R1-3ak,YZr), (R1-3ak,YZs), (R1-3ak,YZt), (R1-3ak,YZu), (R1-3ak,YZv), (R1-3ak,YZw), (R1-3ak,YZx), (R1-3ak,YZy), (R1-3ak,YZz), (R1-3ak,YZaa), (R1-3ak,YZab), (R1-3ak,YZac), (R1-3ak,YZad), (R1-3ak,YZae), (R1-3ak,YZaf), (R1-3ak,YZag), (R1-3ak,YZah), (R1-3ak,YZai), (R1-3ak,YZaj), (R1-3ak,YZak), (R1-3ak,YZal), (R1-3ak,YZam), (R1-3ak,YZan), (R1-3ak,YZao), (R1-3ak,YZap), (R1-3ak,YZaq), (R1-3ak,YZar), (R1-3ak,YZas), (R1-3ak,YZat), (R1-3ak,YZau), (R1-3al,YZa), (R1-3al,YZb), (R1-3al,YZc), (R1-3al,YZd), (R1-3al,YZe), (R1-3al,YZf), (R1-3al,YZg), (R1-3al,YZh), (R1-3al,YZi), (R1-3al,YZj), (R1-3al, YZk), (R1-3al, YZl), (R1-3al, YZm), (R1-3al,YZn), (R1-3al,YZo), (R1-3al,YZp), (R1-3al,YZq), (R1-3al,YZr), (R1-3al,YZs), (R1-3al,YZt), (R1-3al, YZu), (R1-3al,YZv), (R1-3al,YZw), (R1-3al, YZx), (R1-3al,YZy), (R1-3al,YZz), (R1-3al,YZaa), (R1-3al,YZab), (R1-3al, YZac), (R1-3al, YZad), (R1-3al, YZae), (R1-3al,YZaf), (R1-3al,YZag), (R1-3al,YZah), (R1-3al,YZai), (R1-3al, YZaj), (R1-3al,YZak), (R1-3al,YZal), (R1-3al,YZam), (R1-3al,YZan), (R1-3al,YZao), (R1-3al, YZap), (R1-3al, YZaq), (R1-3al,YZar), (R1-3al,YZas), (R1-3al,YZat), (R1-3al,YZau), (R1-3am,YZa), (R1-3am,YZb), (R1-3am,YZc), (R1-3am,YZd), (R1-3am,YZe), (R1-3am,YZf), (R1-3am,YZg), (R1-3am,YZh), (R1-3am,YZi), (R1-3am,YZj), (R1-3am,YZk), (R1-3am,YZl), (R1-3am,YZm), (R1-3am,YZn), (R1-3am,YZo), (R1-3am,YZp), (R1-3am,YZq), (R1-3am,YZr), (R1-3am,YZs), (R1-3am,YZt), (R1-3am,YZu), (R1-3am,YZv), (R1-3am,YZw), (R1-3am,YZx), (R1-3am,YZy), (R1-3am,YZz), (R1-3am,YZaa), (R1-3am,YZab), (R1-3am,YZac), (R1-3am,YZad), (R1-3am,YZae), (R1-3am,YZaf), (R1-3am,YZag), (R1-3am,YZah), (R1-3am,YZai), (R1-3am,YZaj), (R1-3am,YZak), (R1-3am,YZal), (R1-3am,YZam), (R1-3am,YZan), (R1-3am,YZao), (R1-3am,YZap), (R1-3am,YZaq), (R1-3am,YZar), (R1-3am,YZas), (R1-3am,YZat), (R1-3am,YZau).

In one embodiment, preferable acrylamide compounds are the compounds of the following Formula IA:

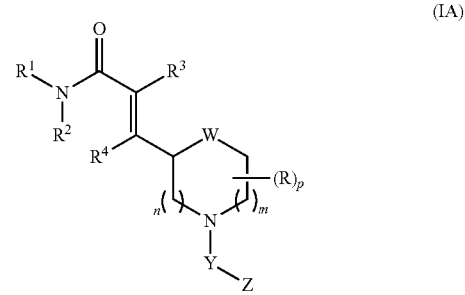

(IA)

wherein $R^1$ and $R^2$ are each independently hydrogen, optionally substituted alkyl, optionally substituted cycloalkyl or optionally substituted aryl;

$R^3$ and $R^4$ are each independently hydrogen or optionally substituted alkoxy;

W is —CH$_2$—, m is 0 and n is 2; or W is —O—, m is 1 and n is 1;

p is 0;

Y is —S(O)$_2$—; and

Z is optionally substituted aryl.

In another embodiment, preferable acrylamide compounds are the above compound IA wherein $R^1$ and $R^2$ are each independently hydrogen, cycloalkyl, cycloalkylalkyl or aryl;

$R^3$ and $R^4$ are each independently hydrogen or alkoxy;

W is —CH$_2$—, m is 0 and n is 2; or W is —O—, m is 1 and n is 1;

p is 0;

Y is —S(O)$_2$—; and

Z is aryl optionally substituted with haloalkoxy.

In another embodiment, preferable acrylamid compounds are the above compound IA wherein
$R^1$ and $R^2$ are each independently hydrogen or cycloalkyl;
$R^3$ and $R^4$ are each independently hydrogen or alkoxy;
W is $-CH_2-$, m is 0 and n is 2; or W is $-O-$, m is 1 and n is 1;
p is 0;
Y is $-S(O)_2-$; and
Z is aryl optionally substituted with haloalkoxy.

The invention disclosed herein is also meant to encompass prodrugs of any of the disclosed compounds. As used herein, prodrugs are considered to be any covalently bonded carriers that release the active parent drug in vivo. In general, such prodrugs will be a functional derivative of a compound of Formula I, IA or IB which are readily convertible in vivo, e.g., by being metabolized, into the required compound of Formula I, IA or IB. Conventional procedures for the selection and preparation of suitable prodrug derivatives are described in, for example, NPL13; NPL14; NPL15; NPL16; NPL17; and NPL18. Non-limiting examples of prodrugs include esters or amides of compounds of Formula I, IA or IB having hydroxy or amino as a substituent, and these can be prepared by reacting such compounds with anhydrides such as succinic anhydride.

The invention disclosed herein is also meant to encompass any of the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, and preferably $^3H$, $^{11}C$, and $^{14}C$. Isotopically-labeled compounds of the present invention can be prepared by methods known in the art.

The present invention is also directed specifically to $^3H$, $^{11}C$, and $^{14}C$ radiolabeled compounds of Formula I, IA or IB as well as their pharmaceutically acceptable salts, and solvates, and the use of any such compounds as radioligands for their binding site on the calcium channel. For example, one use of the labeled compounds of the present invention is the characterization of specific receptor binding. Another use of the labeled compounds of the present invention is an alternative to animal testing for the evaluation of structure-activity relationships. For example, the receptor assay may be performed at a fixed concentration of a labeled compound of Formula I, IA or IB and at increasing concentrations of a test compound in a competition assay. For example, tritiated compounds of any of Formula I, IA or IB can be prepared by introducing tritium into the particular compound of Formula I, IA or IB, for example, by catalytic dehalogenation with tritium. This method may include reacting a suitably halogen-substituted precursor of a compound of Formula I, IA or IB with tritium gas in the presence of a suitable catalyst, for example, Pd/C, in the presence or absence of a base. Other suitable methods for preparing tritiated compounds can be found in NPL19. $^{14}C$-labeled compounds can be prepared by employing starting materials having a $^{14}C$ carbon.

Some of the compounds disclosed herein may contain one or more asymmetric centers and may thus give rise to enantiomers, diastereomers, and other stereoisomeric forms. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" is meant to encompass administering to a subject a compound of the present invention for the purposes of amelioration or cure, including preemptive and palliative treatment.

The invention disclosed herein also encompasses the use of all salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, hydrofluoride, phosphate, sulfate, nitrate and the like; organic acid salts such as citrate, lactate, tartrate, maleate, fumarate, mandelate, acetate, dichloroacetate, trifluoroacetate, oxalate, formate, succinate, and the like; sulfonates such as methanesulfonate, benzenesulfonate, p-toluenesulfonate and the like; and amino acid salts such as arginate, asparginate, glutamate and the like. Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of any of the disclosed compounds. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of any of Formulae I, IA or IB may be present as solvated forms with a pharmaceutically acceptable solvent, such as water, methanol, ethanol, and the like, and it is intended that the invention includes both solvated and unsolvated forms of compounds of any of Formulae I, IA or IB. One type of solvate is a hydrate. A "hydrate" relates to a particular subgroup of solvates where the solvent molecule is water. Solvates typically can function as pharmacological equivalents. Preparation of solvates is known in the art. See, for example, NPL20, which describes the preparation of solvates of fluconazole with ethyl acetate and with water. Similar preparation of solvates, hemisolvates, hydrates, and the like are described by NPL21, and NPL22. A typical, non-limiting, process of preparing a solvate would involve dissolving a compound of any of Formulae I, IA or IB in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Some compounds of the present invention may have one or more of the following characteristics:
high affinity for calcium ($Ca^{2+}$) channels, especially N-type calcium channels,
high selectivity to calcium ($Ca^{2+}$) channels, especially N-type calcium channels versus other channels,
reduced side effect,
high stability,
high oral absorbability,
high bioavailability,
low clearance,
easily transfers to brain,
long half-life,
long efficacy of a medicine, and/or
high protein-unbound fraction.

These compounds are considered useful as blockers of calcium ($Ca^{2+}$) channels, especially N-type calcium channels.

Since compounds of Formula I, IA and IB are blockers of calcium ($Ca^{2+}$) channels, a number of diseases and conditions mediated by calcium ion influx can be treated by employing these compounds. Therefore, the present invention provides a method of treating or preventing stroke, neuronal damage resulting from head trauma, epilepsy, pain (e.g., acute pain, chronic pain, which includes but is not limited to, neuropathic pain and inflammatory pain or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, said method comprising administering to the animal an effective amount of at least one compound of Formula I, IA or IB, or a pharmaceutically acceptable salt, or a solvate thereof. In one embodiment, the invention provides a method of treating pain. In another embodiment, the type of pain treated is chronic pain. In another embodiment, the type of pain treated is neuropathic pain. In another embodiment, the type of pain treated is inflammatory pain. In another embodiment, the type of pain treated is acute pain. In each instance, such method of treatment or prevention require administering to an animal in need of such treatment or prevention an amount of a compound of the present invention that is therapeutically effective in achieving said treatment or prevention. In one embodiment, the amount of such compound is the amount that is effective as to block calcium channels in vivo. Chronic pain includes, but is not limited to, neuropathic pain, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (NPL23).

The inflammatory process is a complex series of biochemical and cellular events activated in response to tissue injury or the presence of foreign substances (NPL24). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed to use of a compound represented by Formula I, IA or IB, or a pharmaceutically acceptable salt or a solvate thereof, in the manufacture of a medicament for treating or preventing stroke, neuronal damage resulting from head trauma, epilepsy, pain (e.g., acute pain, chronic pain, which includes but is not limited to, neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia in an animal.

The present invention is also directed more generally to a method for treating a disorder responsive to the blockade of calcium channels, and particularly the selective blockade of N-type calcium channels, in an animal suffering from said disorder, said method comprising administering to the animal an effective amount of a compound represented by any of defined Formula I, IA or IB, or a pharmaceutically acceptable salt or a solvate thereof.

The present invention is also directed to the use of a compound of Formula I, IA or IB, or a pharmaceutically acceptable salt or a solvate thereof, in the manufacture of a medicament for treating a disorder responsive to the blockade of calcium channels in an animal suffering from said disorder. In one embodiment, the disorder is responsive to the selective blockade of N-type calcium channels.

Furthermore, the present invention is directed to a method of modulating calcium channels, especially N-type calcium channels, in an animal in need thereof, said method comprising administering to the animal at least one compound represented by any of defined Formula I, IA or IB, or a pharmaceutically acceptable salt or a solvate thereof.

The present invention is also directed to the use of a compound of Formula I, IA or IB, or a pharmaceutically acceptable salt or a solvate thereof, in the manufacture of a medicament for modulating calcium channels, especially N-type calcium channels, in an animal in need thereof.

Synthesis of Compounds

The compounds of the present invention can be prepared in a number of ways well known to those skilled in the art. The compounds of the present invention can be synthesized using the methods outlined below, together with methods known in the art of synthetic organic chemistry, or variations thereof as appreciated by those skilled in the art. Preferred methods include, but are not limited to, those described below.

The novel compounds of Formula I can be prepared using the reactions and techniques described in this section. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. It is understood by one skilled in the art that the functionality present on various portions of the starting molecule in a reaction must be compatible with the reagents and reactions proposed. Not all compounds of Formula I falling into a given class may be compatible with some of the reaction conditions required in some of the methods described. Such restrictions to the substituents which are compatible with the reaction conditions will be readily apparent to one skilled in the art and alternative methods can be used. Compounds of Formula I can be prepared by techniques and procedures readily available to one skilled in the art, for example by following the procedures as set forth in the following Schemes. These Schemes are not intended to limit the scope of the invention in any way. All substituents, unless otherwise indicated, are previously defined. The reagents and starting materials are readily available to one skilled in the art.

In order to generate compounds of general formula I, a multi-step reaction sequence as described in Scheme 1 can be employed. Herein, a suitably protected piperidone (1a), wherein $P^1$—O—C—$OP^1$ is, for example, 1,3-dioxolane, is reacted with a sulfonyl chloride (Z—Y—Cl, Y: $S(O)_2$), a halide or their corresponding equivalent (Z—Y-hal; hal=Cl, Br, I, OTs etc.) by using standard conditions, familiar to one skilled in the art. Deprotection of the compound (1b) may be accomplished using standard conditions, familiar to one skilled in the art. The free ketone (1e) may then be coupled with a triphenyl phosphonium ylide or a stabilized phosphonate carbanion. Typically the reaction is effected using standard "Wittig reaction" or "Horner-Wadsworth-Emmons reaction" conditions, familiar to one skilled in the art. Hydrolysis of the resulting ester (1f) wherein $P^2$ is, for example, methyl, ethyl or tert-butyl, may be accomplished using standard conditions, familiar to one skilled in the art. The resulting carboxylic acid (1 g) can be coupled with an amine $HNR^1R^2$, wherein $R^1$ and $R^2$ are as defined above for Formula I, using standard amide coupling conditions, familiar to one skilled in the art, such as 1-(3-dimethylaminopropyl)-3-ethylcarbodiimide hydrochloride, to yield the desired compound (Ia). The intermediate (1e) may also be synthesized starting from 4-piperidone monohydrate hydrochloride (1c) or 1-benzyl-1-methyl-4-oxopiperidinium iodide (1d). The former can be reacted with a sulfonyl chloride (Z—Y—Cl, Y: $S(O)_2$), a halide or their corresponding equivalent (Z—Y-hal; Y: $CR^7R^8$, hal: Cl, Br, I, OTs etc.) by using standard conditions, familiar to one skilled in the art, and the latter may be reacted with a primary amine (Z—Y—$NH_2$, Y: $CR^7R^8$).

Scheme 1

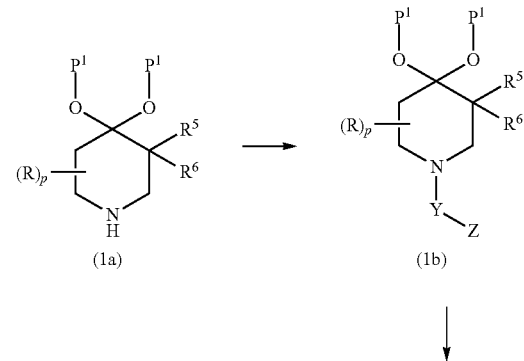

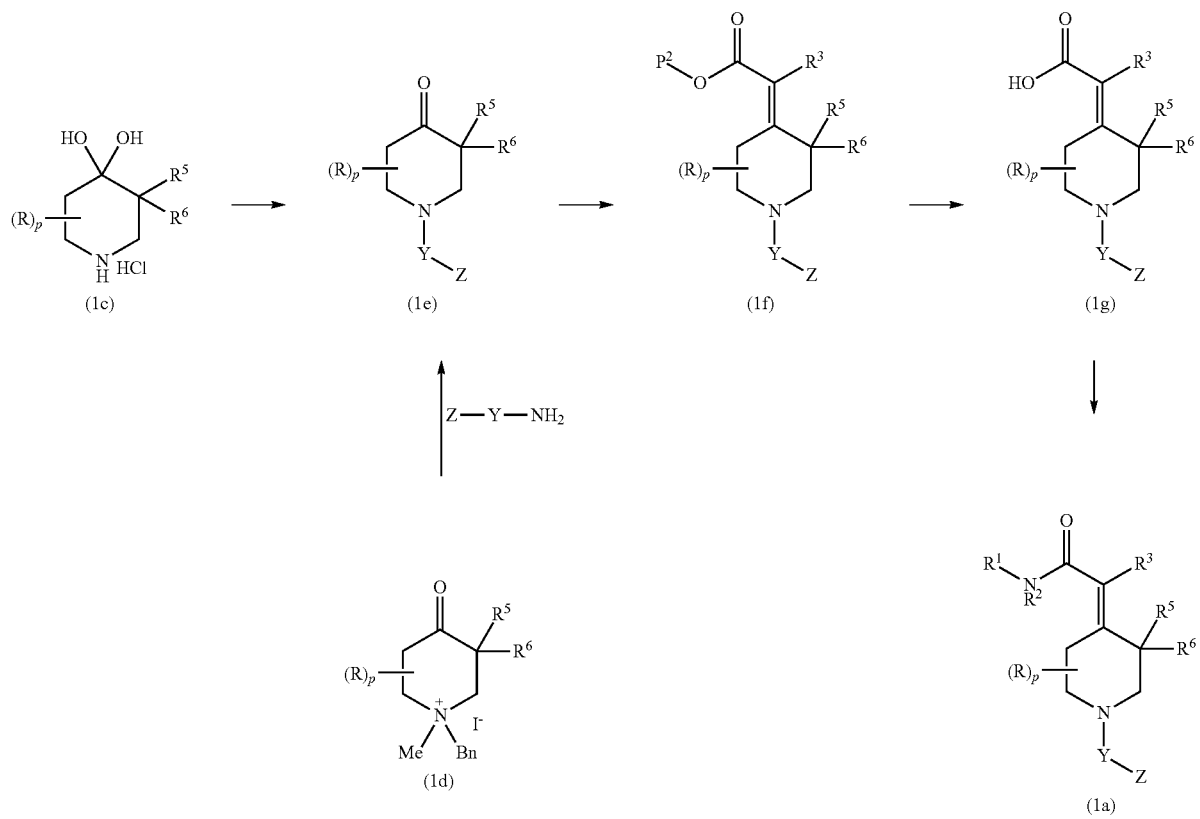

(wherein P¹ is a carbonyl protecting group and for example, P¹O—C—OP¹ is 1,3-dioxolane and the like and P² is a carboxyl protecting group such as methyl, ethyl or tert-butyl and the like, Bn is benzyl, and the other symbols are as defined above).

An alternative way of preparing some of the compounds of the present invention is detailed in Scheme 2. As an alternative to Scheme 1, Scheme 2 employs a suitably N-protected piperidone (2a), which may be coupled with a triphenyl phosphonium ylide or a stabilized phosphonate carbanion. Typically the reaction is effected using standard "Wittig reaction" or "Horner-Wadsworth-Emmons reaction" conditions, familiar to one skilled in the art. Hydrolysis of the resulting ester (2b), wherein P² is, for example, methyl, ethyl or tert-butyl, may be accomplished using standard conditions, familiar to one skilled in the art. The resulting carboxylic acid (2c) can be coupled with an amine wherein $R^1$ and $R^2$ are as defined above, using standard amide coupling conditions, familiar to one skilled in the art, such as 1-(3-dimethylaminopropyl)-3-ethylcarbodiimide hydrochloride. Deprotection of the compound (2d) may be accomplished using standard conditions, familiar to one skilled in the art. Finally, the compound (2e) can be reacted with a sulfonyl chloride (Z—Y—Cl, Y: S(O)₂), a halide or their corresponding equivalent (Z—Y-hal; Y: $CR^7R^8$, hal: Cl, Br, I, OTs etc.) by using standard conditions, familiar to one skilled in the art, to yield the desired compound (Ia).

Scheme 2

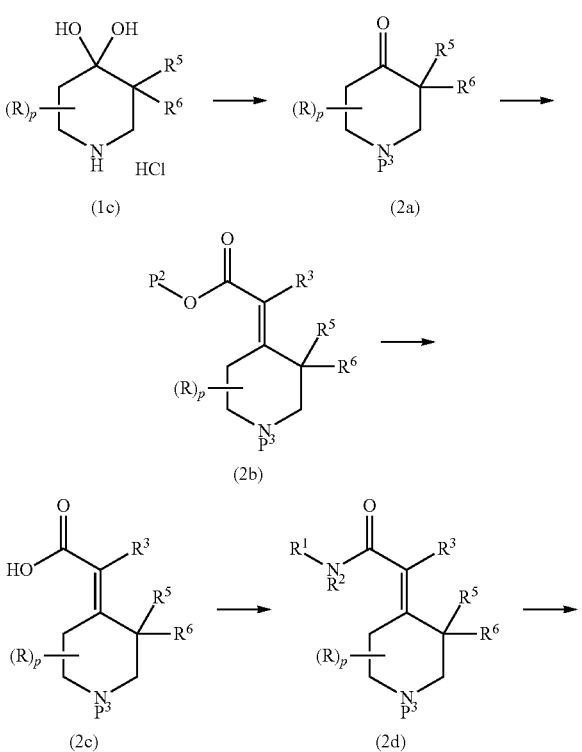

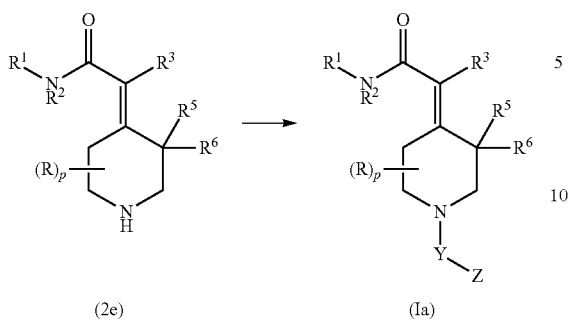

(wherein P² is a carboxyl protecting group, such as methyl, ethyl or tert-butyl and the like, and P³ is an amino protecting group, such as tert-butoxycarbonyl and the like, and the other symbols are as defined above).

In order to generate compounds of general formula (Ib), a multi-step reaction sequence as described in Scheme 3 can be employed. Herein, a suitably N-protected 4-(hydroxymethyl) piperidine (3a) wherein P³ is, for example, tert-butoxycarbonyl, is converted into the aldehyde or ketone (3b) by using standard conditions, familiar to one skilled in the art. The aldehyde or ketone (3b) may then be coupled with a triphenyl phosphonium ylide or a stabilized phosphonate carbanion. Typically the reaction is effected using standard "Wittig reaction" or "Horner-Wadsworth-Emmons reaction" conditions, familiar to one skilled in the art. Deprotection of the compound (3c) may be accomplished using standard conditions, familiar to one skilled in the art. The compound (3d) can be reacted with a sulfonyl chloride (Z—Y—Cl, Y: S(O)₂), a halide or their corresponding equivalent (Z—Y-hal; Y: CR⁷R⁸, hal: Cl, Br, I, OTs etc.) by using standard conditions, familiar to one skilled in the art. Hydrolysis of the resulting ester (3e) wherein P² is, for example, methyl, ethyl or tert-butyl, may be accomplished using standard conditions, familiar to one skilled in the art. The resulting carboxylic acid (3O can be coupled with an amine HNR¹R², wherein R¹ and R² are as defined above, using standard amide coupling conditions, familiar to one skilled in the art, such as 1-(3-dimethylaminopropyl)-3-ethylcarbodiimide hydrochloride, to yield the desired compound (Ib).

Scheme 3

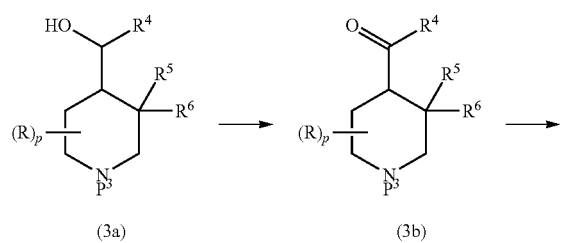

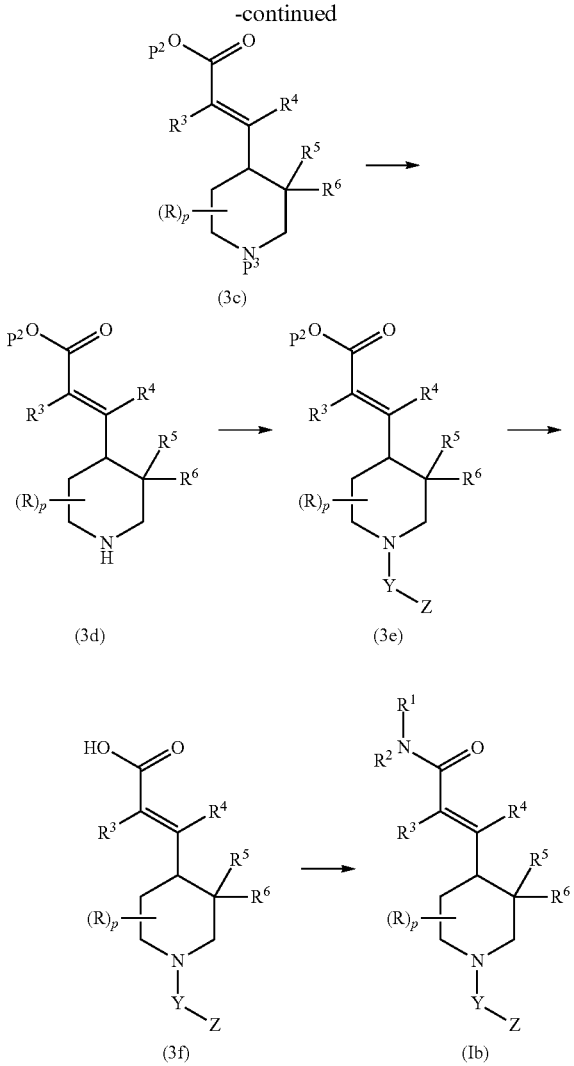

(wherein P² is a carboxyl protecting group, such as methyl, ethyl or tert-butyl and the like, and P³ is an amino protecting group, such as tert-butoxycarbonyl and the like, and the other symbols are as defined above).

As an alternative to Scheme 3, Scheme 4 employs 4-(hydroxymethyl)piperidine (4a), which may be reacted with a sulfonyl chloride (Z—Y—Cl, Y: S(O)₂) using standard conditions, familiar to one skilled in the art. The resulting alcohol (4b) can be converted into the aldehyde or ketone (4c) by using standard conditions, familiar to one skilled in the art. The aldehyde or ketone (4c) may then be coupled with a triphenyl phosphonium ylide or a stabilized phosphonate carbanion. Typically the reaction is effected using standard "Wittig reaction" or "Horner-Wadsworth-Emmons reaction" conditions, familiar to one skilled in the art. Hydrolysis of the resulting ester (3e) wherein P² is, for example, methyl, ethyl or tert-butyl, may be accomplished using standard conditions, familiar to one skilled in the art. The resulting carboxylic acid (3f) can be coupled with an amine HNR¹R², wherein R¹ and R² are as defined above, using standard amide coupling conditions, familiar to one skilled in the art, such as 1-(3-dimethylaminopropyl)-3-ethylcarbodiimide hydrochloride, to yield the desired compound (Ib).

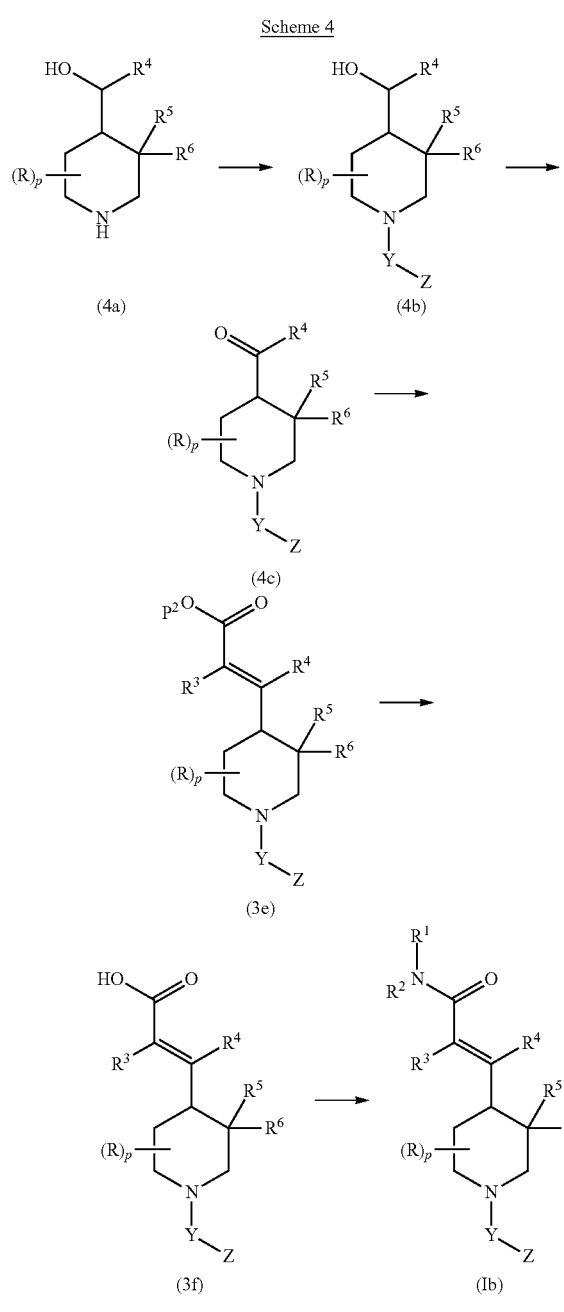

Scheme 4

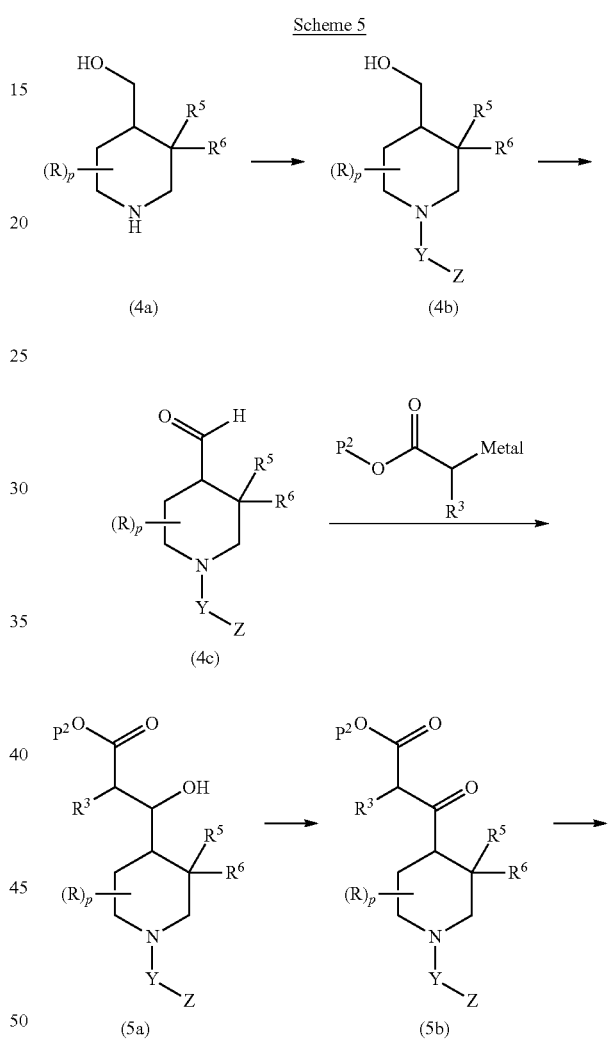

Scheme 5 accomplished using standard conditions, familiar to one skilled in the art. The resulting carboxylic acid (5d) can be coupled with an amine wherein $R^1$ and $R^2$ are as defined above, using standard amide coupling conditions, familiar to one skilled in the art, such as 1-(3-dimethylaminopropyl)-3-ethylcarbodiimide hydrochloride, to yield the desired compound (Ib).

(wherein $P^2$ is a carboxyl protecting group, such as methyl, ethyl or tert-butyl and the like, and the other symbols are as defined above).

As an alternative to Scheme 4, Scheme 5 employs the intermediate (5a), which may be synthesized from the aldehyde (4c) using an organometallic reagent (Metal: ZnX etc. wherein X is halogen) under standard conditions, familiar to one skilled in the art. The resulting alcohol (5a) can be converted into the ketoester (5b) by using standard conditions, familiar to one skilled in the art. The ketoester (5b) may then be converted into the compound (5c) such as an enol ether ($R^4$: alkoxy etc.) by using standard conditions, familiar to one skilled in the art. Hydrolysis of the resulting ester (5c) wherein $P^2$ is, for example, methyl, ethyl or tert-butyl, may be

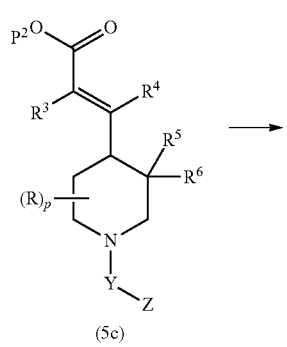

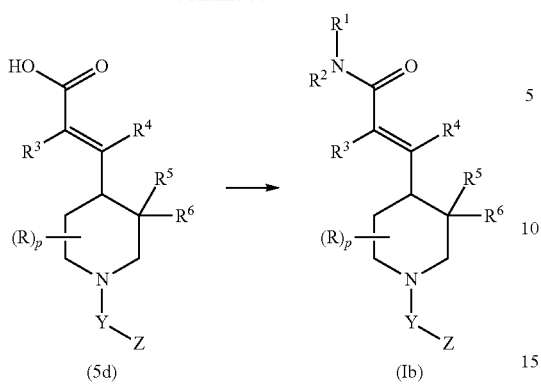

(wherein P² is a carboxyl protecting group, such as methyl, ethyl or tert-butyl and the like, and Metal is a metal species such as ZnX, wherein X is halogen, and the other symbols are as defined above).

In order to generate compounds of general formula (Ic), a multi-step reaction sequence as described in Scheme 6 can be employed. Herein, a suitably N-protected piperidin-3-one (6a) wherein P³ is, for example, tert-butoxycarbonyl, may be coupled with a triphenyl phosphonium ylide or a stabilized phosphonate carbanion. Typically the reaction is effected using standard "Wittig reaction" or "Horner-Wadsworth-Emmons reaction" conditions, familiar to one skilled in the art. Deprotection of the compound (6b) may be accomplished using standard conditions, familiar to one skilled in the art. The resulting amino acid (6c) may be reacted with a sulfonyl chloride (Z—Y—Cl, Y: S(O)₂) using standard conditions, familiar to one skilled in the art. Finally, the carboxylic acid (6d) can be coupled with an amine HNR¹R², wherein R¹ and R² are as defined above, using standard amide coupling conditions, familiar to one skilled in the art, such as 1-(3-dimethylaminopropyl)-3-ethylcarbodiimide hydrochloride, to yield the desired compound (Ic).

Scheme 6

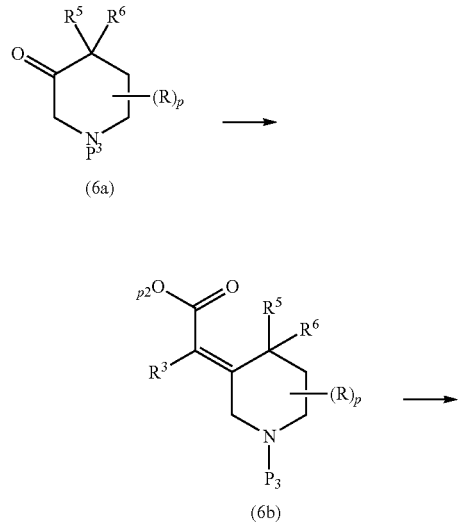

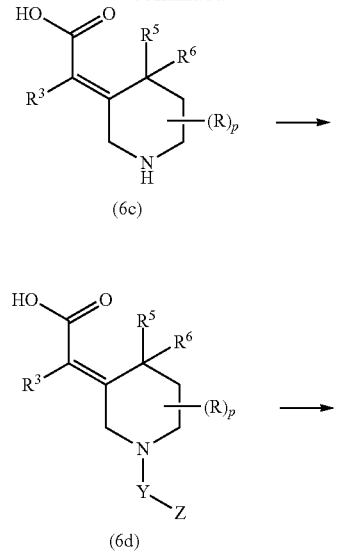

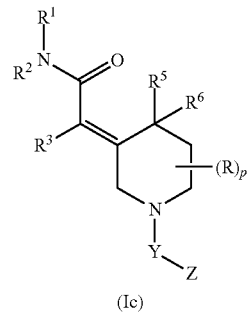

(wherein P² is a carboxyl protecting group, such as methyl, ethyl or tert-butyl and the like, and P³ is an amino protecting group, such as tert-butoxycarbonyl and the like, and the other symbols are defined above).

In order to generate compounds of general formula (Id), a multi-step reaction sequence as described in Scheme 7 may be employed. Herein, a hydroxymethyl-substituted cyclic amine (7a) may be reacted with a sulfonyl chloride (Z—Y—Cl, Y: S(O)₂) using standard conditions, familiar to one skilled in the art. The resulting alcohol (7b) can be converted into an aldehyde or ketone (7c) by using standard conditions, familiar to one skilled in the art. The aldehyde or ketone (7c) may then be coupled with a triphenyl phosphonium ylide or a stabilized phosphonate carbanion. Typically the reaction is effected using standard "Wittig reaction" or "Horner-Wadsworth-Emmons reaction" conditions, familiar to one skilled in the art. Hydrolysis of the resulting ester (7d) wherein P² is, for example, methyl, ethyl or tert-butyl, may be accomplished using standard conditions, familiar to one skilled in the art. The resulting carboxylic acid (7e) can be coupled with an amine HNR¹R², wherein R¹ and R² are as defined above, using standard amide coupling conditions, familiar to one skilled in the art, such as 1-(3-dimethylaminopropyl)-3-ethylcarbodiimide hydrochloride, to yield the desired compound (Id).

Scheme 7

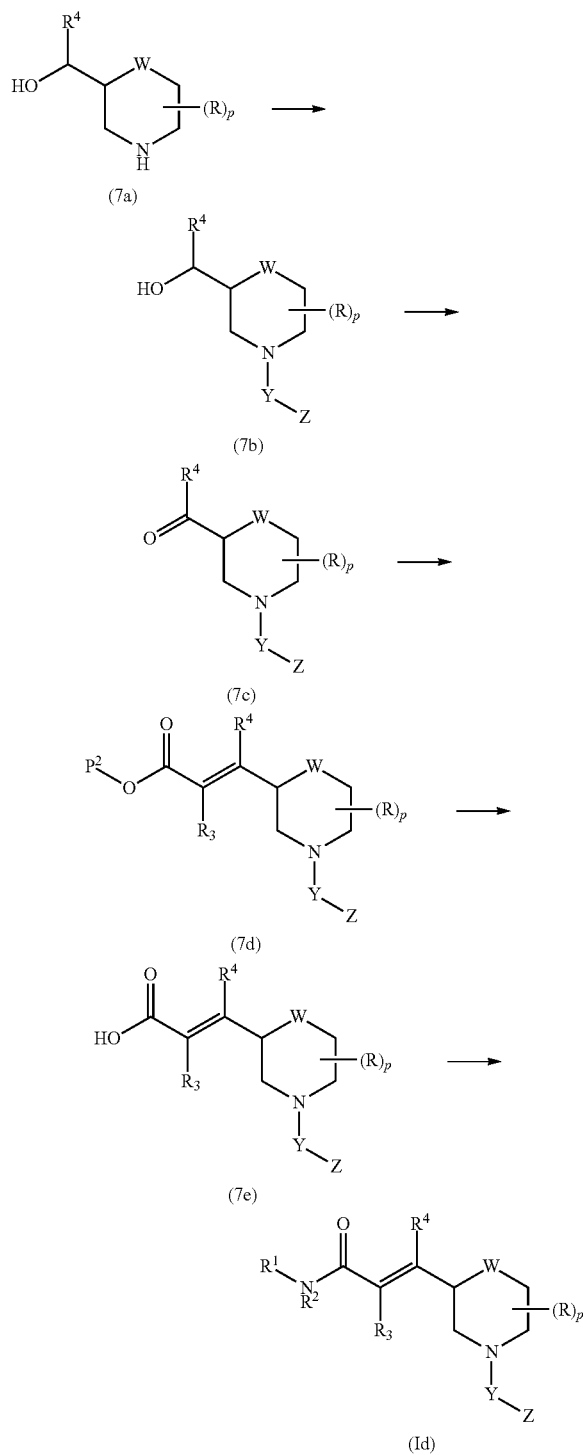

(wherein $P^2$ is a carboxyl protecting group, such as methyl, ethyl or tert-butyl and the like, and the other symbols are defined above).

Testing of Compounds

Representative compounds of the present invention were assessed by calcium mobilization and/or electrophysiological assays for calcium channel blocker activity. One aspect of the present invention is based on the use of the compounds herein described as N-type calcium channel blockers. In one aspect of the present invention, it has been found that certain compounds herein described show selectivity as N-type calcium channel blockers. Based upon this property, these compounds are considered useful in treating or preventing migraine, epilepsy, a mood disorder, schizophrenia, a neurodegenerative disorder (such as, e.g., Alzheimer's disease, ALS, or Parkinson's disease), a psychosis, depression, anxiety, hypertension, or cardiac arrhythmia. The compounds of the present invention are also expected to be effective in treating or preventing pain, such as acute pain, chronic pain, which includes but is not limited to, neuropathic pain and inflammatory pain or surgical pain.

More specifically, the present invention is directed to compounds of Formula I, IA and IB that are blockers of calcium channels. According to the present invention, those compounds having preferred N-type calcium channel blocking properties exhibit an $IC_{50}$ of about 100 µM or less in the calcium mobilization and/or electrophysiological assays described herein. Preferably, the compounds of the present invention exhibit an $IC_{50}$ of 10 µM or less. Most preferably, the compounds of the present invention exhibit an $IC_{50}$ of about 1.0 µM or less. Compounds of the present invention can be tested for their N-type and L-type $Ca^{2+}$ channel blocking activity by the following calcium mobilization and/or electrophysiological assays.

In one embodiment, compounds useful in the present invention are those represented by any one of Formula I, IA or IB that exhibit selectivity for N-type calcium channels over L-type calcium channels in the calcium mobilization and/or electrophysiological assays described herein. The phrase "selectivity for N-type calcium channels over L-type calcium channels" is used herein to mean that the ratio of an $IC_{50}$ for L-type channel blocking activity for a compound of the present invention over an $IC_{50}$ for N-type channel blocking activity for the same compound is more than 1, i.e., LTCC $IC_{50}$/NTCC $IC_{50}$>1. Preferably, compounds of the present invention exhibit an LTCC $IC_{50}$/NTCC $IC_{50}$ ratio of about 2 or more, about 10 or more, about 20 or more, about 30 or more, about 50 or more, or about 100 or more.

Calcium Mobilization and Electrophysiological Assay Protocols:

Cell maintenance and differentiation. Unless noted otherwise, cell culture reagents were purchased from Mediatech of Herndon, Md. IMR32 cells (American Type Culture Collection, ATCC, Manassas, Va.) were routinely cultured in growth medium consisting of minimum essential medium containing 10% fetal bovine serum (FBS, Hyclone, Logan, Utah), 100 U/mL penicillin, 100 µg/mL streptomycin, 2 mM L-glutamine, 1 mM sodium pyruvate, and 1×MEM non-essential amino acids. 80-90% confluent flasks of cells were differentiated using the following differentiation medium: Growth medium plus 1 mM dibutyryl cyclic AMP (Sigma, St. Louis, Mo.), and 2.5 µM bromodeoxyuridine (Sigma). Cells were differentiated for 8 days by replacing differentiation medium every 2-3 days.

A7r5 (ATCC) cells were maintained and routinely cultured in A7r5 growth medium consisting of Dulbecco's Modified Eagles Medium containing 10% FBS, 100 U/mL penicillin, 100 µg/mL streptomycin, 4 mM L-glutamine, and 0.15% sodium bicarbonate. 80-90% confluent flasks of cells were differentiated using the following differentiation medium: A7r5 Growth Medium plus 1 mM dibutyryl cyclic AMP (Sigma). Cells were differentiated for 8 days by replacing differentiation medium every 2-3 days.

Recombinant human embryonal kidney cells (HEK293, ATCC) stably transfected with either N-type calcium channel (NTCC) subunits (α1b, α2δ, and β3) or L-type calcium channel (LTCC) subunits (α1c, α2δ, and β1) were routinely cultured in growth medium consisting of Dulbecco's Modified Eagles Medium containing 10% FBS, 100 U/mL penicillin, 100 μg/mL streptomycin, 4 mM L-glutamine, 500 μg/mL geneticin (G418), 20 μg/mL Blasticidin S (InVivogen, San Diego, Calif.) and 500 μg/mL zeocin (InVivogen).

FLIPR Calcium Mobilization Assay for N-type Calcium Channel. One day prior to performing this assay, differentiated IMR32 cells were treated with 1× CellStripper, and seeded on poly-D-lysine-coated 96-well clear-bottom black plates (Becton Dickinson, Franklin Lakes, N.J.) at 200,000 cells/well. On the day of the assay, the cell plates were washed with IMR32 buffer (127 mM NaCl, 1 mM KCl, 2 mM $MgCl_2$, 700 μM $NaH_2PO_4$, 5 mM $CaCl_2$, 5 mM $NaHCO_3$, 8 mM HEPES, 10 mM glucose, pH 7.4), then pre-stimulated with KCl and loaded as follows: 0.05 mL of $IMR^{32}$ buffer, 0.05 mL of each compound tested diluted in $IMR^{32}$ buffer containing 20 μM nitrendipine (Sigma), and 0.1 mL KCl dissolved in $IMR^{32}$ buffer, plus Fluo-4 were added (3 μM final concentration, Molecular Probes, Eugene, Oreg.). Final test compound concentrations ranged from about 846 μM to about 17 μM, final nitrendipine concentration was 5 μM, and final KCl concentration was 90 mM. After 1 hour, the cells were washed twice with 0.05 mL of each compound tested in nitrendipine-containing IMR32 buffer (no KCl or Fluo-4), and then replaced with 0.1 mL of each compound tested in nitrendipine-containing $IMR^{32}$ buffer. Plates were then transferred to a Fluorimetric Imaging Plate Reader ($FLIPR^{96}$, Molecular Devices, Inc., Sunnyvale, Calif.) for assay. The FLIPR measured basal Fluo-4 fluorescence for 315 seconds (i.e., 5 minutes and 15 seconds), then added 0.1 mL KCl agonist dissolved in IMR32 buffer and measured fluorescence for another 45 seconds. Final test compound concentrations on the cells after FLIPR read ranged from about 846 μM to about 17 μM, final nitrendipine concentration was 5 μM, and final KCl concentration was 90 mM. Data were collected over the entire time course and analyzed using Excel, Graph Pad Prism (version 3.02, Graph Pad, San Diego, Calif.), or an in-house non-linear regression analysis software.

FLIPR Calcium Mobilization Assay for L-type Calcium Channel. One day prior to performing this assay, HEK293 cells stably expressing recombinant rat L-type calcium channel (LTCC) subunits (α1c, α2δ, and β1) were trypsinized, then seeded on poly-D-lysine-coated 96-well clear-bottom black plates (Becton Dickinson, Franklin Lakes, N.J.) at 75,000 cells/well. On the day of the assay, the plates were washed with LTCC wash buffer (127 mM NaCl, 2 mM $MgCl_2$, 700 μM $NaH_2PO_4$, 5 mM $CaCl_2$, 5 mM $NaHCO_3$, 8 mM HEPES, 10 mM glucose, pH 7.4), then loaded with 0.1 mL of LTCC wash buffer containing Fluo-4 (3 μM final concentration, Molecular Probes, Eugene, Oreg.). After 1 hour, the cells were washed with 0.1 mL LTCC wash buffer and resuspended in 0.05 mL LTCC assay buffer (same composition as LTCC wash buffer). Plates were then transferred to a $FLIPR^{96}$ for assay. The FLIPR measured basal Fluo-4 fluorescence for 15 seconds, then added 0.05 mL of each compound tested diluted in LTCC assay buffer at final concentrations ranging from about 846 pM to about 17 μM. Fluo-4 fluorescence was then measured for 5 minutes. 0.1 mL KCl agonist dissolved in LTCC assay buffer was then added to the cells to produce a final concentration of 90 mM KCl, and fluorescence was measured for another 45 seconds. Data were collected over the entire time course and analyzed using Excel, Graph Pad Prism, or an in-house regression analysis software.

Alternative FLIPR Calcium Mobilization Assay for L-type Calcium Channel. Alternatively, the following cell line and procedure may be used for the FLIPR calcium mobilization assay for L-type calcium channel. One day prior to performing this assay, differentiated A7r5 cells are trypsinized, then seeded on tissue culture treated 96-well clear-bottom black plates (Becton Dickinson, Franklin Lakes, N.J.) at a dilution of 1:1 from a confluent T150 $cm^2$ flask. On the day of the assay, the plates are washed with A7r5 wash buffer (127 mM NaCl, 2 mM $MgCl_2$, 700 μM $NaH_2PO_4$, 5 mM $CaCl_2$, 5 mM $NaHCO_3$, 8 mM HEPES, 10 mM glucose, pH 7.4), then loaded with 0.1 mL of A7r5 wash buffer containing Fluo-4 (3 μM final concentration, Molecular Probes, Eugene, Oreg.). After 1 hour, the cells are washed with 0.1 mL A7r5 wash buffer and resuspended in 0.05 mL A7r5 assay buffer that is composed of A7r5 wash buffer plus 50 μM valinomycin (Sigma). Plates are then transferred to a $FLIPR^{96}$ for assay. The FLIPR measures basal Fluo-4 fluorescence for 15 seconds, then adds 0.05 mL of each compound tested diluted in A7r5 assay buffer at final concentrations ranging from about 846 μM to about 17 μM. Fluo-4 fluorescence is then measured for 5 minutes. 0.1 mL KCl agonist dissolved in A7r5 assay buffer is then added to the cells to produce a final concentration of 90 mM KCl, and fluorescence was measured for another 45 seconds. Data were collected over the entire time course and analyzed using Excel, Graph Pad Prism, or an in-house regression analysis software. Cloning of N- and L-type calcium channel subunit open reading frame cDNAs. Five cDNAs encoding subunits of the rat N- or L-type calcium channels were cloned by PCR amplification in order to reconstitute functional channels in a heterologous system. These were the alpha1b (α1b), beta1 (β1), beta3 (β3), alpha2delta (α2δ), and alpha1c (α1c) subunit cDNAs. The alpha1b subunit cDNA has been described by Dubel et al. in NPL25. The beta1 subunit cDNA has been described by Pragnell et al. in NPL26. The beta3 subunit cDNA has been described by Castellano et al. in NPL27. The alpha2 delta subunit cDNA has been described by Kim et al. in NPL28. The alpha1c subunit cDNA has been described by Koch et al. in NPL29. The 7.0 kb cDNA containing the entire a1b open reading frame (ORF) was PCR amplified as two overlapping cDNA fragments, i.e., a 2.7 kb 5' fragment and a 4.4 kb 3' fragment. The 5' fragment was amplified from rat brain cDNA using primers 1 (SEQ ID NO:1, TABLE 1) and 2 (SEQ ID NO:2, TABLE 1), and the 3' fragment was amplified from rat spinal cord cDNA using primers 3 (SEQ ID NO:3, TABLE 1) and 4 (SEQ ID NO:4, TABLE 1). The two fragments were joined by ligation at a common restriction site to create the entire 7.0 kb cDNA. This ORF encodes the protein isoform generated by alternative splicing termed "+A ΔSFMG ΔET" according to the nomenclature of Lin et al. (NPL30). The entire cDNA was sequenced with redundant coverage on both strands. The cDNA was then inserted into the mammalian expression vector pcDNA6.2DEST (Invitrogen, Carlsbad Calif.) by homologous recombination using the Gateway system (Invitrogen).

The 1.8 kb cDNA encoding the β1 subunit, the 1.45 kb cDNA encoding the beta3 subunit, and the 3.3 kb cDNA encoding the alpha2delta subunit were cloned by PCR amplification from rat spinal cord cDNA (β1) or brain cDNA (β3, α2δ). Primers 5 (SEQ ID NO:5, TABLE 1) and 6 (SEQ ID NO:6, TABLE 1) were used for the β1 cDNA amplification; primers 7 (SEQ ID NO:7, TABLE 1) and 8 (SEQ ID NO:8, TABLE 1) were used for the β3 cDNA amplification; and primers 9 (SEQ ID NO:9, TABLE 1) and 10 (SEQ ID NO:10, TABLE 1) were used for the a2δ cDNA amplification. PCR products were subcloned and fully sequenced on both strands.

Clones matching the reference sequence (β1: NM_017346; β3: NM_012828; α2δ: M86621) and the gene's GenBank rat genomic DNA sequences were recombined into the mammalian expression vector pcDNA3.2DEST (β1, β3) or pcDNA3.1-Zeo (α2δ), which had been modified to a vector compatible with the Gateway recombination system using the Gateway vector adaptor kit (Invitrogen). Proper recombination was confirmed by sequencing of recombinogenic regions. For β3 expression vector, proper protein expression was confirmed by Western blot analysis of lysates of transfected HEK293 cells using a rabbit polyclonal antiserum directed against the rat β3 subunit (USA Biological).

The 6.5 kb cDNA encoding the L-type calcium channel α1c subunit was cloned by PCR amplification from rat heart cDNA using primers 11 (SEQ ID NO:11, TABLE 1) and 12 (SEQ ID NO:12, TABLE 1). The PCR fragment was subcloned and fully sequenced on both strands to confirm its identity. A clone matching consensus reference sequence M59786 and rat genomic DNA sequences was recombined into the mammalian expression vector pcDNA6.2DEST. Sequences around the recombinogenic region were sequenced to confirm accurate recombination into the expression vector.

TABLE 1

| PRIMER SEQUENCE | SEQ ID NO. |
|---|---|
| CACC ATG GTC CGC TTC GGG GAC | 1 |
| CCG TTC AGT GGC CTC CTC C | 2 |
| C TAG CAC CAG TGA TCC TGG TCTG | 3 |
| AGT GCG TTG TGA GCG CAG TA | 4 |
| CAC CAT GGT CCA GAA GAG CGG | 5 |
| TCTCAGCGGATGTAGACGCCT | 6 |
| CAC CAT GTA TGA CGA CTC CTA C | 7 |
| GGT GGT CAG TAG CTG TCC TTA GG | 8 |
| CAC CAT GGC TGC TGG CTG CCT | 9 |
| AGA GGG TCA CCA TAG ATA GTG TCT G | 10 |
| CACCATGATTCGGGCCTTCGCT | 11 |
| AGCCTGCGGACTACAGGTTGCTGAC | 12 |

N-type Recombinant Cell Line Development. N-type calcium channel expressing HEK-293 cells were created in two stages. Stage 1 was created as follows. The rat α1b, and β3 cDNA expression constructs (2.5 µg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 µg/mL blasticidin and 500 µg/mL geneticin, and incubated for 3 weeks at 37° C., 5% $CO_2$, 95% humidity. Plates containing ≤1 clone per well were cultured until wells positive for single clones were confluent. Individual clones were then arrayed into columns of a destination 96-well plate, and partly split into 6-well plates for culture maintenance. Array plates were washed once with IMR32 buffer and cells loaded for 1 hour with 0.1 mL of IMR32 buffer containing Fluo-4 (3 µM final concentration, Molecular Probes). Then they were washed twice with 0.1 mL of IMR32 buffer, and replaced with 0.1 mL IMR32 buffer. Plates were then transferred to a FLIPR[96] for assay. The FLIPR measured basal Fluo-4 fluorescence for 315 seconds, then added 0.1 mL KCl agonist dissolved in IMR32 buffer and measured fluorescence for another 45 seconds. Final KCl concentration was 90 mM. Data were collected over the entire time course and analyzed using Excel, Graph Pad Prism, or Activity Base (version 5.1, IDBS, Parsippany, N.J.) software. The clone with the greatest signal-to-noise ratio, best stability of response with passage number, and best adhesion to PDL precoated plates (Becton Dickinson) was expanded, characterized and used for stage 2 cell line development.

Stage 2 of N-type cell line development was carried out as follows. The rat a2δ cDNA expression construct (5 µg each) was transfected into the stage 1 N-type clonal cell line by Lipofectamine Plus reagent (Invitrogen), as per manufacturer's instructions. 24 hours later, cells were split in limiting dilution into multiple 96-well plates in selection media containing 20 µg/mL blasticidin, 500 µg/mL geneticin, and 250 µg/mL zeocin and incubated for 3 weeks at 37° C., 5% $CO_2$, 95% humidity. Plates containing 1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded, characterized and tested in electrophysiology for the best current size, N-type pharmacology, N-type characteristic current-voltage relationship and kinetics as described below.

L-type Recombinant Cell Line Development. L-type calcium channel expressing HEK-293 cells were created in two stages. Stage 1 was created as follows. The rat α1c, and β1 cDNA expression constructs (2.5 µg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 µg/mL blasticidin and 500 µg/mL geneticin, and incubated for 3 weeks at 37° C., 5% $CO_2$, 95% humidity. Plates containing 1 clone per well were cultured until wells positive for single clones were confluent. Individual clones were then arrayed into columns of a destination 96-well plate, and partly split into 6-well plates for culture maintenance. Array plates were washed once with LTCC wash (or assay) buffer and cells loaded for 1 hour with 0.1 mL of LTCC buffer containing Fluo-4 (3 µM final concentration, Molecular Probes). Then they were washed twice with 0.1 mL of LTCC buffer, and replaced with 0.1 mL LTCC buffer. Plates were then transferred to a FLIPR[96] for assay. The FLIPR measured basal Fluo-4 fluorescence for 315 seconds, then added 0.1 mL KCl agonist dissolved in LTCC buffer and measured fluorescence for another 45 seconds. Final KCl concentration was 90 mM. Data were collected over the entire time course and analyzed using Excel, Graph Pad Prism, or Activity Base software. The clone with the greatest signal-to-noise ratio, best stability of response with passage number, and best adhesion to PDL precoated plates (Becton Dickinson) was expanded, characterized and used for stage 2 cell line development.

Stage 2 of L-type cell line development was carried out as follows. The rat a2δ cDNA expression construct (5 µg each) was transfected into the stage 1 L-type clonal cell line by Lipofectamine Plus reagent (Invitrogen), as per manufacturer's instructions. 24 hours later, cells were split in limiting dilution into multiple 96-well plates in selection media containing 20 µg/mL blasticidin, 500 µg/mL geneticin, and 250 µg/mL zeocin and incubated for 3 weeks at 37° C., 5% $CO_2$, 95% humidity. Plates containing ≤1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded and characterized.

N-type Electrophysiology in Recombinant Cells. For electrophysiological recording, the cells expressing α1b, β3 and α2δ subunits were seeded on 35-mm culture Petri dishes at a density of approximately $10^4$ cells/dish and kept in an incubator for up to three days for subsequent recordings. For recordings, the dishes were positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings were made using conventional patch-clamp techniques (NPL31) at room temperature (22-24° C.). The patch-clamp pipettes were pulled from WPI, thick-walled borosilicate glass (WPI, Sarasota, Fla.). Currents were recorded using an Axopatch 200A amplifier (Axon Instruments, Union City, Calif.) and were leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes were back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranged from 2 to 3 MOhm and was compensated by 75-80% by the built-in electronic circuitry.

Currents were elicited by stepping from a holding potential of −90 mV to 0 mV for 20 ms every 20 sec. At the −90 mV membrane voltage about 50% of channels were in the inactivated state, and thus contact with a blocker would involve interaction with both resting and inactivated channels. Every drug was applied at 3 to 4 concentrations increasing in a cumulative manner. Fractional inhibition levels in steady-state were used to draw the partial inhibition concentration curves to get the $IC_{50}$ (i.e. concentration causing 50% reduction in the size of the response) values at −90 mV. Stock solutions of each test compound were prepared using DMSO. Serial dilutions to desired concentrations were done with bath solution; concentration of DMSO in final solutions was 0.1%. Drugs were applied by gravity flow using a plane multi-barrel array shooter positioned 0.5 mm apart from the cell.

All curve fittings were carried out using Origin software (version 5.0, Microcal). A Hill equation was fit to the concentration-inhibition curves to determine $IC_{50}$ values. N-type Electrophysiology in Neuronal Cells. To determine dissociation constants in resting versus inactivated state for N-type calcium channels, neuronal cells that endogenously express N-type calcium channels can be used. For electrophysiological recording, the neuronal cells expressing N-type calcium channels are seeded on 35-mm culture Petri dishes at a density of approximately $10^4$ cells/dish and kept in an incubator for up to three days for subsequent recordings. For recordings, the dishes are positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings are made using conventional patch-clamp techniques (NPL31) at room temperature (22-24° C.). The patch-clamp pipettes are pulled from WPI, thick-walled borosilicate glass (WPI, Sarasota, Fla.). Currents are recorded using an Axopatch 200A amplifier (Axon Instruments, Union City, Calif.) and leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes are back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranges from 2 to 3 MOhm and is compensated by 75-80% by the built-in electronic circuitry.

Currents are elicited by stepping from a holding potential of −90 mV to 0 mV for 20 ms every 10 sec. At the −90 mV membrane voltage a proportion of channels is in the inactivated state, and thus contact with a blocker would involve interaction with both resting and inactivated channels. This protocol is used as a first tier screen. For dissection of two components of inhibition (resting block with the apparent dissociation constant $K_r$ and inactivated state block with $K_i$), steady-state inactivation curves are collected using a double-pulse protocol. Three-second long depolarizing pre-pulse incrementing in 10 mV steps is followed by a 10 ms test pulse to 0 mV. Stock solutions of each test compound are prepared using DMSO. Serial dilutions to desired concentrations are done with bath solution; concentration of DMSO in final solutions is 0.1%. Drugs are applied by gravity flow using a plane multi-barrel array shooter positioned ~1 mm apart from the cell.

All curve fittings can be carried out using Origin software (version 5.0, Microcal). A Hill equation is used to fit the concentration-response curves and to determine $IC_{50}$ values. A Boltzman equation is used to fit inactivation curves, returning half-inactivation voltage, $V_{0.5}$, slope p and the amplitude of current at the most negative voltage where eventually all channels are in the resting state. These parameters are used to calculate the apparent dissociation constants: $K_r=((Ab/Ac)/(1-(Ab/Ac))*\{b\})$ where $\{b\}$ is the drug concentration, Ac is the maximum test current amplitude in control conditions and Ab is the maximum test current amplitude in the presence of a blocker; $=\{b\}/((\exp(-(dx/p))*(1+(\{b\}/K_r))-1)$ where dx is the difference between half-inactivation voltage $V_{0.5}$ in the presence and absence of drug and p is the slope.

In Vivo Pharmacology

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

The compounds can be tested for their antinociceptive activity in the formalin model as described in NPL32. Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (for example, 10% Tween-80 or 0.9% saline) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e., antiallodynic and antihyperalgesic activities) using the Chung model of peripheral neuropathy (NPL33). Male Sprague-Dawley rats weighing between 200-225 g are anesthetized with halothane (1-3% in a mixture of 70% air and 30% oxygen), and their body temperature controlled during anesthesia through use of a homeothermic blanket. A 2-cm dorsal midline incision is then made at the L5 and L6 level, and the para-vertebral muscle groups retracted bilaterally. L5 and L6 spinal nerves are then exposed, isolated, and tightly ligated with 6-0 or 7-0 silk suture. A sham operation is performed exposing the contralateral L5 and L6 spinal nerves, without ligating, as a negative control.

Tactile Allodynia Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration. Mechanical Hyperalgesia Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (NPL34). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

CYP3A4 Fluorescent MBI Test

The CYP3A4 fluorescent MBI test is a test of investigating enhancement of CYP3A4 inhibition of a compound by a metabolism reaction, and the test is performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions are as follows: substrate, 5.6 μmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 μmol/mL, at reaction 6.25 μmol/mL (at 10-fold dilution); test drug concentration, 0.625, 1.25, 2.5, 5, 10, 20 mol/L (six points).

An enzyme in a K-Pi buffer (pH 7.4) and a test drug solution as a pre-reaction solution are added to a 96-well plate at the composition of the pre-reaction, a part of it is transferred to another 96-well plate so that it is 1/10 diluted by a substrate in a K-Pi buffer, NADPH as a co-factor is added to initiate a reaction as an index (without preincubation) and, after a predetermined time of a reaction, acetonitrile/0.5 mol/L Tris (trishydroxyaminomethane)=4/1 is added to stop the reaction. In addition, NADPH is added to a remaining preincubation solution to initiate a preincubation (with preincubation) and, after a predetermined time of a preincubation, a part is transferred to another plate so that it is 1/10 diluted with a substrate and a K-Pi buffer to initiate a reaction as an index. After a predetermined time of a reaction, acetonitrile/0.5 mol/L Tris (trishydroxyaminomethane)=4/1 is added to stop the reaction. For the plate on which each index reaction had been performed, a fluorescent value of 7-HFC which is a metabolite is measured with a fluorescent plate reader. (Ex=420 nm, Em=535 nm). Addition of only DMSO which is a solvent dissolving a drug to a reaction system is adopted as a control (100%), remaining activity (%) is calculated at each concentration of a test drug added as the solution, and $IC_{50}$ is calculated by reverse-presumption by a logistic model using a concentration and an inhibition rate. When a difference between $IC_{50}$ values is 5 μM or more, this is defined as (+), and, when the difference is 3 μM or less, this is defined as (−).

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound is assessed.

The reaction conditions are as follows: substrate, 0.5 μmol/L ethoxyresorufin (CYP1A2), 100 μmol/L, tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution is added to a 96-well plate at the composition as described above, NADPH, as a cofactor is added to initiate metabolism reactions as markers and, after the incubation at 37° C. for 15 minutes, a methanol/acetonitrile=1/1 (v/v) solution is added to stop the reaction. After the centrifugation at 3000 rpm for 15 minutes, resorufin (CYP1A2 metabolite) in the supernatant is quantified by a fluorescent multilabel counter and tributamide hydroxide (CYP2CP metabolite), mephenyloin 4' hydroxide (CYP2C19 metabolite), dextromethorphan (CYP2D6 metabolite), and terfenadine alcohol (CYP3A4 metabolite) are quantified by LC/MS/MS.

Addition of only DMSO being a solvent dissolving a drug to a reaction system is adopted as a control (100%), remaining activity (%) is calculated at each concentration of a test drug added as the solution and $IC_{50}$ is calculated by reverse presumption by a logistic model using a concentration and an inhibition rate.

FAT Test

20 µL of freezing-stored rat typhoid *bacillus* (*Salmonella typhimurium* TA98 strain, TA100 strain) is inoculated on 10 mL of a liquid nutrient medium (2.5% Oxoid nutrient broth No. 2), and this is cultured before shaking at 37° C. for 10 hours. 9 mL of a bacterial solution of the TA98 strain is centrifuged (2000×g, 10 minutes) to remove a culturing solution, the bacteria is suspended in 9 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L), the suspension is added to 110 mL of an Exposure medium (Micro F buffer containing Biotin: 8 µg/mL, histidine: 0.2 µg/mL, glucose: 8 mg/mL), and the TA100 strain is added to 120 mL of the Exposure medium relative to 3.16 mL of the bacterial solution to prepare a test bacterial solution. Each 12 µL of a test substance DMSO solution (8 stage dilution from maximum dose 50 mg/mL at 2-fold ratio), DMSO as a negative control, 50 µg/mL of 4-nitroquinoline-1-oxide DMSO solution for the TA98 strain, 0.25 µg/mL of 2-(furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/mL of 2-aminoanthracene DMSO solution for the TA100 strain under the metabolism activating condition as a positive control, and 588 µL of the test bacterial solution (a mixed solution of 498 µl of the test bacterial solution and 90 µL of S9 mix under the metabolism activating condition) are mixed, and this is shaking-cultured at 37° C. for 90 minutes. 460 µL of the bacterial solution exposed to the test substance is mixed with 2300 µg/mL, of an Indicator medium (Micro F buffer containing biotin: 8 µg/mL, histidine: 0.2 µg/mL, glucose: 8 mg/mL, Bromo Cresol Purple: 37.5 µg/mL), each 50 µL, is dispensed into microplate 48 wells/dose, and this is subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and is assessed by comparing with a negative control group. (−) means that mutagenicity is negative and (+) is positive.

Metabolism Stability Test

Using commercially available pooled human hepatic microsomes, a test compound is reacted for a constant time, a remaining rate is calculated by comparing a reacted sample and an unreacted sample, thereby, a degree of metabolism in liver is assessed. A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution is added to 100 µL of a methanol/acetonitrile=1/1 (v/v), mixed and centrifuged at 3000 rpm for 15 minutes. The test compound in the supernatant is quantified by LC/MS/MS, and a remaining amount of the test compound after the reaction is calculated, letting a compound amount at 0 minute reaction time to be 100%. Hydrolysis reaction is performed in the absence of NADPH and glucuronidation reaction is in the presence of 5 mM UDP-glucuronic acid in place of NADPH, followed by similar operations.

hERG Test

For the purpose of assessing risk of an electrocardiogram QT interval prolongation, effects on delayed rectifier $K^+$ current ($I_{Kr}$), which plays an important role in the ventricular repolarization process, is studied using HEK293 cells expressing human ether-a-go-go related gene (hERG) channel.

After a cell is retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds is recorded. After the generated current is stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2$. $6H_2O$: 1 mmol/L, glucose: 10 mmol/L, HEPES (4-(2-hydroxyethyl)-1-piperazineethanesulfonic acid): 10 mmol/L, pH=7.4) in which the test compound had been dissolved at an objective concentration is applied to the cell under the room temperature condition for 10 minutes. From the recording $I_{Kr}$, an absolute value of the tail peak current is measured based on the current value at the resting membrane potential using an analysis software (DataXpress ver. 1, Molecular Devices Corporation). Further, the % inhibition relative to the tail peak current before application of the test substance is calculated, and compared with the vehicle-applied group (0.1% dimethyl sulfoxide solution) to assess influence of the test substance on $I_{Kr}$.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to mammal, e.g. human, orally at a dose of from about 0.0025 to about 1500 mg per kg body weight of the mammal, or an equivalent amount of a pharmaceutically acceptable salt thereof, per day to treat the particular disorder. A useful oral dose of a compound of the present invention administered to a mammal is from about 0.0025 to about 50 mg per kg body weight of the mammal, or an equivalent amount of the pharmaceutically acceptable salt thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily as one or more tablets, each containing from about 0.01 to about 50 mg of the compound, or an equivalent amount of a pharmaceutically acceptable salt or a solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

The present methods of the invention, such as the method for treating or preventing a disorder responsive to the blockade of calcium channels in an animal in need thereof, can further comprise administering a second therapeutic agent to the animal being administered a compound of Formula I. In one embodiment, the second therapeutic agent is administered in an effective amount.

Effective amounts of the other therapeutic agents are known to those skilled in the art. However, it is well within the skilled artisan's purview to determine the other therapeutic agent's optimal effective-amount range. In one embodiment of the invention, where another therapeutic agent is administered to an animal, the effective amount of the compound of the present invention is less than its effective amount would be where the other therapeutic agent is not administered. In this case, without being bound by theory, it is believed that compounds of the present invention and the other therapeutic agent act synergistically to treat or prevent a disorder or condition. The second therapeutic agent can be, but is not limited to, an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof. Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see NPL35 and NPL36 which are hereby incorporated by reference in their entireties. Suitable Cox-11 inhibitors and 5-lipoxygenase inhibitors, as well as combinations thereof, are described in PTL24, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide. Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines. Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT3 receptor antagonists such as odansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam. Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A compound of the present invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder or condition as defined herein. In one embodiment, a compound of the present invention is administered concurrently with the second therapeutic agent; for example, a single composition comprising both an effective amount of a compound of Formula I, and an effective amount of a second therapeutic agent can be administered. Accodingly, the present invention further provides a pharmaceutical composition comprising a combination of a compound of the present invention, the second therapeutic agent, and a pharmaceutically acceptable carrier. Alternatively, a composition comprising an effective amount of a compound of Formula I and a different composition comprising an effective amount of a second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the other therapeutic agent is administered while the compound of the present invention exerts its preventive or therapeutic effect for treating or preventing a disorder or condition.

A pharmaceutical composition of the present invention is preferably manufactured in a manner which is itself known, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in

EXAMPLES

Example 1

N-(cyclopropylmethyl)-2-(1-(4-(trifluoromethoxy)phenylsulfonyl)piperidin-4-ylidene)acetamide

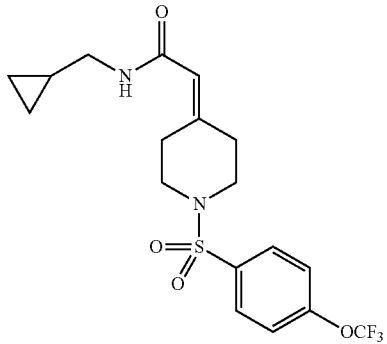 [SMILES: O=C(C=C1CCN(S(=O)(=O)c2ccc(OC(F)(F)F)cc2)CC1)NCC1CC1]

a) 4-(Trifluoromethoxy)benzenesulfonyl chloride (15.0 g, 56.4 mmol) was added over 30 minutes at 0° C. to a solution of 4-piperidone monohydrate hydrochloride (7.22 g, 47.0 mmol) and N,N-diisopropylethylamine (DIPEA, 17.7 ml, 103 mmol) in N,N-dimethylformamide (DMF, 200 ml). The reaction mixture was stirred at room temperature for 3 days. The reaction mixture was quenched with $H_2O$ (800 ml) and the resulting precipitation was collected and washed with $H_2O$ and n-hexane to give 1-(4-(trifluoromethoxy)phenylsulfonyl)piperidin-4-one (11.9 g, 79%) as a pale-yellow solid.

b) Sodium hydride (60%, 0.34 g, 8.53 mmol) was added at 0° C. to a solution of tert-butyl 2-(dimethoxyphosphoryl)acetate (2.15 g, 9.31 mmol) in tetrahydrofuran (THF, 35 ml) and the mixture was stirred for 10 minutes. 1-(4-(trifluoromethoxy)phenylsulfonyl)piperidin-4-one (2.50 g, 7.76 mmol) was added and the whole was stirred at 0° C. for 4 hours. The reaction mixture was quenched with saturated $NH_4Cl$ solution (40 ml), and the aqueous phase was extracted with ethyl acetate (40 ml×2). The combined organic phase was washed with brine (30 ml), dried over $MgSO_4$, filtered and concentrated in vacuo. The residual solid was recrystallized from ethyl acetate/n-hexane to give tert-butyl 2-(1-(4-(trifluoromethoxy)phenylsulfonyl)piperidin-4-ylidene)acetate (3.10 g, 90%) as a pale-yellow solid.

c) Trifluoroacetic acid (5.00 ml, 64.9 mmol) was added at 0° C. to a solution of 2-(1-(4-(trifluoromethoxy)phenylsulfonyl)piperidin-4-ylidene)acetate (2.93g, 6.98 mmol) in $CH_2Cl_2$ (15 ml) and the whole was stirred at 0° C. for 1 hour and room temperature for 2 hours. The reaction mixture was concentrated in vacuo and the residual solid was recrystallized from $CHCl_3$/n-hexane to give 2-(1-(4-(trifluoromethoxy)phenylsulfonyl)piperidin-4-ylidene)acetic acid (2.53g, 97%) as a white solid.

d) Cyclopropylmethylamine (0.065 ml, 0.75 mmol) was added to a solution of 2-(1-(4-(trifluoromethoxy)phenylsulfonyl)piperidin-4-ylidene)acetic acid (183 mg, 0.500 mmol), 1-(3-dimethylaminopropyl)-3-ethylcarbodiimide hydrochloride (115 mg, 0.600 mmol) and 1-hydroxybenzotriazole monohydrate (84 mg, 0.55 mmol) in $CH_2Cl_2$ (5 ml), and the whole was stirred for 12 hours. After the reaction was quenched with saturated $NaHCO_3$ solution (15 ml), the aqueous phase was extracted with $CHCl_3$ (30 ml×2) and the combined organic phase was dried over $MgSO_4$, filtered and concentrated in vacuo. The residue was purified by column chromatography (ethyl acetate/n-hexane: 65/35) to give N-(cyclopropylmethyl)-2-(1-(4-(trifluoromethoxy)phenylsulfonyl)piperidin-4-ylidene)acetamide (102 mg, 49%) as a white solid: LCMS: 419 {M+1}$^+$. $^1$H NMR (DMSO-d$_6$) δ: 0.11 (m, 2H), 0.37 (m, 2H), 0.85 (m, 1H), 2.26 (m, 2H), 2.90-3.05 (m, 8H), 5.67 (s, 1H), 7.62 (d, 2H), 7.90 (d, 2H), 7.96 (t, 1H).

Example 2

N-phenyl-2-(1-(4-(trifluoromethoxy)phenylsulfonyl)piperidin-4-ylidene)Acetamide was Prepared in a Manner Similar to that Described in Example 1:

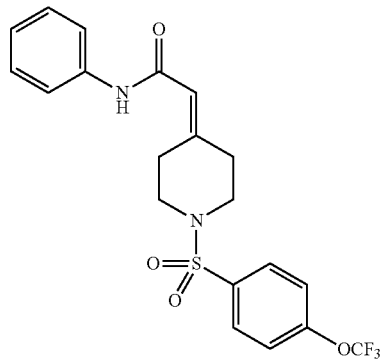

white solid: LCMS: 441 (M+1)$^+$. $^1$H NMR (DMSO-d$_6$) δ: 2.17 (m, 2H), 2.99 (m, 2H), 3.14 (m, 2H), 3.55 (m, 2H), 5.55 (s, 1H), 7.02 (m, 1H), 7.27 (m, 2H), 7.54 (d, 2H), 7.61 (d, 2H), 7.91 (m, 2H), 9.90 (s, 1H).

Example 3

N-benzyl-2-(1-(4-(trifluoromethoxy)phenylsulfonyl)piperidin-4-ylidene)Acetamide was Prepared in a Manner Similar to that Described in Example 1:

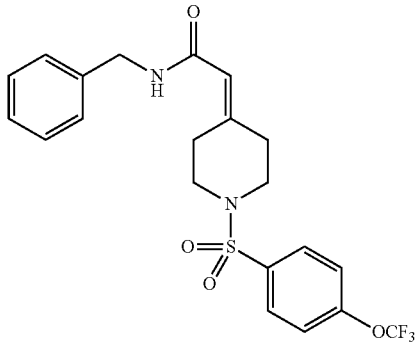 [SMILES: O=C(C=C1CCN(S(=O)(=O)c2ccc(OC(F)(F)F)cc2)CC1)NCc1ccccc1]

white solid: LCMS: 455 (M+1)+. 1H NMR (DMSO-d6) δ: 2.27 (m, 2H), 3.02-3.07 (m, 6H), 4.25 (d, 2H), 5.72 (s, 1H), 7.22 (m, 3H), 7.29 (m, 2H), 7.62 (d, 2H), 7.90 (d, 2H), 8.38 (t, 1H).

Example 4

N-methyl-N-phenyl-2-(1-(4-(trifluoromethoxy)phenylsulfonyl)piperidin-4-ylidene)Acetamide was Prepared in a Manner Similar to that Described in Example 1:

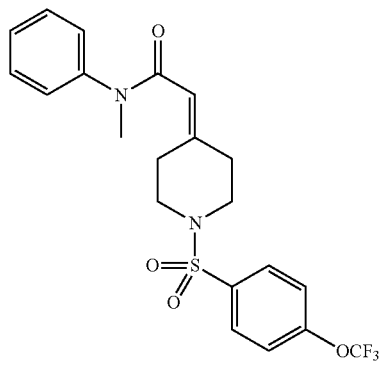 [SMILES: CN(C(=O)C=C1CCN(S(=O)(=O)c2ccc(OC(F)(F)F)cc2)CC1)c1ccccc1]

white solid: LCMS: 455 {M+1}+. 1H NMR (DMSO-d6) δ: 2.09 (m, 2H), 2.69 (m, 2H), 2.86 (m, 4H), 3.17 (s, 3H), 5.51 (s, 1H), 7.20 (m, 3H), 7.31 (m, 2H), 7.65 (d, 2H), 7.86 (d, 2H).

Example 5

N-cyclopropyl-2-(1-(4-(trifluoromethoxy)phenylsulfonyl)piperidin-4-ylidene)Acetamide was Prepared in a Manner Similar to that Described in Example 1:

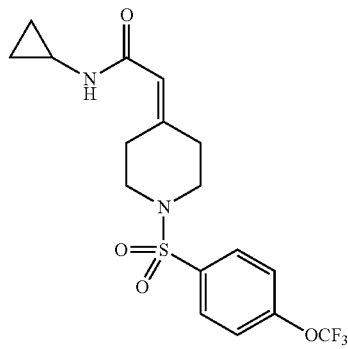 [SMILES: O=C(C=C1CCN(S(=O)(=O)c2ccc(OC(F)(F)F)cc2)CC1)NC1CC1]

white solid: LCMS: 405 {M+1}+. 1H NMR (DMSO-d6) δ: 0.34 (m, 2H), 0.59 (m, 2H), 2.24 (m, 2H), 2.61 (m, 1H), 3.03 (m, 6H), 5.56 (s, 1H), 7.62 (d, 2H), 7.91 (m, 3H).

Example 6

N-(4-chlorophenyl)-2-(1-(4-(trifluoromethoxy)phenylsulfonyl)piperidin-4-ylidene)Acetamide was Prepared in a Manner Similar to that Described in Example 1:

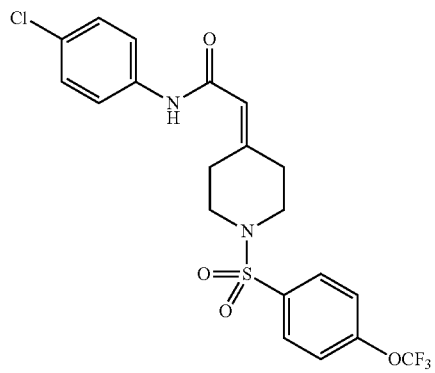 [SMILES: O=C(C=C1CCN(S(=O)(=O)c2ccc(OC(F)(F)F)cc2)CC1)Nc1ccc(Cl)cc1]

white solid: LCMS: 476 {M+1}+. 1H NMR (DMSO-d6) δ: 2.16 (m, 2H), 3.00 (m, 2H), 3.14 (m, 2H), 3.55 (m, 2H), 5.55 (s, 1H), 7.33 (d, 2H), 7.58 (d, 2H), 7.61 (d, 2H), 7.91 (d, 2H), 10.06 (m, 1H).

Example 7

N-(2,2,2-trifluoroethyl)-2-(1-(4-(trifluoromethoxy)phenylsulfonyl)piperidin-4-ylidene)Acetamide was Prepared in a Manner Similar to that Described in Example 1:

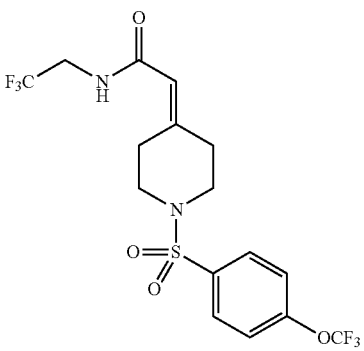 [SMILES: O=C(C=C1CCN(S(=O)(=O)c2ccc(OC(F)(F)F)cc2)CC1)NCC(F)(F)F]

white solid: LCMS: 447 {M+1}⁺. ¹H NMR (DMSO-d₆) δ: 2.30 (m, 2H), 3.04 (m, 6H), 3.89 (m, 2H), 5.74 (s, 1H), 7.62 (d, 2H), 7.90 (d, 2H), 8.53 (t, 1H).

Example 8

N-(2-cyanoethyl)-2-(1-(4-(trifluoromethoxy)phenyl-sulfonyl)piperidin-4-ylidene)Acetamide was Prepared in a Manner Similar to that Described in Example 1:

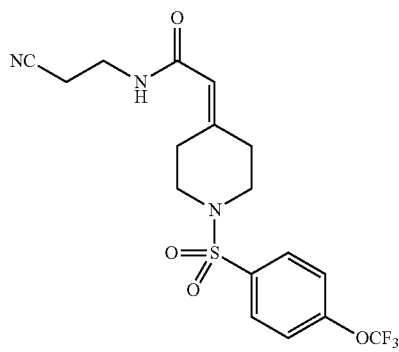 [SMILES: N#CCCNC(=O)C=C1CCN(S(=O)(=O)c2ccc(OC(F)(F)F)cc2)CC1]

white solid: LCMS: 418 {M+1}⁺. ¹H NMR (DMSO-d₆) δ: 2.28 (m, 2H), 2.62 (m, 2H), 3.00-3.06 (m, 6H), 3.27 (m, 2H), 5.67 (s, 1H), 7.62 (d, 2H), 7.90 (d, 2H), 8.27 (t, 1H).

Example 9

N-(4-fluorobenzyl)-2-(1-(4-(trifluoromethoxy)phenylsulfonyl)piperidin-4-ylidene)Acetamide was Prepared in a Manner Similar to that Described in Example 1:

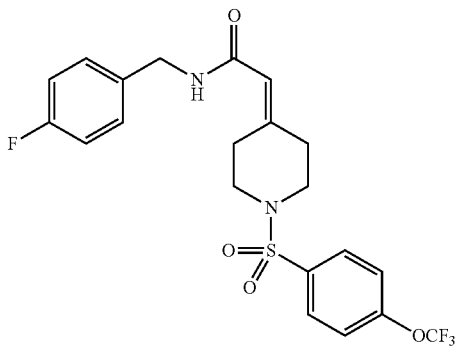

white solid: LCMS: 473 {M+1}⁺. ¹H NMR (DMSO-d₆) δ: 2.28 (m, 2H), 3.03 (m, 6H), 4.23 (d, 2H), 5.71 (s, 1H), 7.11 (m, 2H), 7.25 (m, 2H), 7.62 (d, 2H), 7.90 (d, 2H), 8.41 (t, 1H).

Example 10

N-(4-fluorobenzyl)-N-methyl-2-(1-(4-(trifluoromethoxy)phenylsulfonyl)piperidin-4-ylidene)Acetamide was Prepared in a Manner Similar to that Described in Example 1:

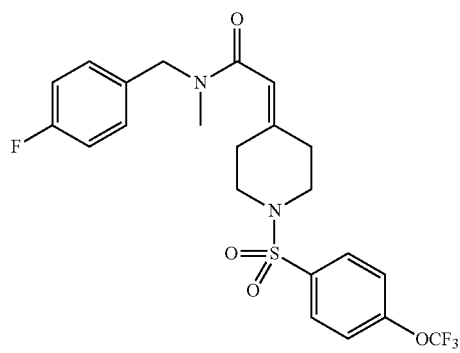 [SMILES: CN(Cc1ccc(F)cc1)C(=O)C=C1CCN(S(=O)(=O)c2ccc(OC(F)(F)F)cc2)CC1]

pale-yellow solid: LCMS: 487 {M+1}⁺. ¹H NMR (DMSO-d₆) δ: 2.29 (m, 1H), 2.35 (m, 1H), 2.57 (m, 1H), 2.65 (m, 1H), 2.77-3.08 (m, 7H), 4.49 (d, 2H), 6.10 (s, 1H), 7.04-7.26 (m, 4H), 7.62 (d, 2H), 7.90 (m, 2H).

Example 11

N-(4-cyanobenzyl)-2-(1-(4-(trifluoromethoxy)phenylsulfonyl)piperidin-4-ylidene)Acetamide was Prepared in a Manner Similar to that Described in Example 1:

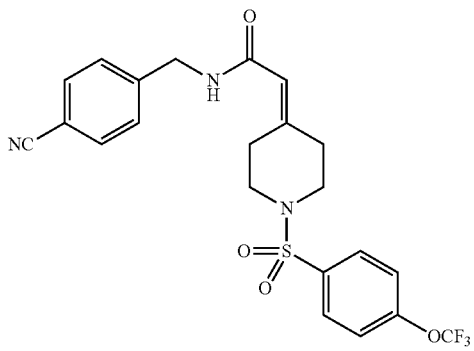 [SMILES: N#Cc1ccc(CNC(=O)C=C2CCN(S(=O)(=O)c3ccc(OC(F)(F)F)cc3)CC2)cc1]

white solid: LCMS: 480 {M+1}+. 1H NMR (DMSO-d6) δ: 2.29 (m, 2H), 3.01-3.07 (m, 6H), 4.31 (d, 2H), 5.73 (s, 1H), 7.50-7.71 (m, 6H), 7.90 (d, 2H), 8.49 (t, 1H).

Example 12

N-(1-(4-fluorophenyl)cyclopropyl)-2-(1-(4-(trifluoromethoxy)phenylsulfonyl)piperidin-4-ylidene)Acetamide was Prepared in a Manner Similar to that Described in Example 1:

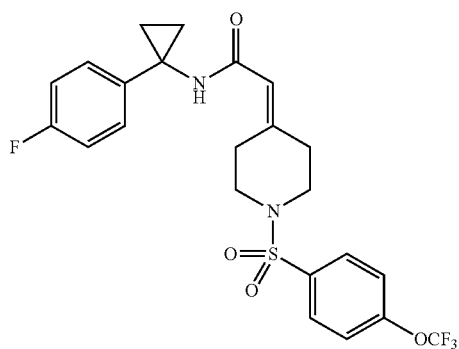 [SMILES: O=C(C=C1CCN(S(=O)(=O)c2ccc(OC(F)(F)F)cc2)CC1)NC1(c2ccc(F)cc2)CC1]

white solid: LCMS: 499 {M+1}+. 1H NMR (DMSO-d6) δ: 1.05-1.11 (m, 4H), 2.26 (m, 2H), 2.98-3.09 (m, 6H), 5.67 (s, 1H), 7.05 (m, 2H), 7.14 (m, 2H), 7.62 (d, 2H), 7.89 (d, 2H), 8.62 (s, 1H).

Example 13

N-(2-cyclopropylethyl)-2-(1-(4-(trifluoromethoxy)phenylsulfonyl)piperidin-4-ylidene)Acetamide was Prepared in a Manner Similar to that Described in Example 1:

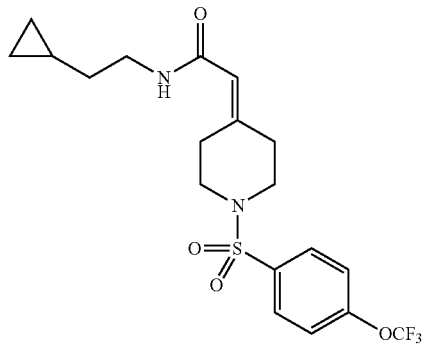 [SMILES: O=C(C=C1CCN(S(=O)(=O)c2ccc(OC(F)(F)F)cc2)CC1)NCCC1CC1]

white solid: LCMS: 433 {M+1}+. 1H NMR (DMSO-d6) δ: 0.00 (m, 2H), 0.37 (m, 2H), 0.64 (m, 1H), 1.27 (m, 2H), 2.25 (m, 2H), 2.99-3.11 (m, 8H), 5.64 (s, 1H), 7.62 (d, 2H), 7.88 (m, 3H).

Example 14

N-(pyridin-3-ylmethyl)-2-(1-(4-(trifluoromethoxy)phenylsulfonyl)piperidin-4-ylidene)Acetamide was Prepared in a Manner Similar to that Described in Example 1:

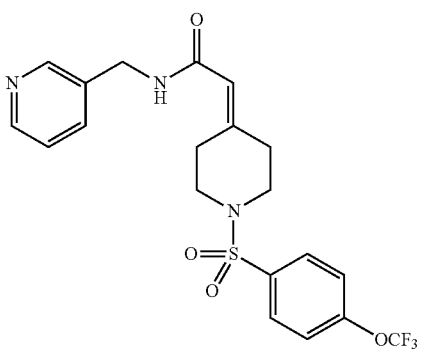 [SMILES: O=C(C=C1CCN(S(=O)(=O)c2ccc(OC(F)(F)F)cc2)CC1)NCc1cccnc1]

white solid: LCMS: 456 {M+1}+. 1H NMR (DMSO-d6) δ: 2.28 (m, 2H), 3.00-3.06 (m, 6H), 4.27 (d, 2H), 5.71 (s, 1H), 7.33 (m, 1H), 7.62 (m, 3H), 7.89 (d, 2H), 8.46 (m, 3H).

Example 15

N-(2-isopropoxyethyl)-2-(1-(4-(trifluoromethoxy)phenylsulfonyl)piperidin-4-ylidene)Acetamide was Prepared in a Manner Similar to that Described in Example 1:

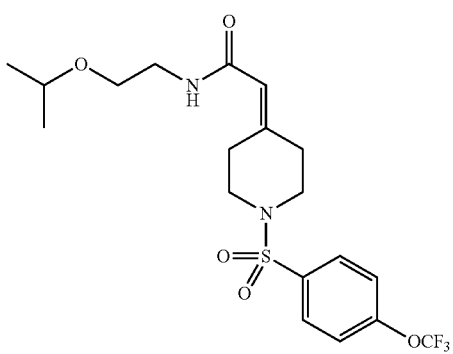 [SMILES: CC(C)OCCNC(=O)C=C1CCN(S(=O)(=O)c2ccc(OC(F)(F)F)cc2)CC1]

white solid: LCMS: 451 {M+1}+. 1H NMR (DMSO-d6) δ: 1.05 (d, 6H), 2.26 (m, 2H), 2.62 (m, 2H), 2.99-3.05 (m, 6H), 3.16 (m, 2H), 3.33 (m, 2H), 3.50 (m, 1H), 5.68 (s, 1H), 7.62 (d, 2H), 7.89 (m, 3H).

Example 16

N-((tetrahydrofuran-2-yl)methyl)-2-(1-(4-(trifluoromethoxy)phenylsulfonyl)piperidin-4-ylidene)Acetamide was Prepared in a Manner Similar to that Described in Example 1:

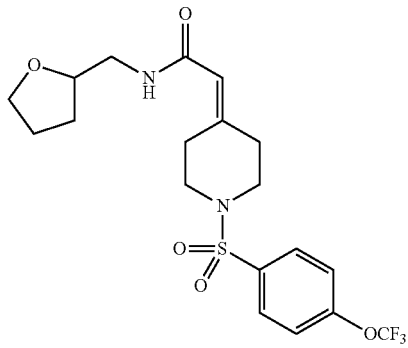 [SMILES: O=C(C=C1CCN(S(=O)(=O)c2ccc(OC(F)(F)F)cc2)CC1)NCC1CCCO1]

white solid: LCMS: 449 {M+1}+. 1H NMR (DMSO-d6) δ: 1.45 (m, 1H), 1.78 (m, 3H), 2.25 (m, 2H), 2.97-3.15 (m, 8H), 3.58 (m, 1H), 3.69-3.81 (m, 2H), 5.70 (s, 1H), 7.62 (d, 2H), 7.92 (m, 3H).

Example 17

N-((tetrahydro-2H-pyran-4-yl)methyl)-2-(1-(4-(trifluoromethoxy)phenylsulfonyl)piperidin-4-ylidene)Acetamide was Prepared in a Manner Similar to that Described in Example 1:

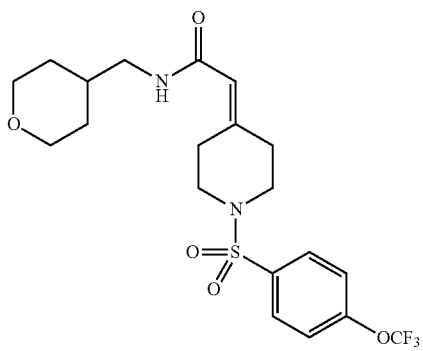 [SMILES: O=C(C=C1CCN(S(=O)(=O)c2ccc(OC(F)(F)F)cc2)CC1)NCC1CCOCC1]

white solid: LCMS: 463 {M+1}+. 1H NMR (DMSO-d6) δ: 1.10 (m, 2H), 1.49 (m, 2H), 1.58 (m, 1H), 2.26 (m, 2H), 2.91-3.05 (m, 8H), 3.21 (m, 2H), 3.80 (m, 2H), 5.67 (s, 1H), 7.62 (d, 2H), 7.90 (m, 3H).

Example 18

N-phenoxy-2-(1-(4-(trifluoromethoxy)phenylsulfonyl)piperidin-4-ylidene)Acetamide was Prepared in a Manner Similar to that Described in Example 1:

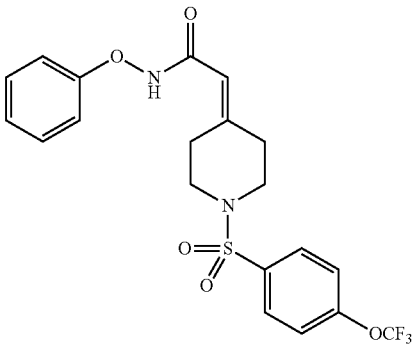 [SMILES: O=C(C=C1CCN(S(=O)(=O)c2ccc(OC(F)(F)F)cc2)CC1)NOc1ccccc1]

white solid: LCMS: 457 {M+1}+. 1H NMR (DMSO-d6) δ: 2.35 (m, 2H), 2.97-3.08 (m, 6H), 5.68 (s, 1H), 6.98 (m, 3H), 7.30 (m, 2H), 7.63 (d, 2H), 7.91 (d, 2H), 11.75 (s, 1H).

Example 19 methyl 2-(4-fluorophenyl)-2-(2-(1-(4-(trifluoromethoxy)phenylsulfonyl)piperidin-4-ylidene)acetamido)Acetate was Prepared in a Manner Similar to that Described in Example 1:

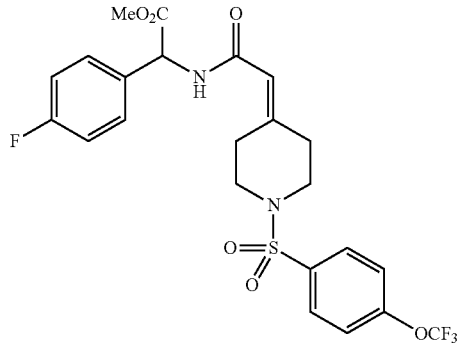 [SMILES: COC(=O)C(NC(=O)C=C1CCN(S(=O)(=O)c2ccc(OC(F)(F)F)cc2)CC1)c1ccc(F)cc1]

colorless amorphous: LCMS: 531 {M+1}+. 1H NMR (DMSO-d6) δ: 2.28 (m, 2H), 3.00-3.05 (m, 6H), 3.60 (s, 3H), 5.42 (d, 1H), 5.83 (s, 1H), 7.20 (m, 2H), 7.40 (m, 2H), 7.62 (d, 2H), 7.89 (d, 2H), 8.74 (d, 1H).

Example 20

N-(1-(4-fluorophenyl)-2-hydroxyethyl)-2-(1-(4-(trifluoromethoxy)phenylsulfonyl)piperidin-4-ylidene)acetamide

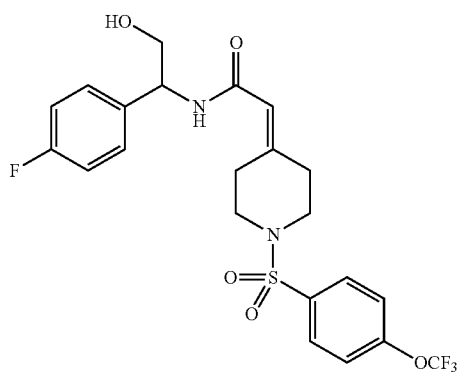 [SMILES: O=C(C=C1CCN(S(=O)(=O)c2ccc(OC(F)(F)F)cc2)CC1)NC(CO)c1ccc(F)cc1]

A solution of lithium borohydride (42.3 mg, 1.94 mmol) in THF (3 ml) was added at 0° C. to a solution of methyl 2-(4-fluorophenyl)-2-(2-(1-(4-(trifluoromethoxy)phenylsulfonyl)piperidin-4-ylidene)acetamido)acetate prepared in EXAMPLE 19 (350 mg, 0.647 mmol) in THF (7 ml) and the whole was stirred at room temperature for 18 hours. The reaction mixture was quenched with H$_2$O and the resulting precipitation was collected and washed with H$_2$O and n-hexane to give N-(1-(4-fluorophenyl)-2-hydroxyethyl)-2-(1-(4-(trifluoromethoxy)phenylsulfonyl)piperidin-4-ylidene)acetamide (298 mg, 92%) as a white solid: LCMS: 503 {M+1}$^+$. $^1$H NMR (DMSO-d$_6$) δ: 2.27 (m, 2H), 2.98-3.06 (m, 6H), 3.51 (m, 2H), 4.84 (m, 2H), 5.78 (s, 1H), 7.10 (m, 2H), 7.29 (m, 2H), 7.61 (d, 2H), 7.89 (d, 2H), 8.29 (d, 1H).

Example 21

N-cyclopropyl-2-(2-(1-(4-(trifluoromethoxy)phenylsulfonyl)piperidin-4-ylidene)acetamido)acetamide

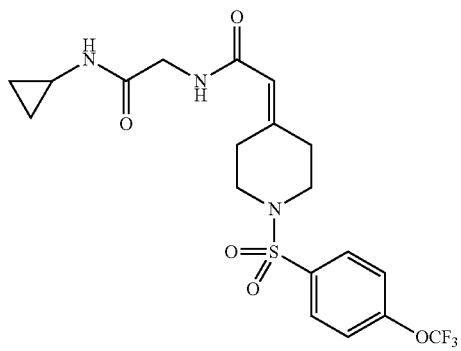 [SMILES: O=C(C=C1CCN(S(=O)(=O)c2ccc(OC(F)(F)F)cc2)CC1)NCC(=O)NC1CC1]

a) A mixture of 2-(1-(4-(trifluoromethoxy)phenylsulfonyl)piperidin-4-ylidene)acetic acid prepared in EXAMPLE 1c (548 mg, 1.50 mmol), glycine tert-butyl ester (203 mg, 1.50 mmol), 1-(3-dimethylaminopropyl)-3-ethylcarbodiimide hydrochloride (345 mg, 1.80 mmol), 1-hydroxybenzotriazole monohydrate (253 mg, 1.65 mmol) and triethylamine (0.252 ml, 1.80 mmol) in CH$_2$Cl$_2$ (15 ml) was stirred for 4 hours. After the reaction was quenched with saturated NaHCO$_3$ solution (20 ml), the aqueous phase was extracted with CHCl$_3$ (30 ml×2) and the combined organic phase was dried over MgSO$_4$, filtered and concentrated in vacuo. The residue was purified by column chromatography (ethyl acetate/n-hexane:50/50) to give tert-butyl 2-(2-(1-(4-(trifluoromethoxy)phenylsulfonyl)piperidin-4-ylidene)acetamido)acetate (368 mg, 51%) as a colorless, amorphous compound.

b) Trifluoroacetic acid (2 ml) was added to a solution of tert-butyl 2-(2-(1-(4-(trifluoromethoxy)phenylsulfonyl)piperidin-4-ylidene)acetamido)acetate (360 mg, 0.752 mmol) in CH$_2$Cl$_2$ (4 ml) and the whole was stirred for 1 hour. The reaction mixture was concentrated in vacuo and the residual solid was recrystallized from ethyl acetate/n-hexane to give 2-(2-(1-(4-(trifluoromethoxy)phenylsulfonyl)piperidin-4-ylidene)acetamido)acetic acid (290 mg, 91%) as a white solid.

c) Cyclopropylmethylamine (0.0367 ml, 0.521 mmol) was added to a solution of 2-(2-(1-(4-(trifluoromethoxy)phenylsulfonyl)piperidin-4-ylidene)acetamido)acetic acid (100 mg, 0.237 mmol), 1-(3-dimethylaminopropyl)-3-ethylcarbodiimide hydrochloride (54.5 mg, 0.284 mmol) and 1-hydroxybenzotriazole monohydrate (39.9 mg, 0.260 mmol) in CH$_2$Cl$_2$ (5 ml), and the whole was stirred for 2 hours. After the reaction was quenched with saturated NaHCO$_3$ solution (15 ml), the aqueous phase was extracted with ethyl acetate (50 ml×2) and the combined organic phase was washed with brine, dried over MgSO$_4$, filtered and concentrated in vacuo. The residual solid was recrystallized from ethyl acetate/n-hexane to give N-cyclopropyl-2-(2-(1-(4-(trifluoromethoxy)phenylsulfonyl)piperidin-4-ylidene)acetamido)acetamide (104 mg, 95%) as a white solid: LCMS: 462 {M+1}$^+$. $^1$H NMR (DMSO-d$_6$) δ: 0.38 (m, 2H), 0.59 (m, 2H), 2.28 (m, 2H), 2.59 (m, 1H), 2.99-3.06 (m, 6H), 3.61 (d, 2H), 5.74 (s, 1H), 7.62 (d, 2H), 7.90 (m, 3H), 8.04 (t, 1H).

Example 22

N-(cyclopropylmethyl)-2-(1-(3-(trifluoromethyl)phenylsulfonyl)piperidin-4-ylidene)acetamide

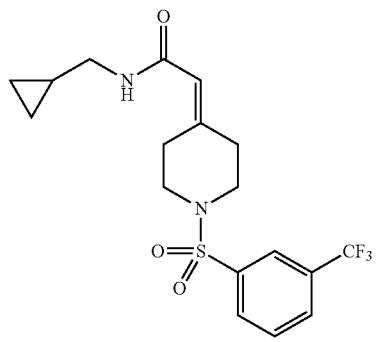 [SMILES: O=C(C=C1CCN(S(=O)(=O)c2cccc(C(F)(F)F)c2)CC1)NCC1CC1]

a) Trifluoroacetic anhydride (24.0 g, 144 mmol) was added over 30 minutes at 0° C. to a solution of 4-piperidone monohydrate hydrochloride (8.00 g, 52.0 mmol) and triethylamine (17.3g, 172 mmol) in CH$_2$Cl$_2$ (260 ml). The reaction mixture was stirred at room temperature for 2 hours. After the reaction mixture was quenched with H₂O (150 ml), the aqueous phase was extracted with CHCl₃ (100 ml×2) and the combined organic phase was dried over MgSO₄, filtered and concentrated in vacuo. The residue was purified by column chromatography (ethyl acetate/n-hexane:50/50) to give 1-(2,2,2-trifluoroacetyl)piperidin-4-one (9.82 g, 97%) as a white solid.

b) Sodium hydride (60%, 1.03g, 25.6 mmol) was added at 0° C. to a solution of tert-butyl 2-(dimethoxyphosphoryl)acetate (5.74 g, 25.6 mmol) in THF (60 ml) and the mixture was stirred for 30 minutes. A solution of 1-(2,2,2-trifluoroacetyl)piperidin-4-one (5.00 g, 25.6 mmol) in THF (50 ml) was added over 30 minutes and the whole was stirred at 0° C. for 1 hour. The reaction mixture was quenched with saturated NH₄Cl solution (50 ml), and the aqueous phase was extracted with ethyl acetate (100 ml×2). The combined organic phase was washed with brine, dried over MgSO₄, filtered and concentrated in vacuo. The residue was purified by column chromatography (ethyl acetate/n-hexane: 25/75) to give tert-butyl 2-(1-(2,2,2-trifluoroacetyl)piperidin-4-ylidene)acetate (6.13g, 82%) as a pale yellow oil.

c) Trifluoroacetic acid (6.55 ml, 85.0 mmol) was added to a solution of tert-butyl 2-(1-(2,2,2-trifluoroacetyl)piperidin-4-ylidene)acetate (4.99 g, 17.0 mmol) in CH₂Cl₂ (20 ml) and the whole was stirred for 14 hours. The reaction mixture was concentrated in vacuo and the residue was treated with H₂O, extracted with CHCl₃ (50 ml×3). The combined organic phase was dried over MgSO₄, filtered and concentrated in vacuo. The residual solid was triturated with n-hexane to give 2-(1-(2,2,2-trifluoroacetyl)piperidin-4-ylidene)acetic acid (4.02 g, 100%) as a white solid.

d) Cyclopropylmethylamine (1.34 ml, 15.0 mmol) was added to a solution of 2-(1-(2,2,2-trifluoroacetyl)piperidin-4-ylidene)acetic acid (2.37 g, 10.0 mmol), 1-(3-dimethylaminopropyl)-3-ethylcarbodiimide hydrochloride (2.30 g, 12.0 mmol) and 1-hydroxybenzotriazole monohydrate (1.69 g, 11.0 mmol) in CH₂Cl₂ (50 ml), and the whole was stirred for 3 hours. After the reaction was quenched with saturated NaHCO₃ solution (50 ml), the aqueous phase was extracted with ethyl acetate (80 ml×2) and the combined organic phase was washed with brine, dried over MgSO₄, filtered and concentrated in vacuo to give N-(cyclopropylmethyl)-2-(1-(2,2,2-trifluoroacetyl)piperidin-4-ylidene)acetamide (3.14 g, 99%) as a pale-yellow oil.

e) K₂CO₃ (4.09 g, 29.6 mmol) was added to a solution of N-(cyclopropylmethyl)-2-(1-(2,2,2-trifluoroacetyl)piperidin-4-ylidene)acetamide (3.13g, 9.87 mmol) in methanol (30 ml) at 0° C. and the whole was stirred at 0° C. for 2 hours and room temperature for 2 hours. The reaction mixture was then filtered and the filtrate was concentrated in vacuo. The residue was treated with H₂O (80 ml), extracted with CHCl₃/MeOH (90/10, 80 ml×6), dried over MgSO₄, filtered and concentrated in vacuo. The residue was dissolved in 1,4-dioxane (30 ml) and treated with 4 N HCl solution in 1,4-dioxane (10 ml) at 0° C. The mixture was concentrated in vacuo and the residual solid was triturated with methanol/ethyl acetate to give N-(cyclopropylmethyl)-2-(piperidin-4-ylidene)acetamide hydrochloride (1.98 g, 87%) as a white solid.

f) A solution of 3-(trifluoromethyl)benzenesulfonyl chloride (0.0644 ml, 0.381 mmol) in CH₂Cl₂ (2 ml) was added at 0° C. to a solution of N-(cyclopropylmethyl)-2-(piperidin-4-ylidene)acetamide hydrochloride (80.0 mg, 0.347 mmol) and DIPEA (0.127 ml, 0.728 mmol) in CH₂Cl₂ (3 ml). After the reaction mixture was stirred at 0° C. for 30 minutes and quenched with saturated NaHCO₃ solution (10 ml), the aqueous phase was extracted with CHCl₃ (30 ml×2) and the combined organic phase was dried over MgSO₄, filtered and concentrated in vacuo. The residue was purified by column chromatography (ethyl acetate/n-hexane:70/30) and the solid was triturated with ethyl acetate/n-hexane to give N-(cyclopropylmethyl)-2-(1-(3-(trifluoromethyl)phenylsulfonyl)piperidin-4-ylidene)acetamide (136 mg, 97%) as a white solid: LCMS: 403 {M+1}⁺. ¹H NMR (DMSO-d₆) δ: 0.11 (m, 2H), 0.37 (m, 2H), 0.86 (m, 1H), 2.26 (m, 2H), 2.89-3.09 (m, 8H), 5.67 (s, 1H), 7.88-8.13 (m, 5H).

Example 23

2-(1-(3-chlorophenylsulfonyl)piperidin-4-ylidene)-N-(cyclopropylmethyl)Acetamide was Prepared in a Manner Similar to that Described in Example 22:

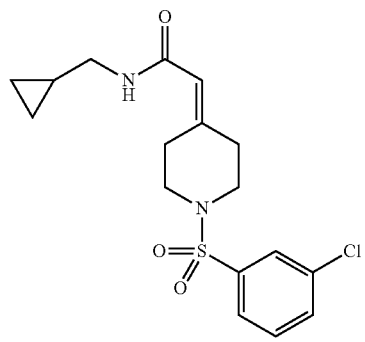 [SMILES: O=C(C=C1CCN(S(=O)(=O)c2cccc(Cl)c2)CC1)NCC1CC1]

white solid: LCMS: 369 {M+1}⁺. ¹H NMR (DMSO-d₆) δ: 0.11 (m, 2H), 0.37 (m, 2H), 0.85 (m, 1H), 2.25 (m, 2H), 2.90-3.07 (m, 8H), 5.67 (s, 1H), 7.65-7.81 (m, 4H), 7.96 (t, 1H).

Example 24

N-(cyclopropylmethyl)-2-(1-(3-fluoro-5-(trifluoromethyl)phenylsulfonyl)piperidin-4-ylidene)Acetamide was Prepared in a Manner Similar to that Described in Example 22:

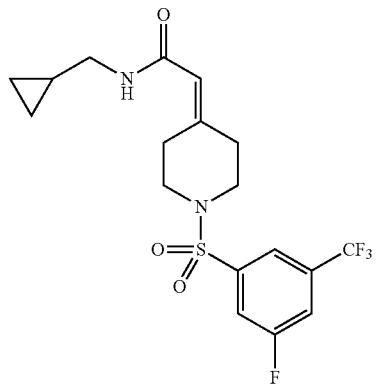 [SMILES: O=C(C=C1CCN(S(=O)(=O)c2cc(F)cc(C(F)(F)F)c2)CC1)NCC1CC1]

white solid: LCMS: 421 {M+1}+. 1H NMR (DMSO-d6) δ: 0.11 (m, 2H), 0.37 (m, 2H), 0.85 (m, 1H), 2.25 (m, 2H), 2.90-3.14 (m, 8H), 5.68 (s, 1H), 7.84 (m, 1H), 7.97 (m, 2H), 8.14 (m, 1H).

Example 25

2-(1-(4-chlorophenylsulfonyl)piperidin-4-ylidene)-N-(cyclopropylmethyl)Acetamide was Prepared in a Manner Similar to that Described in Example 22:

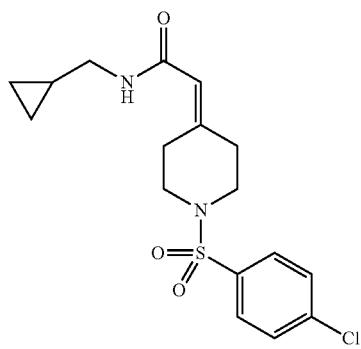 [SMILES: O=C(C=C1CCN(S(=O)(=O)c2ccc(Cl)cc2)CC1)NCC1CC1]

white solid: LCMS: 369 {M+1}+. 1H NMR (DMSO-d6) δ: 0.11 (m, 2H), 0.37 (m, 2H), 0.85 (m, 1H), 2.26 (m, 2H), 2.89-3.03 (m, 8H), 5.66 (s, 1H), 7.70 (d, 2H), 7.76 (d, 2H), 7.95 (t, 1H).

Example 26

N-(cyclopropylmethyl)-2-(1-(4-(trifluoromethyl)phenylsulfonyl)piperidin-4-ylidene)Acetamide was Prepared in a Manner Similar to that Described in Example 22:

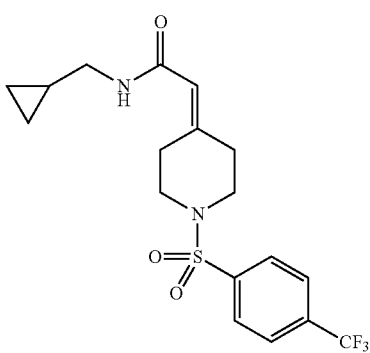 [SMILES: O=C(C=C1CCN(S(=O)(=O)c2ccc(C(F)(F)F)cc2)CC1)NCC1CC1]

white solid: LCMS: 403 {M+1}+. 1H NMR (DMSO-d6) δ: 0.11 (m, 2H), 0.37 (m, 2H), 0.84 (m, 1H), 2.26 (m, 2H), 2.89-3.07 (m, 8H), 5.67 (s, 1H), 7.96-8.03 (m, 5H).

Example 27

2-(1-(5-chlorothiophen-2-ylsulfonyl)piperidin-4-ylidene)-N-(cyclopropylmethyl)Acetamide was Prepared in a Manner Similar to that Described in Example 22:

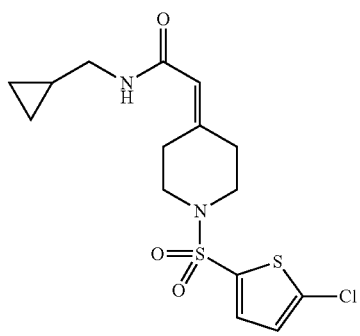 [SMILES: O=C(C=C1CCN(S(=O)(=O)c2ccc(Cl)s2)CC1)NCC1CC1]

white solid: LCMS: 375 {M+1}+. 1H NMR (DMSO-d6) δ: 0.12 (m, 2H), 0.37 (m, 2H), 0.86 (m, 1H), 2.30 (m, 2H), 2.91-3.11 (m, 8H), 5.70 (s, 1H), 7.36 (m, 1H), 7.57 (m, 1H), 7.99 (t, 1H).

Example 28

2-(1-(bis(4-fluorophenyl)methyl)piperidin-4-ylidene)-N-(cyclopropylmethyl)acetamide

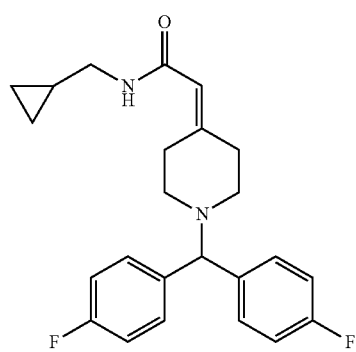 [SMILES: O=C(C=C1CCN(C(c2ccc(F)cc2)c2ccc(F)cc2)CC1)NCC1CC1]

A mixture of N-(cyclopropylmethyl)-2-(piperidin-4-ylidene)acetamide hydrochloride (80.0 mg, 0.347 mmol) prepared in EXAMPLE 22e, 4,4'-difluorobenzhydryl chloride (0.105 ml, 0.555 mmol), K2CO3 (105 mg, 0.763 mmol) and KI (5.8 mg, 0.035 mmol) in acetonitrile (5 ml) was stirred under reflux for 12 hours. The reaction was quenched with H2O (20 ml), extracted with chloroform (30 ml×2), dried over MgSO4 and concentrated in vacuo. The residue was purified by column chromatography (ethyl acetate/hexane:30/70 to 50/50) to give 2-(1-(bis(4-fluorophenyl)methyl)piperidin-4-ylidene)-N-(cyclopropylmethyl)acetamide (107 mg, 78%) as a white solid: LCMS: 397 {M+1}+. 1H NMR (DMSO-d6) δ: 0.11 (m, 2H), 0.38 (m, 2H), 0.87 (m, 1H), 2.22 (m, 2H), 2.32 (m, 2H), 2.36 (m, 2H), 2.93 (m, 4H), 4.47 (s, 1H), 5.61 (s, 1H), 7.13 (m, 4H), 7.43 (m, 4H), 7.87 (t, 1H).

Example 29

N-(cyclopropylmethyl)-2-(1-(1-(4-fluorophenyl)cyclopropyl)piperidin-4-ylidene)acetamide

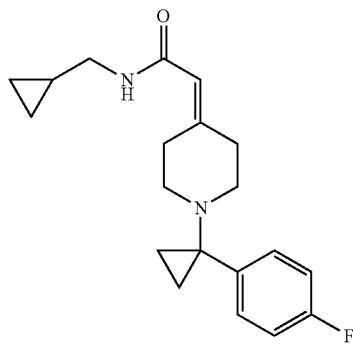 [SMILES: O=C(C=C1CCN(C2(c3ccc(F)cc3)CC2)CC1)NCC1CC1]

a) Ethylmagnesium bromide (3.0 M in diethyl ether, 13.2 ml, 39.6 mmol) was added at −70° C. over 30 minutes to a solution of 4-fluorobenzonitrile (2.18 g, 18.0 mmol) and tetraisopropoxytitanium (5.80 ml, 19.8 mmol) in diethyl ether (90 ml), and the whole was stirred at room temperature for 1.5 hours. Boranetrifluoride diethyl ether complex (4.56 ml, 36.0 mmol) was added over 15 minutes to the reaction mixture and the whole was stirred at room temperature for 1.5 hours. 1 N aqueous HCl solution (54 ml) and diethyl ether (150 ml) were added to the reaction mixture, and the whole was poured into aqueous 10% NaOH solution (180 ml), extracted with diethyl ether (250 ml×2), dried over $Na_2SO_4$, filtered and concentrated in vacuo. The residue was purified by column chromatography (diethyl ether) to give 1-(4-fluorophenyl)cyclopropanamine (1.86 g, 69%).

b) A solution of 1-benzyl-1-methyl-4-oxopiperidinium iodide (427 mg, 1.29 mmol) in ethanol-$H_2O$ (1:1, 4 ml) was added to the solution of 1-(4-fluorophenyl)cyclopropanamine (150 mg, 0.992 mmol) and $K_2CO_3$ (13.7 mg, 0.099 mmol) in ethanol (3 ml) at 80° C. and stirred for 2 hours. The reaction was quenched with $H_2O$ (20 ml), extracted with diethyl ether (30 ml×3), washed with brine, dried over $Na_2SO_4$, filtered and concentrated in vacuo. The residue was purified by column chromatography (ethyl acetate/hexane:30/70 to 50/50) to give 1-(1-(4-fluorophenyl)cyclopropyl)piperidin-4-one (180 mg, 77%) as a pale yellow solid.

c) Sodium hydride (60%, 32 mg, 0.80 mmol) was added at 0° C. to a solution of tert-butyl 2-(dimethoxyphosphoryl)acetate (180 mg, 0.804 mmol) in THF (5 ml) and the mixture was stirred for 10 minutes. A solution of 1-(1-(4-fluorophenyl)cyclopropyl)piperidin-4-one (173 mg, 0.730 mmol) in THF (5 ml) was added and the whole was stirred at room temperature for 18 hours. After the reaction mixture was concentrated in vacuo, the residue was treated with $H_2O$ (10 ml), extracted with ethyl acetate (30 ml×2). The combined organic phase was washed with brine, dried over $MgSO_4$, filtered and concentrated in vacuo. The residue was purified by column chromatography (ethyl acetate/n-hexane:5/95 to 15/85) to give tert-butyl 2-(1-(1-(4-fluorophenyl)cyclopropyl)piperidin-4-ylidene)acetate (237 mg, 98%) as a white solid.

d) 4 N HCl solution in 1,4-dioxane (15 ml) was added to a solution of tert-butyl 2-(1-(1-(4-fluorophenyl)cyclopropyl)piperidin-4-ylidene)acetate (230 mg, 0.694 mmol) in $CH_2Cl_2$ (2 ml) and the whole was refluxed for 2 hours. The mixture was concentrated in vacuo and the residual solid was triturated with diethyl ether to give 2-(1-(1-(4-fluorophenyl)cyclopropyl)piperidin-4-ylidene)acetic acid hydrochloride (79 mg, 37%) as a white solid.

e) 1-(3-Dimethylaminopropyl)-3-ethylcarbodiimide hydrochloride (149 mg, 0.779 mmol) and cyclopropylmethylamine (0.0840 ml, 0.974 mmol) were added to a solution of 2-(1-(1-(4-fluorophenyl)cyclopropyl)piperidin-4-ylidene)acetic acid hydrochloride (70.8 mg, 0.227 mmol), triethylamine (0.108 ml, 0.779 mmol), and 1-hydroxybenzotriazole monohydrate (109 mg, 0.714 mmol) in $CH_2Cl_2$ (5 ml), and the whole was stirred for 5 hours. After the reaction was quenched with saturated $NaHCO_3$ solution (10 ml), the aqueous phase was extracted with ethyl acetate (30 ml×2) and the combined organic phase was dried over $MgSO_4$, filtered and concentrated in vacuo. The residue was purified by column chromatography (ethyl acetate/n-hexane: 75/25 to 100/0) to give N-(cyclopropylmethyl)-2-(1-(1-(4-fluorophenyl)cyclopropyl)piperidin-4-ylidene)acetamide (66 mg, 89%) as a white solid: LCMS: 329 ${M+1}^+$. $^1$H NMR (DMSO-$d_6$) δ: 0.10 (m, 2H), 0.36 (m, 2H), 0.75-0.89 (m, 5H), 2.10 (m, 2H), 2.40 (m, 2H), 2.46 (m, 2H), 2.82-2.90 (m, 4H), 5.51 (s, 1H), 7.12 (m, 2H), 7.28 (m, 2H), 7.82 (t, 1H).

Example 30

N-(cyclopropylmethyl)-2-(1-(2,2,2-trifluoro-1-(4-fluorophenyl)ethyl)piperidin-4-ylidene)acetamide

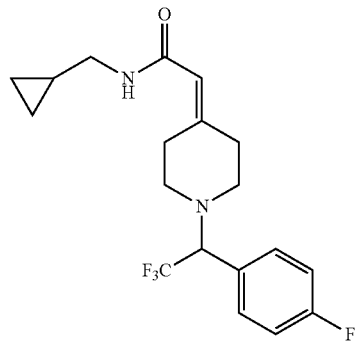 [SMILES: O=C(C=C1CCN(C(c2ccc(F)cc2)C(F)(F)F)CC1)NCC1CC1]

A solution of $TiCl_4$ (0.0299 ml, 0.271 mmol) in $CH_2Cl_2$ (0.5 ml) was added to a solution of N-(cyclopropylmethyl)-2-(piperidin-4-ylidene)acetamide hydrochloride (125 mg, 0.542 mmol) prepared in EXAMPLE 22e, triethylamine (0.225 ml, 1.63 mmol) and 2,2,2,4'-tetrafluoroacetophenone (0.0770 ml, 0.542 mmol) in $CH_2Cl_2$ (3.5 ml), and the whole was stirred for 9 hours. A solution of sodium cyanoborohydride (102 mg, 1.63 mmol) in methanol (1 ml) was added to the reaction mixture and the whole was stirred for 30 minutes. After the reaction was quenched with aqueous 2 N NaOH solution (15 ml), the aqueous phase was extracted with ethyl acetate (30 ml×2) and the combined organic phase was dried over $MgSO_4$, filtered and concentrated in vacuo. The residue was purified by column chromatography (ethyl acetate/n-hexane: 35/65 to 55/45) to give N-(cyclopropylmethyl)-2-(1-(2,2,2-trifluoro-1-(4-fluorophenyl)ethyl)piperidin-4- ylidene)acetamide (52 mg, 26%) as a yellow solid: LCMS: 371 {M+1}$^+$. $^1$H NMR (DMSO-d$_6$) δ: 0.11 (m, 2H), 0.37 (m, 2H), 0.85 (m, 1H), 2.17 (m, 2H), 2.43-2.68 (m, 4H), 2.91 (m, 4H), 4.70 (m, 1H), 5.57 (s, 1H), 7.26 (m, 2H), 7.45 (m, 2H), 7.87 (t, 1H).

Example 31

N-(cyclopropylmethyl)-2-(1-(2-(3-(trifluoromethyl) phenyl)propan-2-yl)piperidin-4-ylidene)acetamide

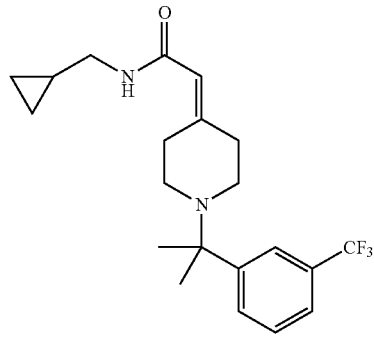 [SMILES: CC(C)(c1cccc(C(F)(F)F)c1)N1CCC(=CC(=O)NCC2CC2)CC1]

a) Tetraisopropoxytitanium (2.75 ml, 10.0 mmol) was added to a solution of 1,4-dioxa-8-azaspiro{4.5}decane (1.43g, 10.0 mmol) and 3'-(trifluoromethyl)phenylacetophenone (1.88 g, 10.0 mmol) in CH$_2$Cl$_2$ (25 ml), and the whole was stirred for 22 hours. Diethylaluminum cyanide (1.0 M in toluene, 10.0 ml, 10.0 mmol) was added to the reaction mixture and the whole was stirred for 27 hours. After the reaction was quenched with saturated NaHCO$_3$ solution (15 ml), the resulting solid was filtered off and washed with CHCl$_3$, and the filtrate was concentrated in vacuo to give a crude product of 2-(1,4-dioxa-8-azaspiro{4.5}decan-8-yl)-2-(3-(trifluoromethyl)phenyl)propanenitrile (3.36 g) as a yellow oil.

b) Methylmagnesium bromide (3.0 M in diethyl ether, 7.50 ml, 22.5 mmol) was added over 10 minutes to a solution of the crude product of 2-(1,4-dioxa-8-azaspiro{4.5}decan-8-yl)-2-(3-(trifluoromethyl)phenyl)propanenitrile (1.93 g) in THF (100 ml) at 0° C., and the whole was stirred at room temperature for 2 days. After the reaction mixture was poured into saturated NH$_4$Cl solution (50 ml), the aqueous phase was extracted with ethyl acetate (150 ml and 100 ml) and the combined organic phase was washed with brine, dried over MgSO$_4$, filtered and concentrated in vacuo. The residue was purified by column chromatography (ethyl acetate/n-hexane:10/90 to 30/70) to give 8-(2-(3-(trifluoromethyl)phenyl)propan-2-yl)-1,4-dioxa-8-azaspiro{4.5}decane (1.23g, 69%) as a pale-yellow oil.

c) A solution of 8-(2-(3-(trifluoromethyl)phenyl)propan-2-yl)-1,4-dioxa-8-azaspiro{4.5}decane (258 mg, 0.550 mmol) and p-toluenesulfonic acid monohydrate (210 mg, 1.10 mmol) in acetone-H$_2$O (2:1, 9 ml) was refluxed for 5 hours. Hydrochloric acid (3 ml) was added to the reaction mixture, and the whole was refluxed for 4 hours. After the reaction was quenched with aqueous 2 N NaOH solution (pH=10), the aqueous phase was extracted with ethyl acetate (50 ml and 30 ml) and the combined organic phase was washed with brine, dried over MgSO$_4$, filtered and concentrated in vacuo. The residue was purified by column chromatography (ethyl acetate/n-hexane:10/90 to 30/70) to give 1-(2-(3-(trifluoromethyl)phenyl)propan-2-yl)piperidin-4-one (163 mg, 95%) as a pale-yellow oil.

d) 1-(3-Dimethylaminopropyl)-3-ethylcarbodiimide hydrochloride (1.72 g, 8.99 mmol) and cyclopropylmethylamine (0.975 ml, 11.2 mmol) were added to a solution of diethylphosphonoacetic acid (1.23 ml, 7.49 mmol) and 1-hydroxybenzotriazole monohydrate (1.26 g, 8.24 mmol) in CH$_2$Cl$_2$ (20 ml), and the whole was stirred for 12 hours. After the reaction was quenched with brine (30 ml), the aqueous phase was extracted with ethyl acetate (50 ml×3) and the combined organic phase was dried over MgSO$_4$, filtered and concentrated in vacuo to give diethyl 2-(cyclopropylmethylamino)-2-oxoethylphosphonate (1.90 g, 100%) as a pale-yellow oil.

e) Sodium hydride (60%, 63 mg, 1.6 mmol) was added to a solution of 2-(cyclopropylmethylamino)-2-oxoethylphosphonate (160 mg, 0.631 mmol) in THF (3 ml), and the whole was stirred for 10 minutes. A solution of 1-(2-(3-(trifluoromethyl)phenyl)propan-2-yl)piperidin-4-one (150 mg, 0.526 mmol) in THF (2 ml) was added over 5 minutes, and the whole was stirred for 30 minutes. After the reaction mixture was quenched with saturated NaHCO$_3$ solution (10 ml), the aqueous phase was extracted with diethyl ether (20 ml×2). The combined organic phase was washed with brine, dried over MgSO$_4$, filtered and concentrated in vacuo. The residue was purified by column chromatography (ethyl acetate/hexane:40/60 to 60/40) to give N-(cyclopropylmethyl)-2-(1-(2-(3-(trifluoromethyl)phenyl)propan-2-yl)piperidin-4-ylidene)acetamide (171 mg, 85%) as a pale-yellow amorphous compound: LCMS: 381 {M+1}$^+$. $^1$H NMR (DMSO-d$_6$) δ: 0.13 (m, 2H), 0.39 (m, 2H), 0.88 (m, 1H), 1.32 (s, 6H), 2.17 (m, 2H), 2.41-2.44 (m, 4H), 2.89-2.95 (m, 4H), 5.60 (s, 1H), 7.57 (m, 2H), 7.84-7.89 (m, 3H).

Example 32

N-(cyclopropylmethyl)-2-methoxy-2-(1-(4-(trifluoromethoxy)phenylsulfonyl)piperidin-4-ylidene)acetamide

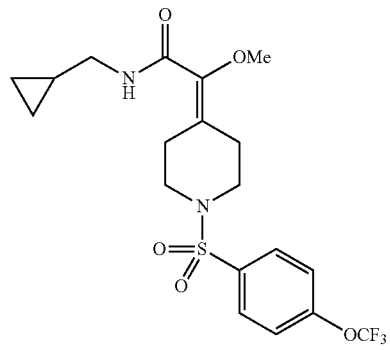 [SMILES: COC(C(=O)NCC1CC1)=C1CCN(S(=O)(=O)c2ccc(OC(F)(F)F)cc2)CC1]

a) A solution of ethyl 2-oxoacetate (11.5 g, 52.9 mmol), diethyl phosphonate (7.75 g, 56.1 mmol) and p-toluenesulfonic acid monohydrate (101 mg, 0.529 mmol) in toluene (100 ml) was heated under reflux with azeotropic removal of water (Dean-Stark) for 12 hours. The reaction mixture was concentrated in vacuo and the residue was purified by column chromatography (CHCl$_3$/methanol: 97/3) to give ethyl 2-(diethoxyphosphoryl)-2-hydroxyacetate (8.09 g, 64%) as a colorless oil.

b) Ag$_2$O (10.2 g, 43.8 mmol) and iodomethane (17.1 ml, 274 mmol) was added to a solution of ethyl 2-(diethoxyphosphoryl)-2-hydroxyacetate (6.58 g, 27.4 mmol) in CHCl$_3$ (20 ml), and the whole was stirred for 6 hours. The reaction mixture was then filtered and the filtrate was concentrated in vacuo. The residue was purified by column chromatography (ethyl acetate/hexane:80/20) to give ethyl 2-(diethoxyphosphoryl)-2-methoxyacetate (2.04 g, 29%) as a colorless oil.

c) A solution of 1-(4-(trifluoromethoxy)phenylsulfonyl)piperidin-4-one (700 mg, 2.17 mmol), ethyl 2-(diethoxyphosphoryl)-2-methoxyacetate (661 mg, 2.60 mmol) and 1,3-dimethyl-3,4,5,6-tetrahydro-2(1H)-pyrimidinone (0.759 ml, 6.28 mmol) in THF (10 ml) was added at 0° C. to a suspension of sodium hydride (60%, 0.113g, 2.81 mmol) in THF (10 ml), and the whole was stirred at 0° C. for 1 hour. After the reaction was quenched with aqueous 10% citric acid solution (10 ml), the aqueous phase was extracted with ethyl acetate (100 ml×2). The combined organic phase was washed with H$_2$O and brine, dried over MgSO$_4$, filtered and concentrated in vacuo. The residue was purified by column chromatography (ethyl acetate/hexane:33/67) to give ethyl 2-methoxy-2-(1-(4-(trifluoromethoxy)phenylsulfonyl)piperidin-4-ylidene)acetate (710 mg, 77%) as a white solid.

d) A mixture of ethyl 2-methoxy-2-(1-(4-(trifluoromethoxy)phenylsulfonyl)piperidin-4-ylidene)acetate (600 mg, 1.42 mmol) and aqueous 2 N NaOH solution (3.54 ml, 7.08 mmol) in ethanol (10 ml) was stirred for 3.5 hours. The reaction was quenched with aqueous 2 N HCl solution (18 ml) and diluted with H$_2$O (20 ml). The resulting solid was collected and washed with H$_2$O to give 2-methoxy-2-(1-(4-(trifluoromethoxy)phenylsulfonyl)piperidin-4-ylidene)acetic acid (509 mg, 91%) as a white solid.

e) 1-Hydroxybenzotriazole monohydrate (34.1 mg, 0.223 mmol), N,N-dimethyl-4-aminopyridine (2.5 mg, 0.020 mmol), cyclopropylmethylamine (0.021 ml, 0.24 mmol) and 1-(3-dimethylaminopropyl)-3-ethylcarbodiimide hydrochloride (42.7 mg, 0.223 mmol) were added to a solution of 2-methoxy-2-(1-(4-(trifluoromethoxy)phenylsulfonyl)piperidin-4-ylidene)acetic acid (80.0 mg, 0.202 mmol) in DMF (1 ml), and the whole was stirred for 4.5 hours. After the reaction was quenched with saturated NaHCO$_3$ solution (5 ml) and H$_2$O (20 ml), the aqueous phase was extracted with ethyl acetate (20 ml×3) and the combined organic phase was washed with H$_2$O (10 ml×2) and brine (10 ml), dried over Na$_2$SO$_4$, filtered and concentrated in vacuo. The residue was purified by column chromatography (ethyl acetate/n-hexane) to give N-(cyclopropylmethyl)-2-methoxy-2-(1-(4-(trifluoromethoxy)phenylsulfonyl)piperidin-4-ylidene)acetamide (87.4 mg, 96%) as a pale-yellow solid: LCMS: 449 {M+1}$^+$. $^1$H NMR (DMSO-d$_6$) δ: 0.15 (m, 2H), 0.37 (m, 2H), 0.93 (m, 1H), 2.38 (m, 2H), 2.66 (m, 2H), 2.95-3.01 (m, 6H), 3.39 (s, 3H), 7.62 (m, 2H), 7.89 (m, 2H), 8.13 (t, 1H).

Example 33

N-cyclopropyl-2-methoxy-2-(1-(4-(trifluoromethoxy)phenylsulfonyl)piperidin-4-ylidene)Acetamide was Prepared in a Manner Similar to that Described in Example 32:

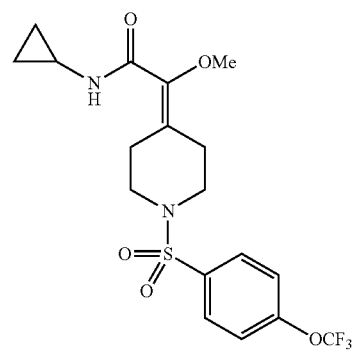 [SMILES: COC(C(=O)NC1CC1)=C1CCN(S(=O)(=O)c2ccc(OC(F)(F)F)cc2)CC1]

white solid: LCMS: 435 {M+1}$^+$. $^1$H NMR (DMSO-d$_6$) δ: 0.47 (m, 2H), 0.60 (m, 2H), 2.36 (m, 2H), 2.59 (m, 2H), 2.68 (m, 1H), 2.71 (m, 4H), 3.33 (s, 3H), 7.62 (m, 2H), 7.89 (m, 2H), 8.09 (d, 1H).

Example 34

N-(2-hydroxyethyl)-2-methoxy-2-(1-(4-(trifluoromethoxy)phenylsulfonyl)piperidin-4-ylidene)Acetamide was Prepared in a Manner Similar to that Described in Example 32:

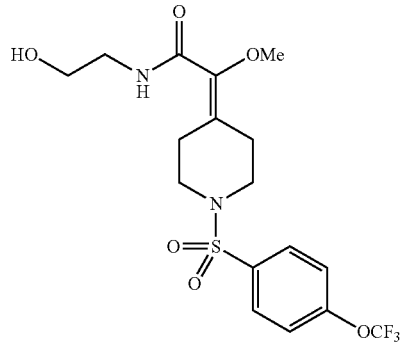 [SMILES: COC(C(=O)NCCO)=C1CCN(S(=O)(=O)c2ccc(OC(F)(F)F)cc2)CC1]

white solid: LCMS: 439 {M+1}+. 1H NMR (DMSO-d6) δ: 2.38 (m, 2H), 2.67 (m, 2H), 2.98 (m, 4H), 3.16 (m, 2H), 3.37 (s, 3H), 3.39-3.43 (m, 2H), 4.63 (t, 1H), 7.62 (d, 2H), 7.89 (d, 2H), 7.94 (t, 1H).

Example 35

(E)-N-cyclopropyl-3-(1-(4-(trifluoromethoxy)phenylsulfonyl)piperidin-4-yl)acrylamide

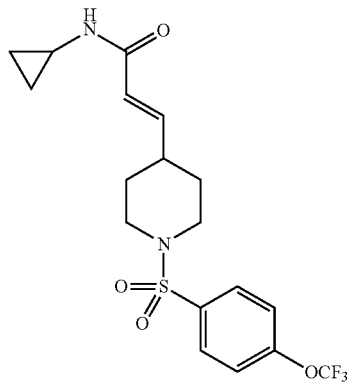 [SMILES: O=C(/C=C/C1CCN(S(=O)(=O)c2ccc(OC(F)(F)F)cc2)CC1)NC1CC1]

a) 2-Iodoxybenzoic acid (3.90 g, 13.9 mmol) was added to a solution of tert-butyl 4-(hydroxymethyl)piperidine-1-carboxylate (1.00 g, 4.64 mmol) in ethyl acetate (20 ml), and the whole was refluxed for 4 hours. The reaction mixture was then filtered and the filtrate was concentrated in vacuo. The residue was purified by column chromatography (ethyl acetate/hexane:0/100 to 40/60) to give tert-butyl 4-formylpiperidine-1-carboxylate (540 mg, 2.53 mmol) as a colorless oil.

b) Ethyl 2-(diethoxyphosphoryl)acetate (0.542 ml, 2.73 mmol) was added at 0° C. to a suspension of sodium hydride (60%, 109 mg, 2.73 mmol) in THF (10 ml), and the whole was stirred at 0° C. for 10 minutes. A solution of tert-butyl 4-formylpiperidine-1-carboxylate (530 mg, 2.49 mmol) in THF (10 ml) was added and the whole was stirred at 0° C. for 30 minutes. The reaction mixture was quenched with saturated H2O, and the aqueous phase was extracted with ethyl acetate (50 ml×2). The combined organic phase was washed with brine, dried over MgSO4, filtered and concentrated in vacuo. The residue was purified by column chromatography (ethyl acetate/hexane: 0/100 to 20/80) to give (E)-tert-butyl 4-(3-ethoxy-3-oxoprop-1-enyl)piperidine-1-carboxylate (475 mg, 68%) as a colorless oil.

c) 4 N HCl solution in 1,4-dioxane (0.829 ml, 3.32 mmol) was added to a solution of (E)-tert-butyl 4-(3-ethoxy-3-oxoprop-1-enyl)piperidine-1-carboxylate (470 mg, 1.66 mmol) in 1,4-dioxane (2 ml), and the whole was stirred at 60° C. for 2 hours. The reaction mixture was concentrated in vacuo and the residual solid was triturated with diethyl ether to give (E)-ethyl 3-(piperidin-4-yl)acrylate hydrochloride (350 mg, 96%) as a white solid.

d) 4-(Trifluoromethoxy)benzenesulfonyl chloride (0.289 ml, 1.70 mmol) was added at 0° C. to a solution of (E)-ethyl 3-(piperidin-4-yl)acrylate hydrochloride (340 mg, 1.55 mmol) in pyridine (5 ml), and the whole was stirred for 2 hours. After the reaction mixture was concentrated in vacuo, the residue was diluted with ethyl acetate, washed with 1 N HCl solution, saturated NaHCO3 solution and brine, dried over MgSO4, filtered and concentrated in vacuo to give (E)-ethyl 3-(1-(4-(trifluoromethoxy)phenylsulfonyl)piperidin-4-yl)acrylate (626 mg, 99%) as a paleyellow solid.

e) A mixture of (E)-ethyl 3-(1-(4-(trifluoromethoxy)phenylsulfonyl)piperidin-4-yl)acrylate (617 mg, 1.51 mmol) and aqueous 2 N NaOH solution (0.833 ml, 1.67 mmol) in ethanol (6 ml) was stirred for 7 hours. The reaction was quenched with aqueous 2 N HCl solution (0.900 ml), and the resulting solid was collected and washed with H2O to give (E)-3-(1-(4-(trifluoromethoxy)phenylsulfonyl)piperidin-4-yl)acrylic acid (546 mg, 95%) as a white solid.

f) 1-Hydroxybenzotriazole monohydrate (66.6 mg, 0.435 mmol), cyclopropanamine (0.041 ml, 0.59 mmol) and 1-(3-dimethylaminopropyl)-3-ethylcarbodiimide hydrochloride (83.0 mg, 0.435 mmol) were added to a solution of (E)-3-(1-(4-(trifluoromethoxy)phenylsulfonyl)piperidin-4-yl)acrylic acid (150 mg, 0.395 mmol) in CH2Cl2 (3 ml), and the whole was stirred for 1 hour. After the reaction was quenched with saturated NaHCO3 solution, the aqueous phase was extracted with ethyl acetate (30 ml) and the combined organic phase was washed with 0.1 N HCl solution, saturated NaHCO3 solution and brine, dried over MgSO4, filtered and concentrated in vacuo. The residual solid was recrystallized from ethyl acetate to give (E)-N-cyclopropyl-3-(1-(4-(trifluoromethoxy)phenylsulfonyl)piperidin-4-yl)acrylamide (100 mg, 60%) as a white solid: LCMS: 419 {M+1}+. 1H NMR (DMSO-d6) δ: 0.40 (m, 2H), 0.59 (m, 2H), 1.33 (m, 2H), 1.74 (m, 2H), 2.11 (m, 1H), 2.32 (m, 2H), 2.65 (m, 1H), 3.66 (m, 2H), 5.74 (d, 1H), 6.51 (dd, 1H), 7.64 (m, 2H), 7.89 (m, 2H), 7.98 (d, 1H).

Example 36

(Z)—N-cyclopropyl-3-methoxy-3-(1-(4-(trifluoromethoxy)phenylsulfonyl)piperidin-4-yl)acrylamide

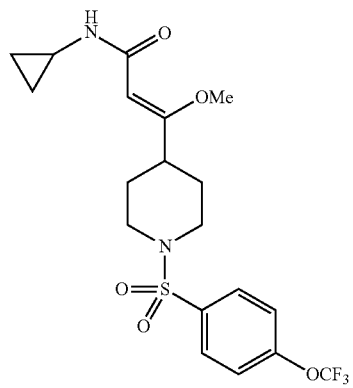 [SMILES: CO/C(=C\C(=O)NC1CC1)C1CCN(S(=O)(=O)c2ccc(OC(F)(F)F)cc2)CC1]

a) A solution of 4-(trifluoromethoxy)benzenesulfonyl chloride (9.05 g, 34.7 mmol) in 1,4-dioxane (40 ml) was added dropwise at 0° C. to a solution of piperidin-4-ylmethanol (4.00 g, 34.7 mmol) and K2CO3 (7.20 g, 52.1 mmol) in H2O (40 ml), and the whole was stirred at room temperature for 1 hour. After the reaction mixture was diluted with H2O, the whole was extracted with ethyl acetate (200×2 ml). The combined organic phase was washed with 1 N HCl solution, H2O, saturated NaHCO3 solution, H2O and brine, dried over MgSO4, filtered and concentrated in vacuo. The residual solid was triturated with diethyl ether and n-hexane to give (1-(4-(trifluoromethoxy)phenylsulfonyl)piperidin-4-yl)methanol (11.0 g, 93%) as a white solid.

b) 2-Iodoxybenzoic acid (9.90 g, 35.4 mmol) was added to a solution of (1-(4-(trifluoromethoxy)phenylsulfonyl)piperidin-4-yl)methanol (6.00 g, 17.7 mmol) in ethyl acetate (100 ml), and the whole was refluxed for 2 hours. After the reaction mixture was filtered, the filtrate was concentrated in vacuo to give 1-(4-(trifluoromethoxy)phenylsulfonyl)piperidine-4-carbaldehyde (5.98 g, 100%) as a white solid.

c) Ethyl 2-iodoacetate (0.899 ml, 7.60 mmol) was added to a suspension of zinc (49 mg, 7.60 mmol) in THF (12 ml), and the whole was refluxed for 1 hour. 1-(4-(Trifluoromethoxy)phenylsulfonyl)piperidine-4-carbaldehyde (1.28 g, 3.80 mmol) was added to the reaction mixture, and the whole was stirred for 2.5 hours. The reaction was quenched with saturated NH$_4$Cl solution (5 ml), and the aqueous phase was extracted with ethyl acetate (30 ml×3). The combined organic phase was dried over Na$_2$SO$_4$, filtered and concentrated in vacuo. The residue was purified by column chromatography (ethyl acetate/hexane:35/65) to give ethyl 3-hydroxy-3-(1-(4-(trifluoromethoxy)phenylsulfonyl)piperidin-4-yl)propanoate (1.03g, 64%) as a pale-yellow solid.

d) 2-Iodoxybenzoic acid (724 mg, 2.59 mmol) was added to a solution of 3-hydroxy-3-(1-(4-(trifluoromethoxy)phenylsulfonyl)piperidin-4-yl)propanoate (500 mg, 1.18 mmol) in ethyl acetate (5 ml), and the whole was refluxed for 6.5 hours. After the reaction mixture was filtered, the filtrate was concentrated in vacuo. The residue was purified by column chromatography (ethyl acetate/hexane:30/70) to give ethyl 3-oxo-3-(1-(4-(trifluoromethoxy)phenylsulfonyl)piperidin-4-yl)propanoate (397 mg, 80%) as a white solid.

e) A solution of 3-oxo-3-(1-(4-(trifluoromethoxy)phenylsulfonyl)piperidin-4-yl)propanoate (150 mg, 0.354 mmol) and sulfuric acid (10 drops) in trimethyl orthoformate (3.00 ml, 27.1 mmol), and the whole was stirred for 4 days. After the reaction was quenched with saturated NaHCO$_3$ solution (10 ml), the aqueous phase was extracted with ethyl acetate (20 ml×3) and the combined organic phase was washed with brine (10 ml), dried over Na$_2$SO$_4$, filtered and concentrated in vacuo. The residue was purified by column chromatography (ethyl acetate/hexane:22/78) to give (Z)-ethyl 3-methoxy-3-(1-(4-(trifluoromethoxy)phenylsulfonyl)piperidin-4-yl)acrylate (105 mg, 68%).

f) A mixture of (Z)-ethyl 3-methoxy-3-(1-(4-(trifluoromethoxy)phenylsulfonyl)piperidin-4-yl)acrylate (60.0 mg, 0.137 mmol) and aqueous 2 N NaOH solution (0.274 ml, 0.548 mmol) in ethanol (2 ml) was refluxed for 6.5 hours. After the reaction was quenched with aqueous 2 N HCl solution (0.280 ml), the aqueous phase was extracted with ethyl acetate (20 ml×3) and the combined organic phase was washed with brine (10 ml), dried over Na$_2$SO$_4$, filtered and concentrated in vacuo to give (Z)-3-methoxy-3-(1-(4-(trifluoromethoxy)phenylsulfonyl)piperidin-4-yl) acrylic acid (56.8 mg, 100%).

g) 1-Hydroxybenzotriazole monohydrate (20.6 mg, 0.134 mmol), N,N-dimethyl-4-aminopyridine (1.5 mg, 0.012 mmol), cyclopropanamine (0.017 ml, 0.24 mmol) and 1-(3-dimethylaminopropyl)-3-ethylcarbodiimide hydrochloride (25.8 mg, 0.134 mmol) were added to a solution of (Z)-3-methoxy-3-(1-(4-(trifluoromethoxy)phenylsulfonyl)piperidin-4-yl)acrylic acid (50.0 mg, 0.122 mmol) in DMF (2 ml), and the whole was stirred for 19 hours. After the reaction was quenched with saturated NaHCO$_3$ solution (5 ml) and H$_2$O (20 ml), the aqueous phase was extracted with ethyl acetate (20 ml×3) and the combined organic phase was washed with H$_2$O (10 ml×2) and brine (10 ml), dried over Na$_2$SO$_4$, filtered and concentrated in vacuo. The residue was purified by column chromatography (ethyl acetate/hexane: 50/50) to give (Z)—N-cyclopropyl-3-methoxy-3-(1-(4-(trifluoromethoxy)phenylsulfonyl)piperidin-4-yl)acrylamide (28.3 mg, 52%) as a white solid: LCMS: 449 {M+1}$^+$. $^1$H NMR (CDCl$_3$) δ: 0.46 (m, 2H), 0.74 (m, 2H), 1.70-1.85 (m, 4H), 2.32 (m, 2H), 2.63 (m, 1H), 3.54 (s, 3H), 3.83 (m, 3H), 4.70 (s, 1H), 5.40 (s, 1H), 7.35 (d, 2H), 7.79 (d, 2H).

Example 37

(Z)—N-cyclopropyl-2-methoxy-3-(1-(4-(trifluoromethoxy)phenylsulfonyl)piperidin-4-yl)acrylamide

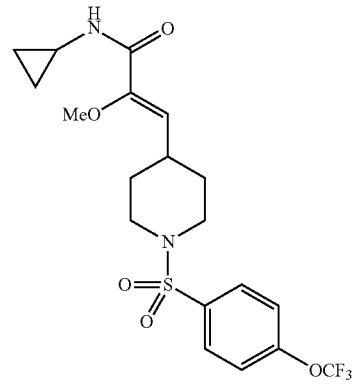 [SMILES: CO/C(=C\C1CCN(S(=O)(=O)c2ccc(OC(F)(F)F)cc2)CC1)C(=O)NC1CC1]

a) A solution of 1-(4-(trifluoromethoxy)phenylsulfonyl)piperidine-4-carbaldehyde (410 mg, 1.22 mmol), ethyl 2-(diethoxyphosphoryl)-2-methoxyacetate (340 mg, 1.34 mmol) and 1,3-dimethyl-3,4,5,6-tetrahydro-2(1H)-pyrimidinone (0.426 ml, 3.53 mmol) in THF (10 ml) was added at 0° C. to a suspension of sodium hydride (60%, 0.107 g, 2.67 mmol) in THF (10 ml), and the whole was stirred at 0° C. for 1 hour. After the reaction was quenched with aqueous 10% citric acid solution (10 ml), the aqueous phase was extracted with ethyl acetate (50 ml×2). The combined organic phase was washed with H$_2$O and brine, dried over MgSO$_4$, filtered and concentrated in vacuo. The residue was purified by column chromatography (ethyl acetate/hexane: 33/67) to give (Z)-ethyl 2-methoxy-3-(1-(4-(trifluoromethoxy)phenylsulfonyl)piperidin-4-yl)acrylate (110 mg, 21%) as a white solid and (E)-ethyl 2-methoxy-3-(1-(4-(trifluoromethoxy)phenylsulfonyl)piperidin-4-yl) acrylate (280 mg, 53%) as a colorless oil.

b) A mixture of (Z)-ethyl 2-methoxy-3-(1-(4-(trifluoromethoxy)phenylsulfonyl)piperidin-4-yl)acrylate (100 mg, 0.229 mmol) and aqueous 2 N NaOH solution (0.229 ml, 0.458 mmol) in ethanol (4 ml) was stirred at 45° C. for 4 hours. After the reaction was quenched with aqueous 2 N HCl solution (0.230 ml) and H$_2$O (10 ml), the aqueous phase was extracted with ethyl acetate (20 ml×3) and the combined organic phase was washed with brine (10 ml), dried over Na$_2$SO$_4$, filtered and concentrated in vacuo to give (Z)-2-methoxy-3-(1-(4-(trifluoromethoxy)phenylsulfonyl)piperidin-4-yl)acrylic acid (94.0 mg, 100%).

c) 1-Hydroxybenzotriazole monohydrate (37.0 mg, 0.242 mmol), N,N-dimethyl-4-aminopyridine (2.7 mg, 0.022 mmol), cyclopropanamine (0.030 ml, 0.44 mmol) and 1-(3-dimethylaminopropyl)-3-ethylcarbodiimide hydrochloride (46.4 mg, 0.242 mmol) were added to a solution of (Z)-2-methoxy-3-(1-(4-(trifluoromethoxy)phenylsulfonyl)piperidin-4-yl)acrylic acid (90.0 mg, 0.220 mmol) in DMF (2 ml), and the whole was stirred for 15 hours. After the reaction was quenched with saturated NaHCO$_3$ solution (5 ml) and H$_2$O (20 ml), the resulting solid was collected, washed with H$_2$O and recrystallized from ethyl acetate/n-hexane to give (Z)—N-cyclopropyl-2-methoxy-3-(1-(4-(trifluoromethoxy)phenylsulfonyl)piperidin-4-yl)acrylamide (70.5 mg, 72%) as a white solid: LCMS: 449 {M+1}$^+$. $^1$H NMR (DMSO-d$_6$)□ δ: 0.49-0.63 (m, 4H), 1.35-1.44 (m, 2H), 1.63 (m, 2H), 2.34-2.46 (m, 3H), 2.68 (m, 1H), 3.44 (s, 3H), 3.62 (m, 2H), 5.65 (d, 1H), 7.64 (d, 2H), 7.89 (d, 2H), 7.95 (d, 1H).

Example 38

(E)-N-cyclopropyl-2-methoxy-3-(1-(4-(trifluoromethoxy)phenylsulfonyl)piperidin-4-yl)acrylamide was prepared in a manner similar to that described in EXAMPLE 37:

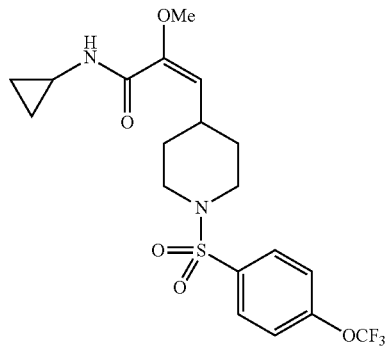 [SMILES: CO/C(=C/C1CCN(S(=O)(=O)c2ccc(OC(F)(F)F)cc2)CC1)C(=O)NC1CC1]

white solid: LCMS: 449 {M+1}$^+$. $^1$H NMR (DMSO-d$_6$)□ δ: 0.44-0.59 (m, 4H), 1.28-1.37 (m, 2H), 1.69-1.72 (m, 2H), 2.24 (m, 2H), 2.64 (m, 1H), 2.94 (m, 1H), 3.44 (s, 3H), 3.64 (m, 2H), 4.71 (d, 1H), 7.64 (d, 2H), 7.89 (m, 3H).

Example 39

(Z)—N-(cyclopropylmethyl)-2-(1-(4-(trifluoromethoxy)phenylsulfonyl)piperidin-3-ylidene)acetamide was prepared in a manner similar to that described below in EXAMPLE 40:

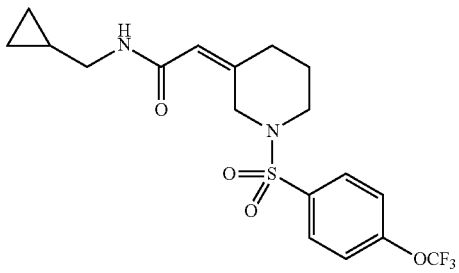 [SMILES: O=C(/C=C1/CCCN(S(=O)(=O)c2ccc(OC(F)(F)F)cc2)C1)NCC1CC1]

white solid: LCMS: 419 {M+1}$^+$. $^1$H NMR (DMSO-d$_6$)□ β: 0.17 (m, 2H), 0.42 (m, 2H), 0.92 (m, 1H), 1.58 (m, 2H), 2.13 (m, 2H), 2.99 (m, 2H), 3.19 (m, 2H), 4.42 (s, 2H), 5.69 (s, 1H), 7.61 (d, 2H), 7.88 (d, 2H), 8.08 (t, 1H).

Example 40

(E)-N-(cyclopropylmethyl)-2-(1-(4-(trifluoromethoxy)phenylsulfonyl)piperidin-3-ylidene)acetamide

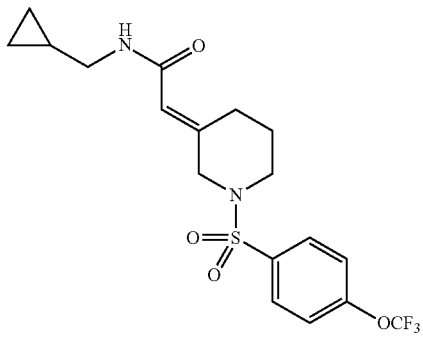 [SMILES: O=C(/C=C1\CCCN(S(=O)(=O)c2ccc(OC(F)(F)F)cc2)C1)NCC1CC1]

a) A solution of tert-butyl 2-(dimethoxyphosphoryl)acetate (1.23g, 5.50 mmol) in THF (10 ml) was added dropwise at 0° C. to a suspension of sodium hydride (60%, 220 mg, 5.50 mmol) in THF (10 ml), and the whole was stirred at 0° C. for 10 minutes. A solution of tert-butyl 3-oxopiperidine-1-carboxylate (996 mg, 5.00 mmol) in THF (20 ml) was added dropwise to the reaction mixture, and the whole was stirred at room temperature for 1 hour. After the reaction was quenched with H$_2$O, the aqueous phase was extracted with ethyl acetate (100 ml×2). The combined organic phase was washed with brine, dried over MgSO$_4$, filtered and concentrated in vacuo. The residue was purified by column chromatography (ethyl acetate/hexane:0/100 to 10/90) to give (E)-tert-butyl 3-(2-tert-butoxy-2-oxoethylidene)piperidine-1-carboxylate (1.04 g, 70%) as colorless oil and (Z)-tert-butyl 3-(2-tert-butoxy-2-oxoethylidene)piperidine-1-carboxylate (400 mg, 27%) as a colorless oil.

b) Trifluoroacetic acid (4.00 ml, 52.0 mmol) was added at 0° C. to a solution of (E)-tert-butyl 3-(2-tert-butoxy-2-oxoethylidene)piperidine-1-carboxylate (1.04 g, 3.50 mmol) in CH$_2$Cl$_2$ (2 ml), and the whole was stirred at room temperature for 2 hours. The reaction mixture was concentrated in vacuo to give a crude product of (E)-2-(piperidin-3-ylidene)acetic acid trifluoroacetic acid salt.

c) Triethylamine (0.914 ml, 6.60 mmol) was added dropwise at 0° C. to a solution of (E)-2-(piperidin-3-ylidene)acetic acid trifluoroacetic acid salt (383 mg, 1.50 mmol) and 4-(trifluoromethoxy)benzenesulfonyl chloride (0.280 ml, 1.65 mmol) in methanol (15 ml), and the whole was stirred at room temperature for 2 hours. After the reaction was quenched with 2 N HCl solution, the aqueous phase was extracted with ethyl acetate (20 ml×2). The combined organic phase was washed with brine, dried over MgSO$_4$, filtered and concentrated in vacuo to give (E)-2-(1-(4-(trifluoromethoxy)phenylsulfonyl)piperidin-3-ylidene)acetic acid (440 mg, 80%) as a white solid.

d) Oxalyl chloride (0.0370 ml, 0.422 mmol) and DMF (0.030 ml, 0.383 mmol) were added successively at 0° C. to a solution of (E)-2-(1-(4-(trifluoromethoxy)phenylsulfonyl)piperidin-3-ylidene)acetic acid (140 mg, 0.383 mmol) in CH$_2$Cl$_2$ (2 ml), and the whole was stirred at room temperature for 1 hour. After the reaction mixture was concentrated in vacuo, the residue was diluted with CH$_2$Cl$_2$ (3 ml). Cyclopropylmethylamine (0.040 ml, 0.460 mmol) and triethylamine (0.064 ml, 0.460 mmol) were added successively at 0° C. to this solution, and the whole was stirred at room temperature for 1 hour. After the reaction was quenched with saturated NaHCO₃ solution, the aqueous phase was extracted with ethyl acetate (20 ml×2). The combined organic phase was washed with brine, dried over MgSO₄, filtered and concentrated in vacuo. The residue was purified by column chromatography (ethyl acetate/hexane:0/100 to 40/60) to give (Z)—N-(cyclopropylmethyl)-2-(1-(4-(trifluoromethoxy)phenylsulfonyl)piperidin-3-ylidene)acetamide (66.0 mg, 41%) as a white solid and (E)-N-(cyclopropylmethyl)-2-(1-(4-(trifluoromethoxy)phenylsulfonyl)piperidin-3-ylidene)acetamide (86.0 mg, 54%) as a white solid.

(Z)—N-(cyclopropylmethyl)-2-(1-(4-(trifluoromethoxy)phenylsulfonyl)piperidin-3-ylidene)acetamide: LCMS: 419 {M+1}⁺. ¹H NMR (DMSO-d₆)□ δ: 0.17 (m, 2H), 0.42 (m, 2H), 0.92 (m, 1H), 1.58 (m, 2H), 2.13 (m, 2H), 2.99 (m, 2H), 3.19 (m, 2H), 4.42 (s, 2H), 5.69 (s, 1H), 7.61 (d, 2H), 7.88 (d, 2H), 8.08 (t, 1H).

(E)-N-(cyclopropylmethyl)-2-(1-(4-(trifluoromethoxy)phenylsulfonyl)piperidin-3-ylidene)acetamide: LCMS: 419 {M+1}⁺. ¹H NMR (DMSO-d₆)□ δ: 0.15 (m, 2H), 0.41 (m, 2H), 0.89 (m, 1H), 1.55 (m, 2H), 2.78 (m, 2H), 2.95 (m, 2H), 3.11 (m, 2H), 3.52 (s, 2H), 5.81 (s, 1H), 7.63 (d, 2H), 7.93 (d, 2H), 8.05 (t, 1H).

Example 41

(E)-N-cyclopropyl-2-(1-(4-(trifluoromethoxy)phenylsulfonyl)piperidin-3-ylidene)acetamide was prepared in a manner similar to that described in EXAMPLE 40:

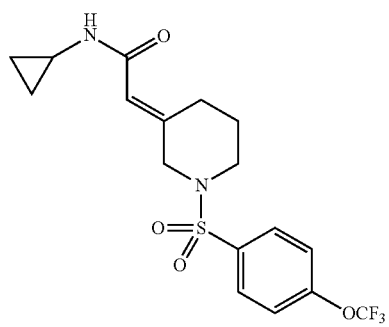 [SMILES: O=C(/C=C1\CCCN(S(=O)(=O)c2ccc(OC(F)(F)F)cc2)C1)NC1CC1]

white solid: LCMS: 405 {M+1}⁺. ¹H NMR (DMSO-d₆)□ δ: 0.39 (m, 2H), 0.63 (m, 2H), 1.57 (m, 2H), 2.65 (m, 1H), 2.78 (m, 2H), 3.11 (m, 2H), 3.50 (s, 2H), 5.70 (s, 1H), 7.62 (d, 2H), 7.92 (d, 2H), 8.03 (d, 1H).

Example 42

(Z)—N-(4-fluorophenyl)-2-(1-(4-(trifluoromethoxy)phenylsulfonyl)piperidin-3-ylidene)acetamide was prepared in a manner similar to that described in EXAMPLE 40:

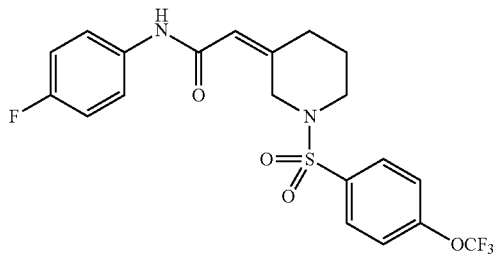 [SMILES: O=C(/C=C1/CCCN(S(=O)(=O)c2ccc(OC(F)(F)F)cc2)C1)Nc1ccc(F)cc1]

colorless amorphous: LCMS: 459 {M+1}⁺. ¹H NMR (DMSO-d₆)□ δ: 1.66 (m, 2H), 2.23 (m, 2H), 3.21 (m, 2H), 4.44 (s, 2H), 5.88 (s, 1H), 7.17 (m, 2H), 7.58 (d, 2H), 7.66 (m, 2H), 7.91 (d, 2H), 10.12 (s, 1H).

Example 43

(Z)—N-cyclopropyl-2-(1-(4-(trifluoromethoxy)phenylsulfonyl)piperidin-3-ylidene)acetamide was prepared in a manner similar to that described in EXAMPLE 40:

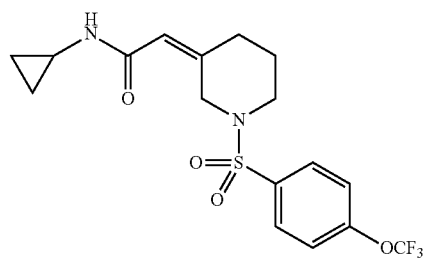 [SMILES: O=C(/C=C1/CCCN(S(=O)(=O)c2ccc(OC(F)(F)F)cc2)C1)NC1CC1]

white solid: LCMS: 405 {M+1}⁺. ¹H NMR (DMSO-d₆)□ δ: 0.40 (m, 2H), 0.65 (m, 2H), 1.59 (m, 2H), 2.12 (m, 2H), 2.69 (m, 1H), 3.17 (m, 2H), 4.40 (s, 2H), 5.58 (s, 1H), 7.62 (d, 2H), 7.88 (d, 2H), 8.06 (d, 1H).

Example 44

(Z)—N-cyclopropyl-2-methoxy-3-(4-(4-(trifluoromethoxy)phenylsulfonyl)morpholin-2-yl)acrylamide

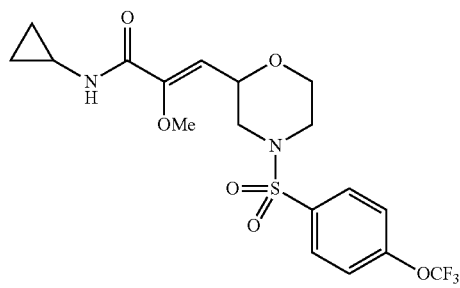 [SMILES: CO/C(=C\C1CN(S(=O)(=O)c2ccc(OC(F)(F)F)cc2)CCO1)C(=O)NC1CC1]

a) A solution of 4-(trifluoromethoxy)benzenesulfonyl chloride (3.69 g, 14.2 mmol) in 1,4-dioxane (20 ml) was added dropwise at 0° C. to a solution of morpholin-2-ylmethanol (1.66 g, 14.2 mmol) and $K_2CO_3$ (3.50 g, 25.3 mmol) in $H_2O$ (20 ml), and the whole was stirred at room temperature for 24 hours. After the reaction mixture was diluted with $H_2O$, the aqueous phase was extracted with ethyl acetate (200 ml×2). The combined organic phase was washed with $H_2O$ and brine, dried over $MgSO_4$, filtered and concentrated in vacuo. The residual solid was recrystallized from ethyl acetate/n-hexane to give (4-(4-(trifluoromethoxy)phenylsulfonyl)morpholin-2-yl)methanol (3.40 g, 70%) as a white solid.

b) A solution of dimethylsulfoxide (0.458 ml, 6.45 mmol) in $CH_2Cl_2$ (5 ml) was added at −78° C. to a solution of oxalyl chloride (0.282 ml, 3.22 mmol) in $CH_2Cl_2$ (5 ml), and the whole was stirred at −78° C. for 5 minutes. A solution of (4-(4-(trifluoromethoxy)phenylsulfonyl)morpholin-2-yl)methanol (1.00 g, 2.93 mmol) in $CH_2Cl_2$ (5 ml) was added at −78° C. to the reaction mixture, and the whole was stirred at −78° C. for 15 minutes. A solution of triethylamine (2.03 ml, 14.7 mmol) in $CH_2Cl_2$ (5 ml) was added at −78° C. to the reaction mixture, and the whole was stirred at room temperature for 1.5 hours. After the reaction was quenched with $H_2O$, the aqueous phase was extracted with $CH_2Cl_2$ (50 ml×2). The combined organic phase was washed with 1 N HCl solution, $H_2O$, saturated $NaHCO_3$ solution, $H_2O$ and brine, dried over $MgSO_4$, filtered and concentrated in vacuo. The residue was purified by column chromatography (ethyl acetate/hexane:25/75) to give 4-(4-(trifluoromethoxy)phenylsulfonyl)morpholine-2-carbaldehyde (750 mg, 75%) as a colorless oil.

c) A solution of 4-(4-(trifluoromethoxy)phenylsulfonyl)morpholine-2-carbaldehyde (750 mg, 2.21 mmol), ethyl 2-(diethoxyphosphoryl)-2-methoxyacetate (618 mg, 2.43 mmol) and 1,3-dimethyl-3,4,5,6-tetrahydro-2(1H)-pyrimidinone (0.775 ml, 6.41 mmol) in THF (10 ml) was added at 0° C. to a suspension of sodium hydride (60%, 106 mg, 2.65 mmol) in THF (10 ml), and the whole was stirred at 0° C. for 1 hour. After the reaction was quenched with aqueous 10% citric acid solution (30 ml), the aqueous phase was extracted with ethyl acetate (100 ml×2). The combined organic phase was washed with $H_2O$ and brine, dried over $MgSO_4$, filtered and concentrated in vacuo. The residue was purified by column chromatography (ethyl acetate/hexane: 25/75) to give (Z)-ethyl 2-methoxy-3-(4-(4-(trifluoromethoxy)phenylsulfonyl)morpholin-2-yl)acrylate (253 mg, 26%) as a colorless oil and (E)-ethyl 2-methoxy-3-(4-(4-(trifluoromethoxy)phenylsulfonyl)morpholin-2-yl)acrylate (181 mg, 19%) as a colorless oil.

d) A mixture of (Z)-ethyl 2-methoxy-3-(4-(4-(trifluoromethoxy)phenylsulfonyl)morpholin-2-yl)acrylate (253 mg, 0.576 mmol) and aqueous 2 N NaOH solution (1.44 ml, 2.88 mmol) in ethanol (5 ml) was stirred at room temperature for 16 hours. After the reaction was quenched with aqueous 2 N HCl solution (2.00 ml), the aqueous phase was extracted with ethyl acetate (50 ml×2) and the combined organic phase was washed with $H_2O$ and brine, dried over $MgSO_4$, filtered and concentrated in vacuo to give (Z)-2-methoxy-3-(4-(4-(trifluoromethoxy)phenylsulfonyl)morpholin-2-yl)acrylic acid (247 mg, 100%) as a white solid.

e) 1-Hydroxybenzotriazole monohydrate (37.3 mg, 0.243 mmol), N,N-dimethyl-4-aminopyridine (2.7 mg, 0.022 mmol), cyclopropanamine (25.3 mg, 0.442 mmol) and 1-(3-dimethylaminopropyl)-3-ethylcarbodiimide hydrochloride (46.6 mg, 0.243 mmol) were added to a solution of (Z)-2-methoxy-3-(4-(4-(trifluoromethoxy)phenylsulfonyl)morpholin-2-yl)acrylic acid (91.0 mg, 0.221 mmol) in DMF (5 ml), and the whole was stirred for 16 hours. After the reaction was quenched with saturated $NaHCO_3$ solution (10 ml), the aqueous phase was extracted with ethyl acetate (100 ml×2) and the combined organic phase was washed with $H_2O$ and brine, dried over $MgSO_4$, filtered and concentrated in vacuo. The residue was purified by column chromatography (ethyl acetate/n-hexane:50/50) and recrystallized from diethyl ether/n-hexane to give (Z)—N-cyclopropyl-2-methoxy-3-(4-(4-(trifluoromethoxy)phenylsulfonyl)morpholin-2-yl)acrylamide (78.0 mg, 78%) as a white solid: LCMS: 451 {M+1}±. $^1H$ NMR (DMSO-$d_6$) δ: 0.51 (m, 2H), 0.62 (m, 2H), 2.23 (m, 1H), 2.39 (m, 1H), 2.71 (m, 1H), 3.38-3.46 (m, 2H), 3.58 (s, 3H), 3.63 (m, 1H), 3.87 (m, 1H), 4.39 (m, 1H), 5.49 (d, 1H), 7.65 (d, 2H), 7.89 (d, 2H), 8.20 (d, 1H).

Example 45

(E)-N-cyclopropyl-2-methoxy-3-(4-(4-(trifluoromethoxy)phenylsulfonyl)morpholin-2-yl)acrylamide was prepared in a manner similar to that described in EXAMPLE 44:

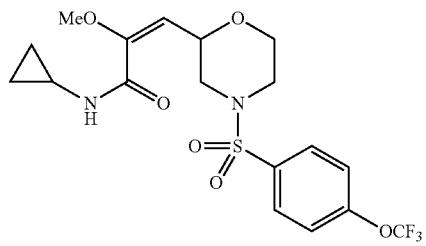 [SMILES: CO/C(=C/C1CN(S(=O)(=O)c2ccc(OC(F)(F)F)cc2)CCO1)C(=O)NC1CC1]

white solid: LCMS: 451 {M+1}$^+$. $^1H$ NMR (DMSO-$d_6$) δ: 0.54 (m, 2H), 0.63 (m, 2H), 2.08 (m, 1H), 2.31 (m, 1H), 2.74 (m, 1H), 3.44-3.55 (m, 5H), 3.65 (m, 1H), 3.86 (m, 1H), 4.73 (d, 1H), 4.80 (m, 1H), 7.64 (d, 2H), 7.90 (d, 2H), 8.14 (d, 1H).

Purity of compounds was verified by LCMS measurement. LCMS methods are as follows;

(Method A) Column: Phenomemex Luna C18 (4.6×50 mm, 5 micron particle size), Temperature: 50° C., Pressure limit: 400 bar, Monitored at OD 254 nm, reference 360 nm, Flow rate: 2 ml/min.

HPLC Gradient (Buffer A=0.1% $HCO_2H/H_2O$, Buffer B=0.1% $HCO_2H/CH_3CN$)

| Time (min.) | % B |
|---|---|
| 0 | 15 |
| 1.9 | 45 |
| 4.3 | 45 |
| 8.3 | 95 |
| 11.3 | 95 |
| 11.4 | 15 |
| 15.4 | 15 |

(Method B) Column: Discovery HS C18 (4.6×150 mm, 3 micron particle size), Temperature: 25° C., Pressure limit: 400 bar, Monitored at OD 260 nm, reference 360 nm, Flow rate: 1 ml/min.

HPLC Gradient (Buffer A=0.1% $TFA/H_2O$, Buffer B=0.1% $TFA/CH_3CN$)

| Time (min.) | % B |
|---|---|
| 0 | 15 |
| 1.9 | 45 |
| 4.3 | 45 |
| 8.3 | 95 |
| 11.3 | 95 |
| 11.4 | 15 |
| 15.4 | 15 |

(Method C) Column: Phenomemex Luna C18 (4.6×50 mm, 5 micron particle size), Temperature: 50° C., Pressure limit: 344.75 bar, Monitored at OD 254 nm, Flow rate: 3 ml/min.

HPLC Gradient (Buffer A=0.1% $HCO_2H/H_2O$, Buffer B=0.1% $HCO_2H/CH_3CN$)

| Time (min.) | % B |
|---|---|
| 0 | 10 |
| 3.0 | 100 |
| 4.0 | 100 |

Example 46

Compounds of the invention have been tested in the calcium mobilization and/or electrophysiological assay for N-type calcium channel blocking activity, which are described in detail above. Representative values are presented in TABLE 2.

TABLE 2

Evaluation of the tested compounds as N-type calcium channel (NTCC) blockers after a calcium mobilization in vitro assay

| EXAMPLE | NTCC (nM) |
|---|---|
| 3 | 598 |
| 9 | 115 |
| 10 | 161 |
| 11 | 560 |
| 12 | 361 |
| 13 | 248 |
| 15 | 718 |
| 19 | 865 |
| 20 | 822 |
| 22 | 829 |
| 31 | 681 |
| 32 | 912 |
| 37 | 555 |
| 38 | 832 |
| 40 | 695 |
| 41 | 990 |
| 44 | 857 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

The invention claimed is:

1. A compound having Formula I:

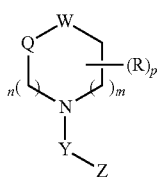

I a pharmaceutically acceptable salt or a solvate thereof, wherein:

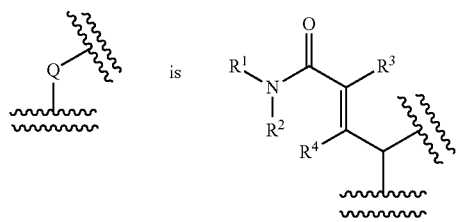 is

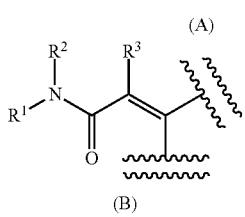

$R^1$ and $R^2$ are each independently hydrogen, cyano, optionally substituted alkyl, optionally substituted alkenyl, optionally substituted alkynyl, optionally substituted alkoxy, optionally substituted alkenyloxy, optionally substituted alkoxycarbonyl, optionally substituted acyl, optionally substituted cycloalkyl, optionally substituted cycloalkenyl, optionally substituted aryl, optionally substituted heterocyclyl, optionally substituted cycloalkyloxy, optionally substituted cycloalkenyloxy, optionally substituted aryloxy, or optionally substituted heterocyclyloxy, or $R^1$ and $R^2$ together with the adjacent nitrogen atom form an optionally substituted ring;

$R^3$ and $R^4$ are each independently hydrogen, halogen, optionally substituted alkyl or optionally substituted alkoxy;

W is —C($R^5$)($R^6$)— or —O—;

$R^5$ and $R^6$ are each independently hydrogen, alkyl, hydroxyalkyl, alkoxyalkyl, carboxy, alkoxycarbonyl, carbamoyl or alkylcarbamoyl;

Y is —S(O)$_2$—;

Z is optionally substituted cycloalkyl, optionally substituted cycloalkenyl, optionally substituted aryl or optionally substituted heterocyclyl;

R is alkyl, hydroxyalkyl, alkoxyalkyl, carboxy, alkoxycarbonyl, carbamoyl or alkylcarbamoyl;

m is 0 or 1;

n is 1 or 2; and p is 0, 1, or 2, excluding compounds wherein Q is (B) and $R^2$ is N-containing heterocyclyl substituted by fluoronaphtylmethyl.

2. The compound of claim 1, a pharmaceutically acceptable salt or a solvate thereof, wherein Q is (A), W is —C($R^5$)($R^6$)—, n is 2 and m is 0.

3. The compound of claim 1, a pharmaceutically acceptable salt or a solvate thereof, wherein Q is (A), W is —O—, n and m are both 1.

4. The compound of claim 1, a pharmaceutically acceptable salt or a solvate thereof, wherein Q is (B), n is 2,m is 0, and W is —C($R^5$)($R^6$)—.

5. The compound of claim 1, a pharmaceutically acceptable salt or a solvate thereof, wherein Z is optionally substituted aryl.

6. The compound of claim 5, a pharmaceutically acceptable salt or a solvate thereof, wherein Z is optionally substituted phenyl.

7. The compound of claim 1, a pharmaceutically acceptable salt or a solvate thereof, wherein $R^1$ is hydrogen or optionally substituted alkyl, and $R^2$ is optionally substituted alkyl, optionally substituted aryl or optionally substituted cycloalkyl.

8. The compound of claim 1, a pharmaceutically acceptable salt or a solvate thereof, wherein $R^3$ is hydrogen or optionally substituted alkoxy.

9. A pharmaceutical composition comprising a compound of claim 1, a pharmaceutically acceptable salt or a solvate thereof and a pharmaceutically acceptable carrier.

10. The pharmaceutical composition of claim 9, which is used for palliatively treating pain selected from chronic pain, acute pain, and surgical pain.

11. A method of palliatively treating a disorder responsive to the blockade of calcium channels in a mammal suffering from said disorder, comprising administering to a mammal in need of such palliative treatment an effective amount of a compound of claim 1, a pharmaceutically acceptable salt or a solvate thereof.

12. The method of claim 11, wherein a disorder responsive to the blockade of N-type calcium channels is palliatively treated.

13. A method for palliatively treating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal, comprising administering an effective amount of a compound of claim 1, a pharmaceutically acceptable salt or a solvate thereof.

14. The method of claim 13, wherein the method is for palliatively treating pain selected from chronic pain, acute pain, and surgical pain.

15. A method of modulating calcium channels in a mammal, comprising administering to the mammal at least one compound of claim 1, a pharmaceutically acceptable salt or a solvate thereof.

16. The method of claim 15, wherein the N-type calcium channel is modulated.

17. A compound of claim 1, a pharmaceutically acceptable salt or a solvate thereof, for use in a method for palliatively treating pain selected from chronic pain, acute pain, and surgical pain.

* * * * *